US007647092B2

(12) United States Patent
Motz et al.

(10) Patent No.: US 7,647,092 B2
(45) Date of Patent: Jan. 12, 2010

(54) SYSTEMS AND METHODS FOR SPECTROSCOPY OF BIOLOGICAL TISSUE

(75) Inventors: Jason T. Motz, Cambridge, MA (US); Luis H. Galindo, Fitchberg, MA (US); Martin Hunter, Belmont, MA (US); Ramachandra Dasari, Lexington, MA (US); Michael S. Feld, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 580 days.

(21) Appl. No.: 10/178,062

(22) Filed: Jun. 21, 2002

(65) Prior Publication Data

US 2003/0191398 A1    Oct. 9, 2003

Related U.S. Application Data

(60) Provisional application No. 60/370,197, filed on Apr. 5, 2002.

(51) Int. Cl.
*A61B 6/06* (2006.01)
(52) U.S. Cl. ........................... 600/478; 385/53; 385/115
(58) Field of Classification Search ................. 600/476, 600/478; 385/53–94, 115–121, 123–128; 359/723; 356/402, 416; 422/82.05, 82.11
See application file for complete search history.

(56) References Cited

U.S. PATENT DOCUMENTS

| 4,573,761 | A |   | 3/1986 | McLachlan et al. | ....... 350/96.24 |
|---|---|---|---|---|---|
| 5,217,454 | A |   | 6/1993 | Khoury | ........................ 606/7 |
| 5,293,872 | A |   | 3/1994 | Alfano et al. | ................ 128/664 |
| 5,304,173 | A | * | 4/1994 | Kittrell et al. | ................. 606/15 |
| 5,398,670 | A | * | 3/1995 | Ortiz et al. | .................. 600/114 |
| 5,402,508 | A |   | 3/1995 | O'Rourke et al. | ............. 385/31 |
| 5,510,894 | A |   | 4/1996 | Batchelder et al. | .......... 356/301 |
| 5,615,673 | A | * | 4/1997 | Berger et al. | ................. 600/326 |

(Continued)

FOREIGN PATENT DOCUMENTS

EP    0 230 679    8/1987

(Continued)

OTHER PUBLICATIONS

Motz, J.T.; Optical Fiber Probe Development for Clinical Raman Spectroscopy; Laser Biomedical Research Center, MIT Apr. 8, 2002.

(Continued)

*Primary Examiner*—Long V Le
*Assistant Examiner*—Jacqueline Cheng
(74) *Attorney, Agent, or Firm*—Weingarten, Schurgin, Gagnebin & Lebovici LLP

(57) ABSTRACT

The system and method of the present invention relates to using spectroscopy, for example, Raman spectroscopic methods for diagnosis of tissue conditions such as vascular disease or cancer. In accordance with a preferred embodiment of the present invention, a system for measuring tissue includes a fiber optic probe having a proximal end, a distal end, and a diameter of 2 mm or less. This small diameter allows the system to be used for the diagnosis of coronary artery disease or other small lumens or soft tissue with minimal trauma. A delivery optical fiber is included in the probe coupled at the proximal end to a light source. A filter for the delivery fibers is included at the distal end. The system includes a collection optical fiber (or fibers) in the probe that collects Raman scattered radiation from tissue, the collection optical fiber is coupled at the proximal end to a detector. A second filter is disposed at the distal end of the collection fibers. An optical lens system is disposed at the distal end of the probe including a delivery waveguide coupled to the delivery fiber, a collection waveguide coupled to the collection fiber and a lens.

21 Claims, 50 Drawing Sheets

U.S. PATENT DOCUMENTS

| | | | | |
|---|---|---|---|---|
| 5,764,840 | A | 6/1998 | Wach | 385/123 |
| 5,878,178 | A | 3/1999 | Wach | 385/55 |
| 5,901,261 | A | 5/1999 | Wach | 385/38 |
| 5,911,017 | A | 6/1999 | Wach et al. | 385/12 |
| 5,917,971 | A | 6/1999 | Slater | 385/31 |
| 5,943,128 | A | 8/1999 | Slater | 356/301 |
| 5,953,477 | A | 9/1999 | Wach et al. | 385/115 |
| 5,974,211 | A | 10/1999 | Slater | 385/33 |
| 6,038,363 | A | 3/2000 | Slater et al. | 385/147 |
| 6,067,156 | A | 5/2000 | Slater et al. | 356/301 |
| 6,141,095 | A | 10/2000 | Allen et al. | 356/301 |
| 6,144,791 | A | 11/2000 | Wach et al. | 385/123 |
| 6,278,534 | B1 | 8/2001 | Arns | 359/15 |
| 6,281,971 | B1 | 8/2001 | Allen et al. | 356/301 |
| 6,487,349 | B2 * | 11/2002 | Wach et al. | 385/115 |
| 2001/0012429 | A1 | 8/2001 | Wach et al. | 385/115 |
| 2004/0073120 | A1 * | 4/2004 | Motz et al. | 600/478 |

FOREIGN PATENT DOCUMENTS

| | | |
|---|---|---|
| JP | 10267846 | 10/1998 |
| JP | 2002136469 | 5/2002 |
| WO | WO 89/02718 | 4/1989 |
| WO | WO 92/15008 | 3/1992 |
| WO | WO 93/03672 | 3/1993 |
| WO | WO 96/29925 | 10/1996 |
| WO | WO 97/48995 | 12/1997 |
| WO | WO 98/05253 | 2/1998 |

OTHER PUBLICATIONS

Buschman, H.P., et al.; Raman microspectroscopy of human coronary atherosclerosis: Biochemical assessment of cellular and extracellular morphologic structures in situ; Cardiovascular Pathology 10 (2001) 69-82.

Buschman, H.P., et al.; Diagnosis of human coronary atherosclerosis by morphology-based Raman spectroscopy; Cardiovascular Pathology 10 (2001) 59-68.

Hanlon, E.B., et al.; Prospects for in vivo Raman spectroscopy; Phys. Med. Biol. 45 (2000) R1-R59.

van de Poll, S.W.E., et al.; Prospects of Laser Spectroscopy to Detect Vulnerable Plaque; Cardiovascular Plaque Rupture (ed. Brown, D.); Marcel Dekker, NY, NY (2002).

Motz, J.T., et al.; The Raman spectrum of atherosclerosis: A review of newly developed modeling techniques; Res. Adv. In Appl. Spectrosc., 1:49-67 (2000).

Buschman, H.P.J., et al.; Human coronary atherosclerosis studied by morphological NIR Raman confocal microspectroscopy; SPIE Proc.; 3608:7-11 (1999).

Buschman, H.P.J., et al.; Morphologic modeling and histopathological classification of human coronary atherosclerosis by morphology based Raman spectroscopy; Eur. Soc. Cardiol., Barcelona Spain (1999).

Motz, J.T., et al.; Development of Optical Fiber Probes for Biological Raman Spectroscopy; Optical Society of America, Biomedical Topical Meeting Apr. 7-10, 2002.

Haka, A.S., et al.; Spectral Diagnosis of Atherosclerosis: Fluorescence or Raman; Lester Wolfe Symposium on "Optical Methods for Detection and Treatment of Atherosclerosis"; Massachusetts Institute of Technology: Dec. 11, 2001.

Motz, J.T., et al.; Raman Diagnosis of Atherosclerosis: A Morphological/Histochemical Approach Federal Drug Administration/Biomedical Research Foundation Conference on Applications of Lasers to Cardiology at the Federal Drug Administration, May 9-10, 2000.

* cited by examiner

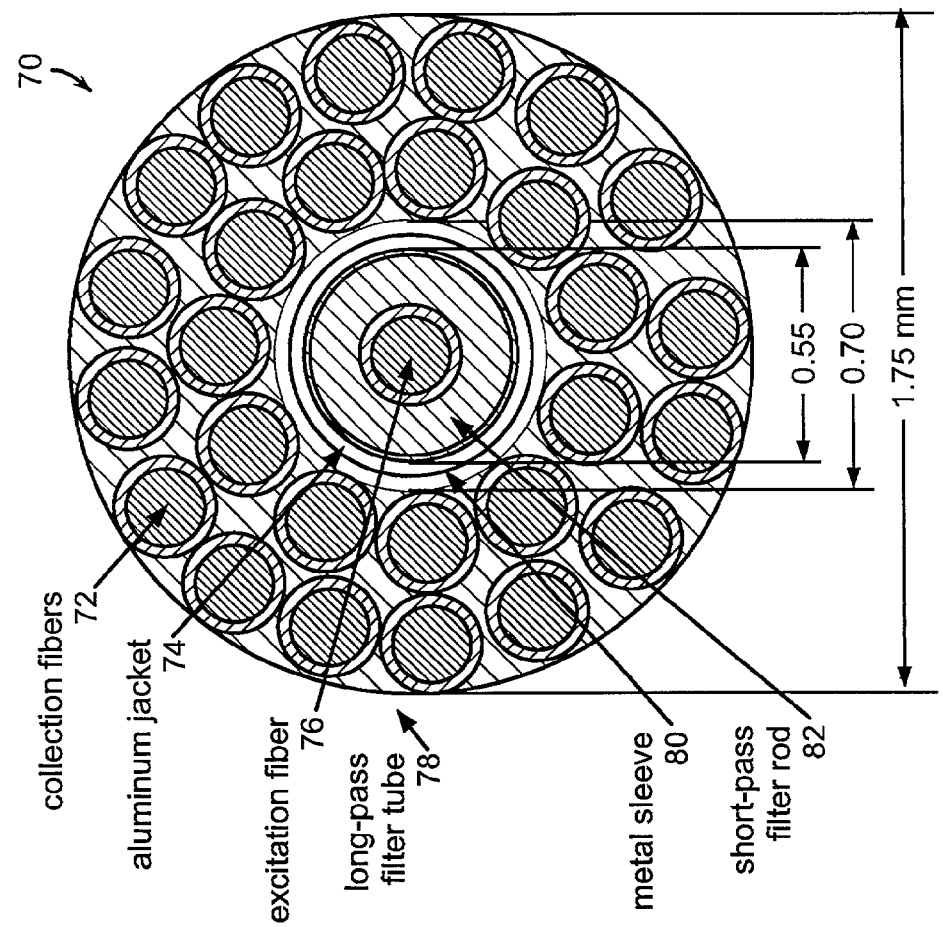
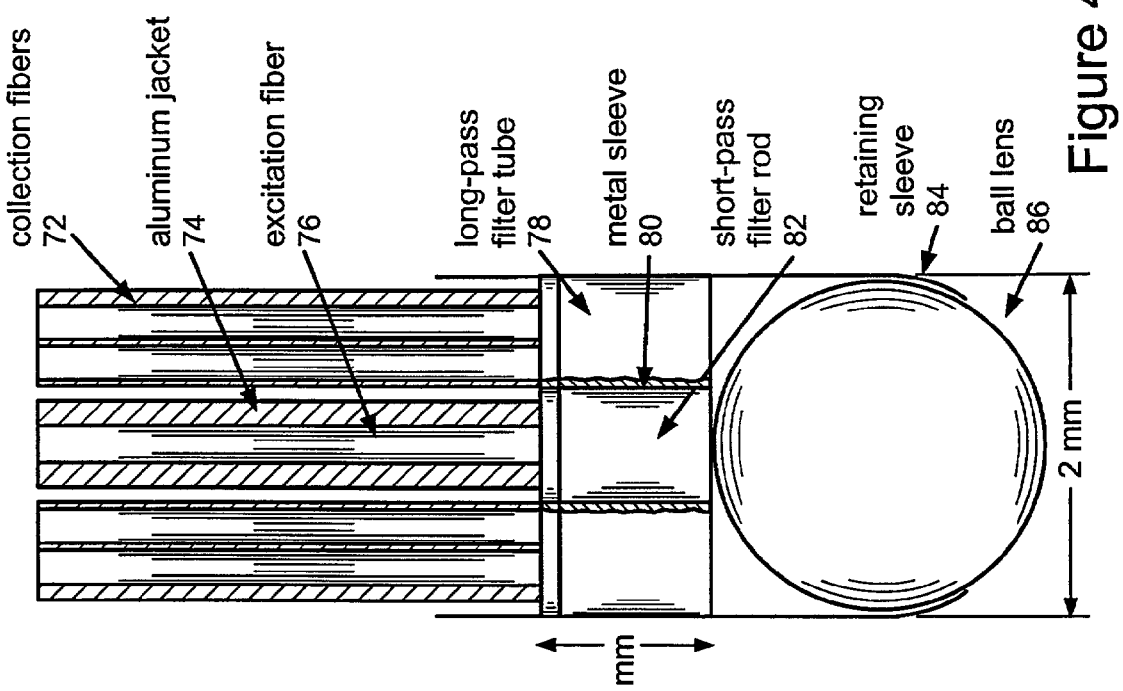
Figure 4B
Figure 4A

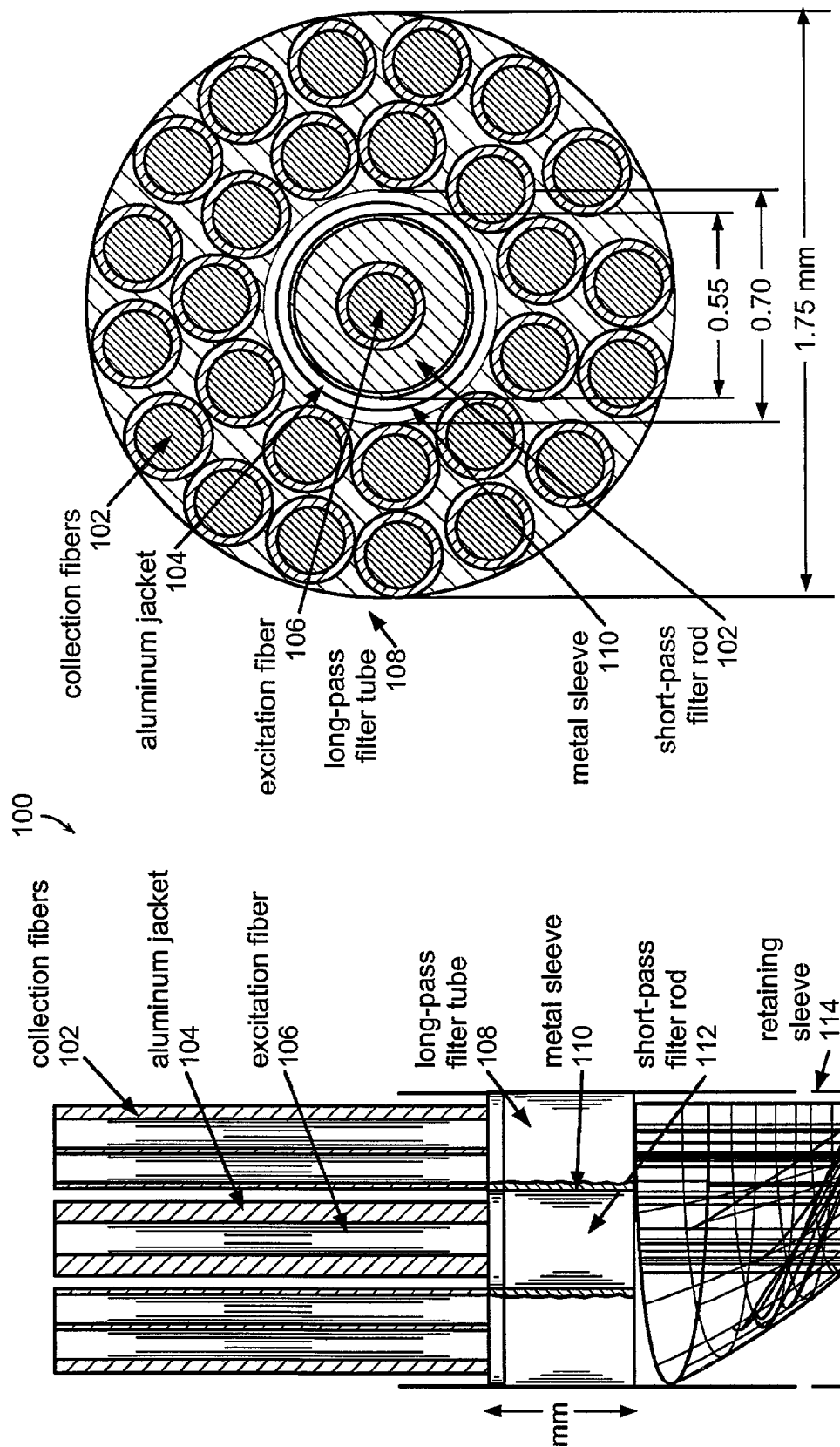

SYSTEMS AND METHODS FOR SPECTROSCOPY OF BIOLOGICAL TISSUE

CROSS REFERENCES TO RELATED APPLICATIONS

The present application claims the benefit of the U.S. Provisional Patent Application No. 60/370,197, filed Apr. 5, 2002. The entire contents of the above application is incorporated herein by reference in its entirety.

GOVERNMENT SUPPORT

This invention was supported, in whole or in part, by grants P41-RR-02594 and NIH-HL-64675 from the National Institute of Health. The Government has certain rights in the invention.

BACKGROUND OF THE INVENTION

Optical methods are increasingly being used for the detection of disease. Near-infrared Raman spectroscopy in particular, because of its chemical specificity, is proving to be a useful tool for both disease diagnosis and the study of disease progression. Over the past decade Raman spectroscopy has been applied to many diseases and biological problems and there have been many advances in-vitro. More recently there have been reports of in-vivo work that however have either been confined to studies of skin or other easily accessible organs, or have used optical fiber configurations that require collection times that are unreasonably long for practical clinical use. The majority of applications require remote sampling via optical fibers, and the size of the probe and fiber bundle is strictly limited by the application. A particular example that current commercial systems cannot provide is the ability to evaluate atherosclerotic lesions in-vivo in real-time, through an angiographic catheter, thus aiding cardiologists in directing the most appropriate treatment in each individual case. These objectives have not been fulfilled by current systems.

In addition, prior art probes for remote Raman sensing, using several different methods for filtering out the fiber spectral background, either exhibit extremely low optical throughput or are too bulky to be used intravascularly. A problem with the prior art designs includes having a 4 cm long stiff tip that prohibits their incorporation into transcutaneous catheters for accessing the coronary arteries. Secondly, in data collected with these probes, a considerable component of the fiber Raman spectrum still remains. Further, data collection times on the order of 30 seconds or longer are typically required for collection of signals with an acceptable signal to noise ratio (SNR).

A need still exists for improved systems and methods which include probes for, for example, Raman spectroscopy that are sized for applications in medicine and provide an improved spectral signature from tissue.

SUMMARY OF THE INVENTION

The system and method of the present invention relates to using spectroscopy, for example, Raman spectroscopic methods for diagnosis of tissue conditions such as vascular disease or cancer. The system and methods of the present invention have several applications: optical breast biopsies and breast analysis through ductoscopy, percutaneous blood analysis and monitoring, vascular stenosis, gastrointestinal cancer evaluation, scanning for dysplasia in the pancreatic duct and skin analyses.

In accordance with a preferred embodiment of the present invention, a system for measuring tissue includes a fiber optic probe having a proximal end, a distal end, and a diameter of 2 mm or less. This small diameter allows the system to be used for the diagnosis of coronary artery disease or other small lumens or soft tissue with minimal trauma. A delivery optical fiber (or fibers) is included in the probe coupled at the proximal end to a light source. A filter for the delivery fibers is included at the distal end. The system includes a collection optical fiber (or fibers) in the probe that collects Raman scattered radiation from tissue, the collection optical fiber is coupled at the proximal end to a detector. A second filter is disposed at the distal end of the collection fibers. An optical lens system is disposed at the distal end of the probe including a delivery waveguide coupled to the delivery fiber, a collection waveguide coupled to the collection fiber and a lens.

The delivery waveguide comprises a rod and the collection waveguide comprises a cylindrical tube, the tube being concentric about the rod. In an alternate preferred embodiment, the delivery waveguide comprises a first tube and the collection waveguide comprises a second cylindrical tube, the second tube being concentric about the first tube. Further the lens includes a ball lens optically coupled to the delivery fiber and the collection fiber.

In a preferred embodiment, the probe further comprises a sleeve that optically isolates the delivery waveguide from the collection waveguide. The sleeve can be metallic, such as palladium, silver or gold. The glass rod tube and sleeve can be attached together with an adhesive. An outer retaining sleeve can attach the distal optics to the fiber optics.

The probe further comprises a first plurality of collection fibers arranged concentrically about the delivery fiber at a first radius, and a second plurality of collection fibers arranged concentrically about the delivery fiber at a second radius that is larger than the first radius.

In accordance with another aspect of the present invention, the probe includes a controller that gates a collection time, the collection time being less than 2 seconds. In one embodiment, the optical lens system has a length less than 10 mm. In a preferred embodiment, the optical lens system has a length of less than 4 mm. The diameter of the distal optical system is preferably in the range of 1-2 mm. The optical lens systems delivers and collects radiation in a radial direction, which can be defined as any off-axis direction. The light source has a wavelength longer than 750 nm with a preferred embodiment using an argon laser pumped Ti: sapphire laser emitting at 830 nm. In an alternate embodiment a diode laser such as a InGaAs laser emitting at 785 nm or 830 nm may be used.

In a preferred embodiment, the radial Raman probe in accordance with the present invention for use in diagnosing atherosclerosis is incorporated in a catheter of the type used for angiography, for example. It includes a balloon for displacing blood and other fluids and to position the catheter in the artery. A preferred embodiment includes a channel for balloon inflation. Further, the catheter system includes the capability for flushing away the blood temporarily with a fluid, for example, saline. One or several optical fibers can be configured so as to direct excitation light in a radial direction, either to the side or at an angle ranging from 45°-90°. In such a preferred embodiment a balloon disposed on the side is used to contact the fibers adjacent the artery wall, and displace blood or other intervening fluids.

Alternately, the delivery fibers can be arranged to direct light in a circular pattern at an angle to the axis of the probe. The different collection fibers collect light simultaneously from different portions of the circumferential region illuminated. In this embodiment, the probe is enclosed in an inflatable balloon which is inflated before light delivery and/or collection to displace blood and other fluids. In preferred embodiments, the balloon is of a type used in arterial applications, such as, for example, angioplasty, and are made of thin material so as to allow excitation light to pass through to the artery wall, and return Raman light generated in the artery wall to pass through the balloon to the collection fibers.

The present invention includes the diagnostic classification of atherosclerotic plaques in human coronary arteries by quantitative assessment of their morphologic composition using Raman spectroscopy. The rapid and nondestructive nature of Raman spectroscopy provides the opportunity to diagnose coronary artery plaques in-vivo, when applied in a clinical setting using optical fiber technology. So used, the preferred embodiments of the present invention classify an atherosclerotic lesion, and can provide in-vivo quantitative assessment of its morphologic features, such as the presence of foam cells (FC), necrotic core (NC), and cholesterol crystals (CC), which may be used to assess plaque instability and the extent of disease progression, and thereby, the risk of life-threatening complications such as thrombosis and acute plaque hemorrhage. So used, the methods of the present invention may provide insight into as yet poorly understood dynamics in the evolution of atherosclerotic lesions and the effects of lipid-lowering and other therapies.

Chemical composition and morphology, rather than anatomy (degree of stenosis), determine atherosclerotic plaque instability and predict disease progression. In a preferred embodiment, a modification of the Raman spectroscopy reference data can also be used to identify the microscopic morphologic structures comprising the plaque, and the pathological state of the artery can be accurately assessed using a diagnostic algorithm based on the relative contribution of these microscopic morphological structures to the macroscopic arterial Raman spectrum.

In a preferred embodiment eight atherosclerotic classes are used for comparison with previous studies using the principal component analysis (PCA) and chemical reference data. These eight classes are reduced to three classes. On pathologic examination, the presence of FC, NC, and CC are significant predictors of plaque instability and disease progression. The embodiments of the present invention show that Raman spectroscopic analysis of these same morphologic structures can be used to diagnose atherosclerotic lesions in intact coronary arteries, without the need for microscopic examination. This suggests that Raman spectroscopy can provide not only quantitative chemical information, but also quantitative morphologic information regarding atherosclerotic lesion composition, such as the presence of CC, not readily available in current diagnostic imaging techniques such as intravascular ultrasound (IVUS), magnetic resonance imaging (MRI), and angiography.

In a preferred embodiment, the spectral signatures of the cellular and extracellular morphologic components of normal and atherosclerotic arterial tissue in-situ are determined using confocal Raman microspectroscopy. The specific morphologic structures are selected because of their role in normal arterial anatomy (e.g. elastic laminae) and/or atherosclerotic plaque formation (e.g. foam cells, necrotic core, cholesterol crystals). Least-squares minimization of a linear combination of the basis spectra of 12 biochemical components provide information on the biochemical composition of the various morphologic structures. These biochemical components are selected because they were known to be present in high concentration in normal arterial tissue and/or atherosclerotic plaque (e.g. collagen, elastin, and free and esterified cholesterol) or because they are strong Raman scatterers (e.g. β-carotene). Glycosaminoglycans (e.g. hyaluronic acid, chondroitin sulfate, dermatan sulfate, and heparan sulfate), which may contribute 3% of artery dry mass, did not contribute significantly to the biochemical model and reference data fits, most likely because they are weak Raman scatterers (i.e. they have small Raman cross sections), and were excluded from the reference data.

The embodiments of the present invention interpret Raman spectra in terms of morphology. For example, the Raman spectra can be associated with a morphological structure, for example, a foam cell which can be associated with specific chemical compounds. Further, the number of spectra can be reduced, for example, from a large number of chemical spectra to only eight unique spectra associated with morphological structures thereby decreasing the error in the fit. The diagnostics that are available to identify and monitor vulnerable plaque using the optical fiber catheter system of the present invention include the use of chemical composition, information about the morphological structures, thickening of the intimal layer and the thinning of the overlying collagen layer. Preferred embodiments include the determination of the depth of collagen by measuring the percentage of collagen. Further, the presence of calcification is monitored and any edges are identified and located relative to the collagen as indicators of a potential rupture and blood clot. Further, the reduced fractional fit contributions of collagen fibers in non-calcified plaques is an indication of decreased plaque stability.

The foregoing and other features and advantages of the systems and methods for spectroscopy of in-vivo biological tissue will be apparent from the following more particular description of preferred embodiments of the system and method as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIG. 4A is a longitudinal view of an apparatus including a probe for measuring tissue in accordance with a preferred embodiment of the present invention.

FIG. 4B is a transverse view of the probe illustrated in FIG. 4A in accordance with a preferred embodiment of the present invention.

FIGS. 4C and 4D are a longitudinal and transverse view respectively of an alternate embodiment of a probe for measuring tissue with a paraboloidal mirror in accordance with the system of the present invention.

FIGS. 24A-24C graphically illustrate the results of the fit contribution of seven morphologic structures to the calibration data set and the diagnostic algorithm classification wherein FIG. 24A illustrates nonatherosclerotic tissue, FIG. 24B illustrates noncalcified atherosclerotic plaque and FIG. 24C illustrates calcified atherosclerotic plaque in accordance with a preferred embodiment of the present invention.

DETAILED DESCRIPTION OF THE INVENTION

Figures 1A, 1B:
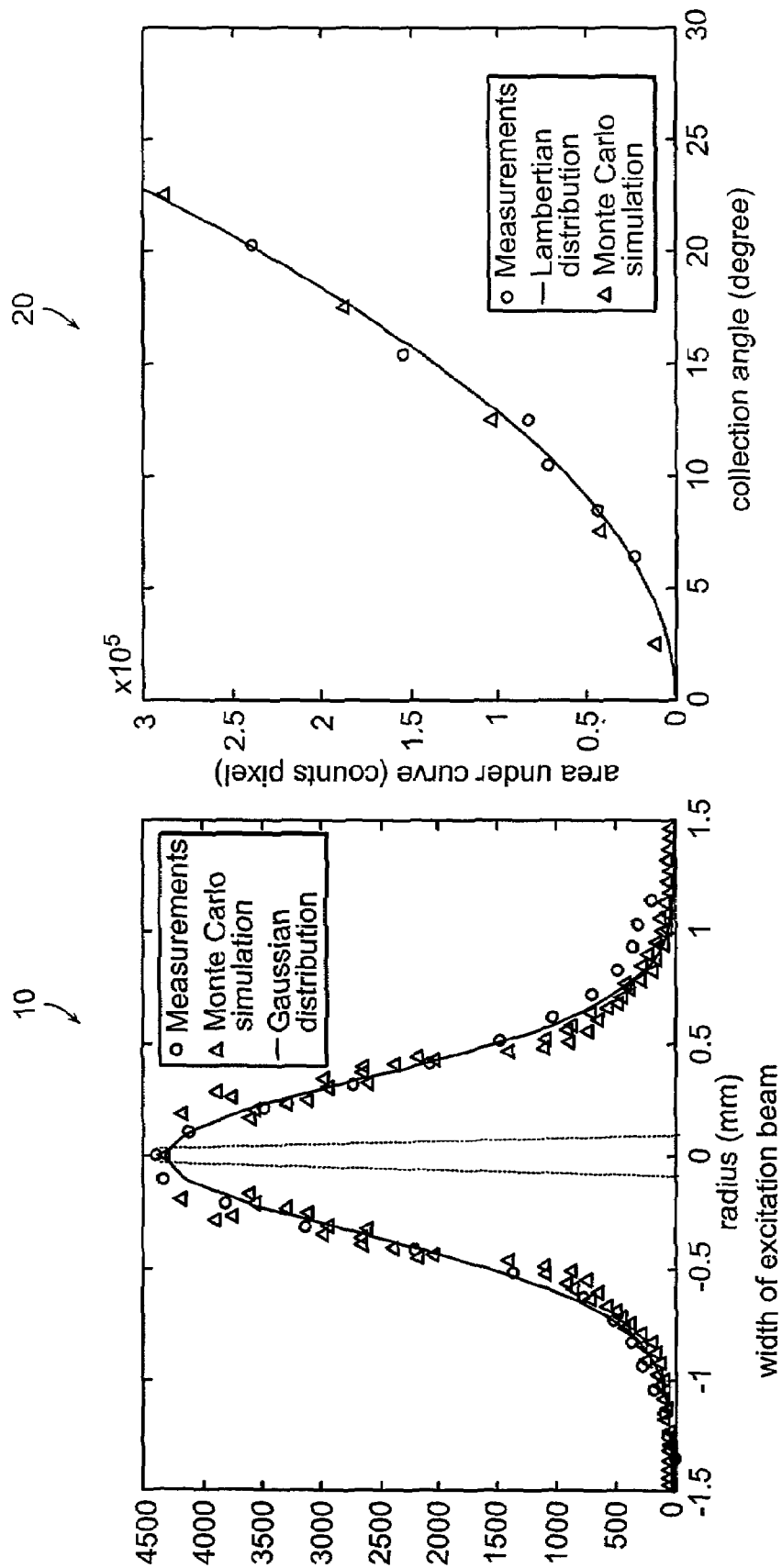
FIG. 1A graphically illustrates a comparison of theory, simulations and results for Raman emission data of turbid samples of blood tissue for the radial distribution of the Raman scattered light in accordance with a preferred embodiment of the present invention.
FIG. 1B graphically illustrates a comparison of simulations, theory and results for Raman emission data of turbid samples of blood tissue for angular distribution of the Raman scattered light in accordance with a preferred embodiment of the present invention.

The present invention is directed to systems and methods for using Raman spectroscopy of tissue. A predicate for developing systems and methods for in-vivo applications using angiographic catheters to aid cardiologists in directing the appropriate treatment is the development of optical fiber probes for Raman spectroscopy capable of delivering low energy laser light to, and efficiently collecting the resulting Raman spectral signature from, in-vivo tissue. The probes in preferred embodiments are small, and use micro-optical design principles.

Methods for performing Raman spectroscopy for diagnosis and treatment of tissue are described in U.S. Pat. No. 5,615,673 issued on Apr. 1, 1997, in U.S. Pat. No. 5,304,173 issued on Apr. 19, 1994, in International Publication No. WO 92/15008, published on Sep. 3, 1992 and in International Publication No. WO 96/29925 published on Oct. 3, 1996, the entire teachings of all the references are incorporated herein by reference.

There are at least two difficulties to be overcome in producing such probes. The first is due to the spectral background signal generated in the delivery and collection fibers themselves, which may be orders of magnitude larger than the signal from the tissue site being examined. This background signal includes Raman light from the fused silica core, fluorescence from impurities and dopants used to design fibers of a particular numerical aperture (NA), as well as signal from various jacket materials. Laser light in the delivery fibers generates an intense fiber background due to the long path length traversed in the fibers, typically three to four meters. This fiber spectrum is scattered from the tissue surface and is collected, along with the tissue Raman spectrum, by the collection fibers, often masking the tissue Raman signal which is generated from only approximately 1 mm of sample due to the relatively short penetration of light into tissue.

In addition, laser light backscattered from the tissue is also collected by the collection fibers, and this scattered laser light produces an additional fiber spectrum originating in the collection fibers, which further compromises the quality of the tissue spectrum reaching the detector. In addition to obscuring and distorting the spectrum of interest, the intense fiber background adds a level of shot-noise to the signal and this noise can often be larger than the tissue Raman bands. Analyzing both delivery and collection fibers indicates that they both produce approximately equal amounts of this fiber spectral background. In a preferred embodiment, two different filters are used to suppress the undesired fiber background, one for delivery and one for collection. Further, it is desirable to terminate the delivery fibers with a short wavelength pass or band-pass filter that transmits the laser excitation light while blocking the longer wavelength spectral background generated in the delivery fibers. In a preferred embodiment, the collection fibers can be preceded by a long wavelength pass filter or notch filter which transmits the tissue Raman spectrum while blocking laser light backscattered from the tissue. Any filters used also perform the appropriate function over a range of angles corresponding to the acceptance angle (NA) of the fibers they are coupled to.

The second difficulty is related to signal collection. This has two components, the first of which pertains to the inherently weak nature of the Raman effect. Approximately only one out of every billion excitation photons are converted into a Raman photon. In a preferred embodiment, a high-throughput optical probe apparatus collects signals with sufficient signal-to-noise ratio (SNR) to be useful in a clinically realistic timeframe. To be clinically useful and commercially viable, a preferred embodiment collects high SNR spectra in approximately 1-2 seconds. The second component also addresses optimization of collection which is further compromised by absorption and scattering in the tissue which results in causing the light to be widely diffused over large areas and angles.

In a preferred embodiment the collection ability of an optical system is limited by its throughput, approximately given by the product of area of collection (A) and solid angle ($\Omega$) (A$\Omega$-product). The A$\Omega$ product is conserved throughout the system. In typical Raman spectroscopy systems, throughput is determined by the spectrograph/CCD collection detection system. In a preferred embodiment, the spectrograph is f/1.8 (NA=0.278) corresponding to a solid angle of $\Omega$=0.242sr, with a maximal slit height of 16 mm. To achieve sufficient spectral resolution for biological Raman spectroscopy a 0.2 mm slit width is used. Therefore, the maximal area of collection is A=3.2 mm$^2$, resulting in a theoretical maximal throughput of A$\Omega$=0.77 mm$^2$-sr. In a preferred embodiment a CCD detector is used to ensure that the effective Raman source generated in the tissue by the incident excitation light, no matter how bright, is optimally collected. The light is considered to be emitted over a large area and 4$\pi$ solid angle but is limited by the collection angle 2$7\pi$. Therefore the optimal trade-off between collection solid angle and area is determined in preferred embodiments of the present invention.

In a preferred embodiment system the spectrograph/CCD is replaced by a higher throughput system. For example, one such arrangement consists of a series of dichroic beam-splitters, filters and photodiodes. The filter wavelengths are determined to optimize multivariate spectral analysis with the minimum number of wavelengths. The exact number of wavelengths and bandwidths of the detector element depend on the spectral features of the chemical/morphological structures to be sensed. Such a system results in much greater throughput than the prior art spectrograph/CCD systems and is smaller, cheaper and does not require cooling, further eliminating bulk and expense.

Figure 10A:
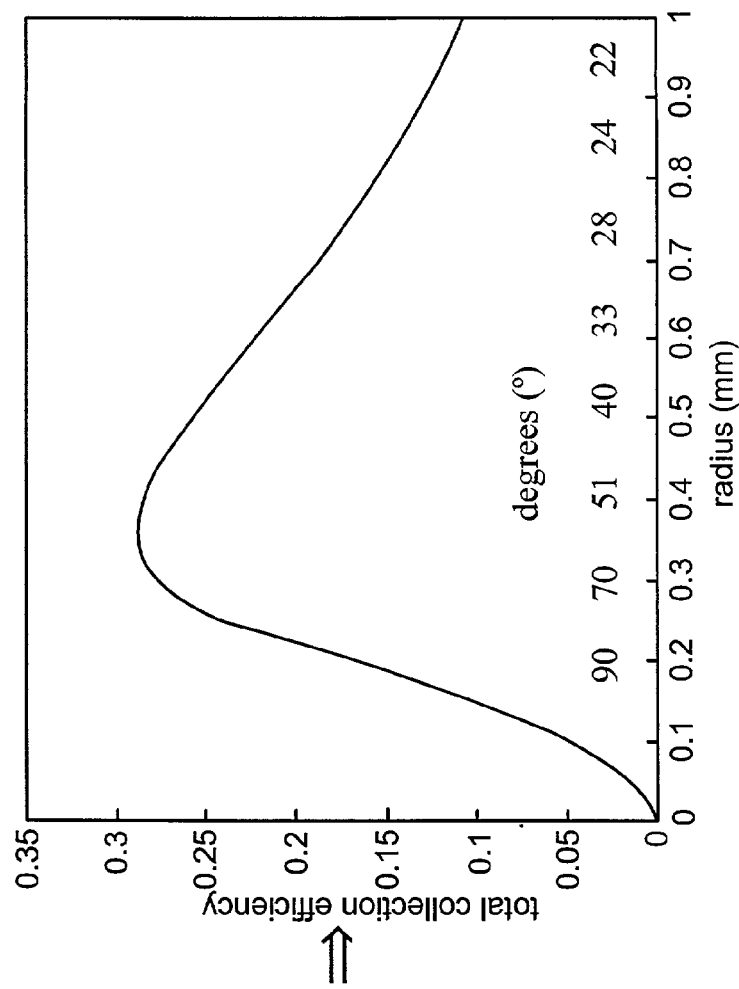
FIGS. 10A-10C are graphical representations of the integrated radial distributions, integrated angular distributions and optimized collection efficiency for blood tissue, respectively, in accordance with a preferred embodiment of the present invention.
Figure 10B:
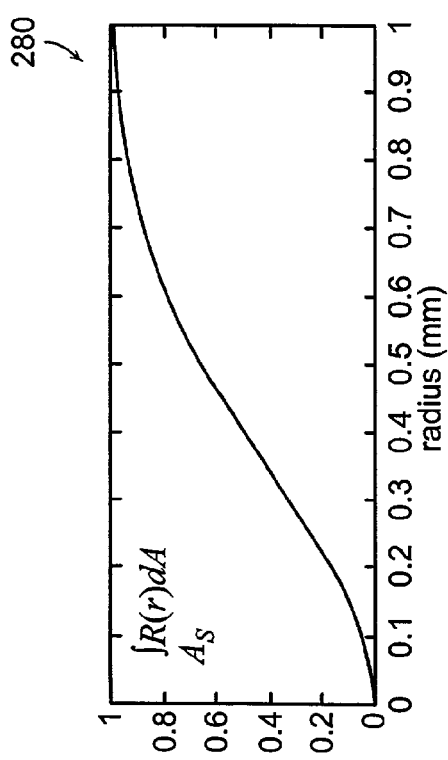
Figure 10C:
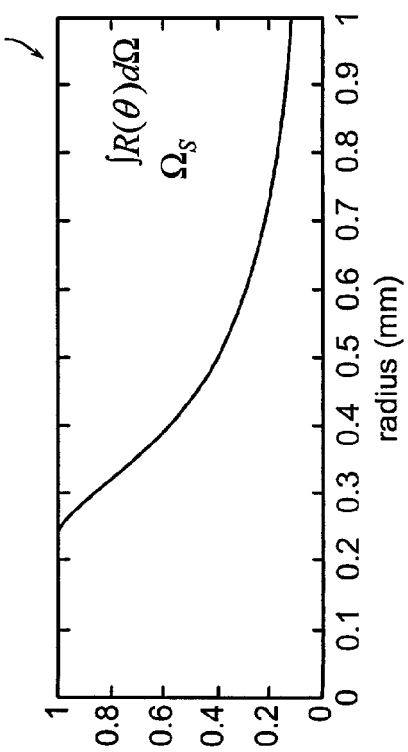

FIGS. 1A and 1B graphically illustrate a comparison of theory, simulations and results for Raman emission data of turbid samples of blood tissue for radial and angular distribution, respectively, of the Raman scattered light in accordance with a preferred embodiment of the present invention. Biological tissue is a collection of similar cells and the intercellular substances surrounding them. The four basic tissues in the body include epithelium tissue; connective tissues including blood, bone, and cartilage; muscle tissue; and nerve tissue. Most tissues with the exception of the cornea, are turbid, as they exhibit a high degree of elastic scattering, due to microscopic structures and refractive index variations contained therein and thus light entering such tissue is greatly diffused. Thus, the samples are characterized as turbid samples in FIGS. 1A, 1B, 10A-10C, 38A-38E. In a preferred embodiment, simulations such as, for example, Monte Carlo simulations are performed to predict the spatial and radial distribution of both the excitation and the Raman scattered light. In a preferred embodiment, the radial distribution is approximately Gaussian as shown in FIG. 1A, while the angular distribution is Lambertian as shown in FIG. 1B. Using these parameters and the optical throughput theorem which includes the conservation of the product of area and solid angle of the light being transmitted through an optical system, the optimal collection area and angles are determined. It should be recognized that the product $A\Omega$ is a constant and choosing the optimal combination of A and $\Omega$ is important as shown in FIGS. 10A-10C. In a preferred embodiment collection parameters of approximately 0.35 mm radius and 55° are optimal for blood tissue. The optimal collection parameters for artery tissue are approximately 0.4 mm radius and 20°. The results of the analyses are then incorporated into an optical design program such as, for example, Zemax program to determine appropriate optics for maximal signal collection.

Figure 38A:
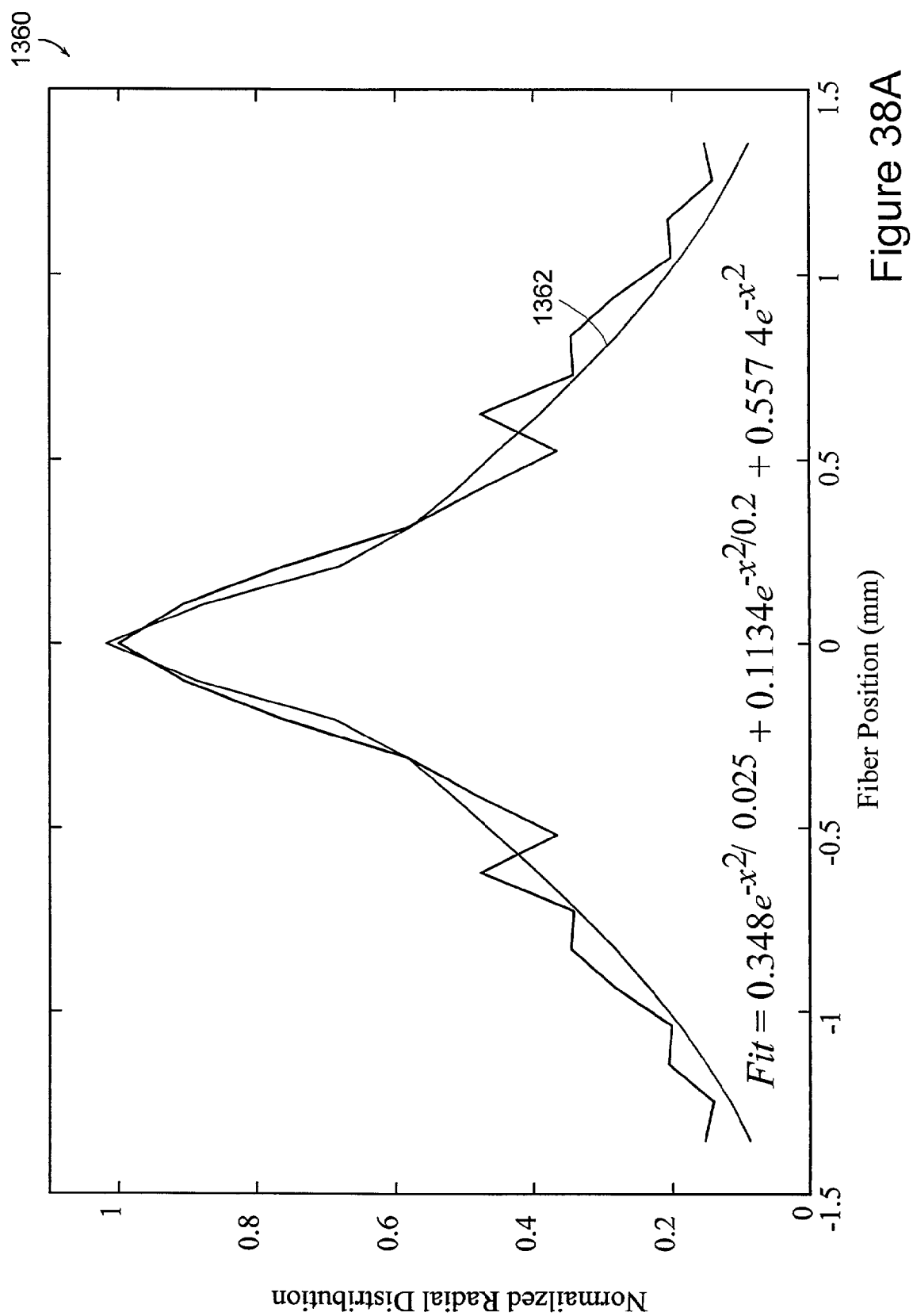
FIG. 38A graphically illustrates the results for Raman emission data of turbid samples of artery tissue for the radial distribution of the Raman scattered light in accordance with a preferred embodiment of the present invention.
Figure 38B:
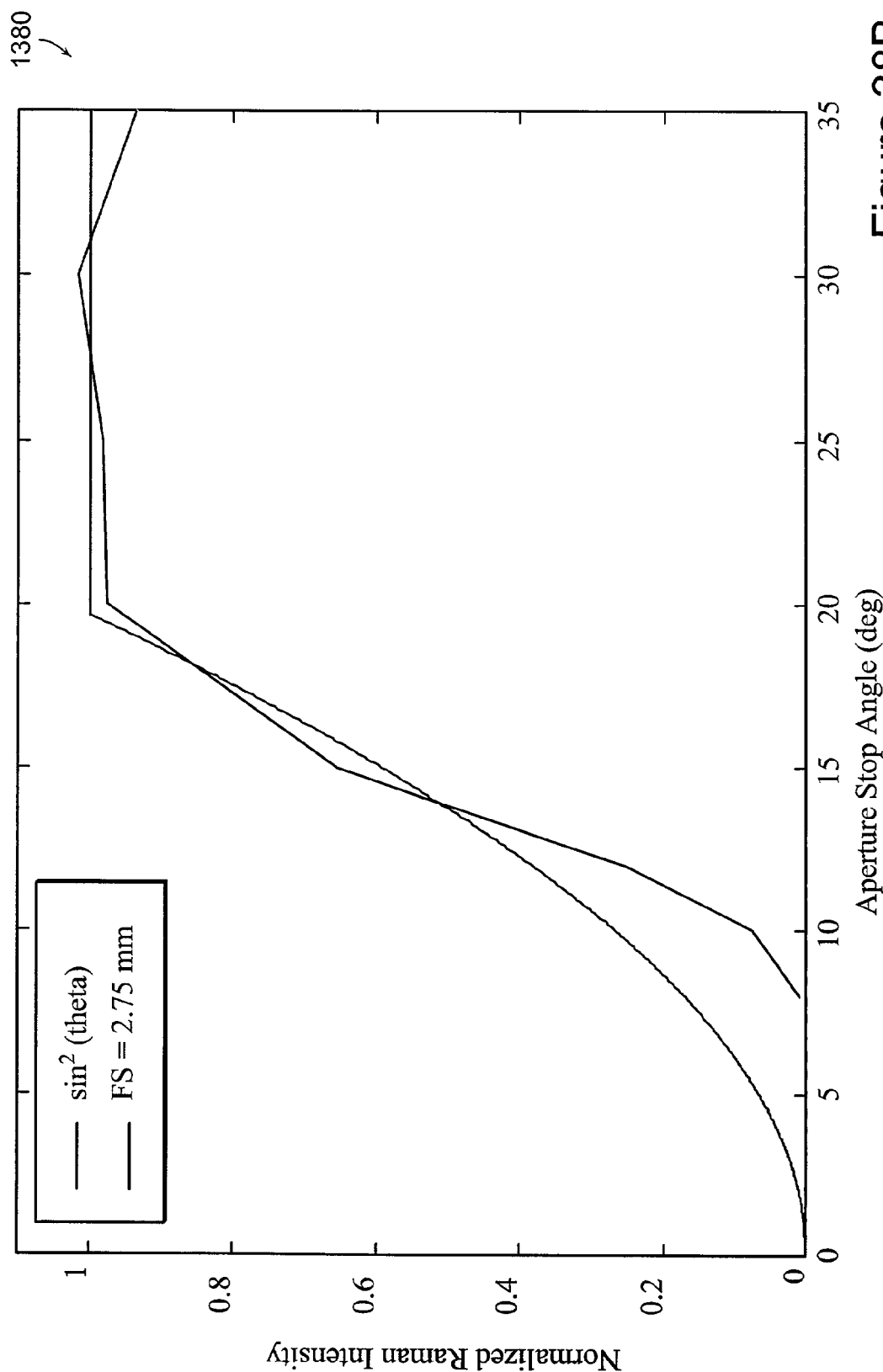
FIG. 38B graphically illustrates the results for Raman emission data of turbid samples of artery tissue for angular distribution of the Raman scattered light in accordance with a preferred embodiment of the present invention.
Figure 38E:
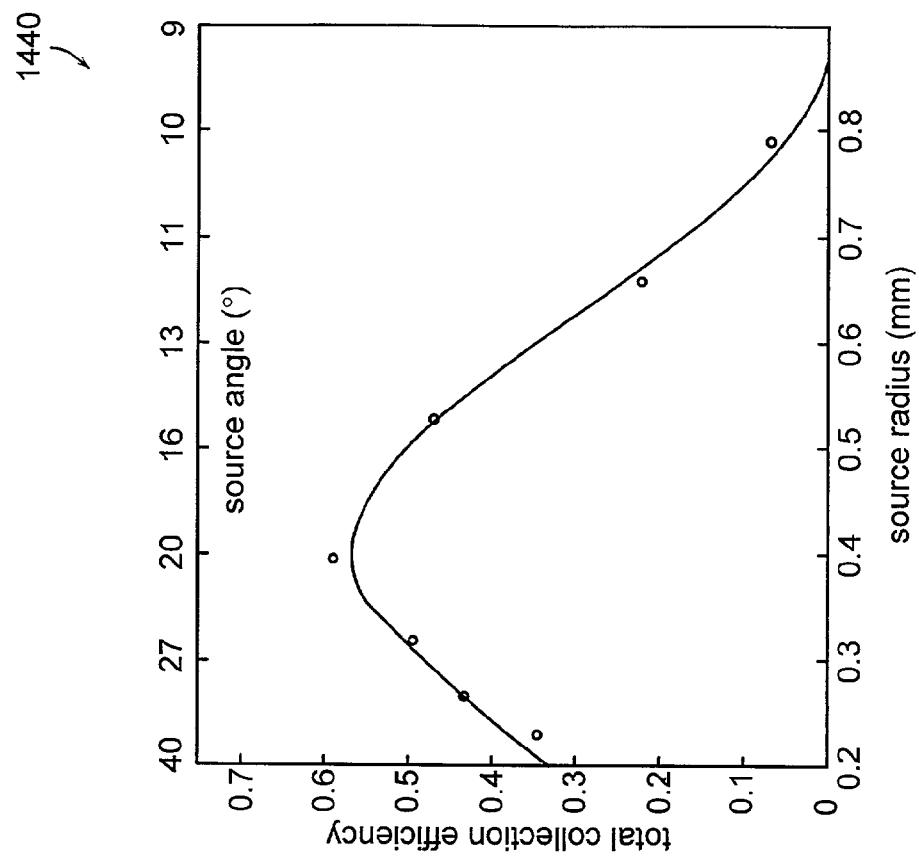
FIGS. 38C-38E are graphical representations of integrated radial distributions, integrated angular distributions and optimized collection efficiency of artery tissue, respectively, in accordance with a preferred embodiment of the present invention.
Figure 38C:
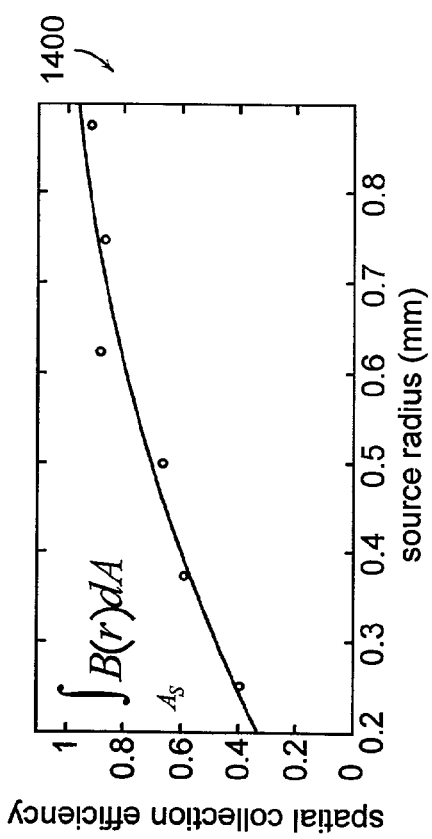
Figure 38D:
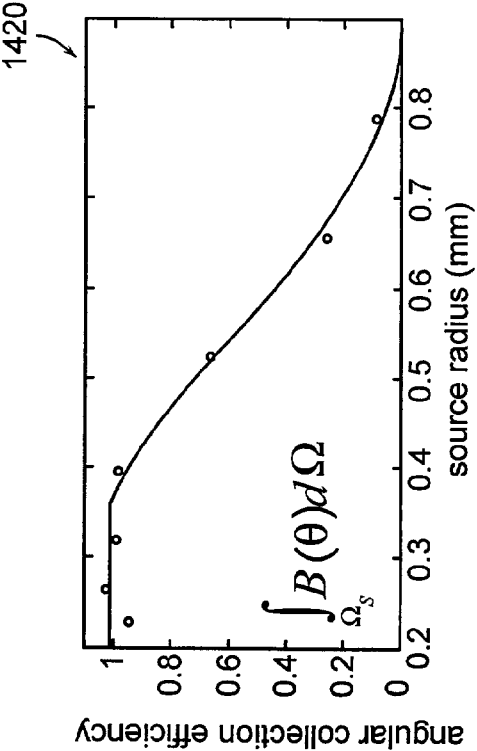

FIG. 38A graphically illustrates the results for Raman emission data 1360 of turbid samples of artery tissue in contrast to blood tissue described with respect to FIG. 1A for the radial distribution of the excitation and Raman scattered light in accordance with a preferred embodiment of the present invention. The curve 1362 illustrates the fit using a three Gaussian fit. Further, FIG. 38B graphically illustrates the results for Raman emission data 1360 of turbid samples of artery tissue for angular distribution of the excitation and Raman scattered light in accordance with a preferred embodiment of the present invention. Similar to FIGS. 10A-10C which illustrated distributions and collection efficiency for blood tissue; FIGS. 38C-38E are graphical representations of integrated radial distributions, integrated angular distributions and optimized collection efficiency for artery tissue, respectively, in accordance with a preferred embodiment of the present invention.

Optical elements are used to transfer the light collected from the tissue to the distal end of optical fibers in the probe. The proximal end of the fiber bundle is then re-shaped to match the shape, area, and NA of the spectrograph. These procedures are followed so as not to decrease light transmission efficiency, and provide effective coupling. The choice of collection fiber NA and collection fiber diameter is determined by the spectrometer NA, the desired spectral resolution, and considerations of matching optics, as well as the limitation set by filter acceptance angle. The trade-offs for the system include the spectrometer chosen, and the desired resolution determines a slit width. At the output end the collection fibers are arranged in a straight line, which is imaged onto the entrance slit by the matching optics. Considering the throughput theorem, the requirement on the collection fibers includes that the product of fiber NA and diameter equal the product of spectrometer NA and slit width. If a fiber is chosen which satisfies the stronger condition that the fiber diameter equals the slit width and the fiber NA equals the spectrometer NA, the necessity of using matching optics is eliminated and the probe is directly coupled into the spectrometer. If only the product requirement can be satisfied then matching optics are needed. In an alternate embodiment, spectrometers use curved slits, and the output end of the collection fibers can be modified to match any slit shape. An upper limit on the number of collection fibers is defined by the height of the fiber array image that is less than the slit height or CCD chip, whichever is less. However a smaller limitation may be set by the space available in the collection tip.

Figure 2A:
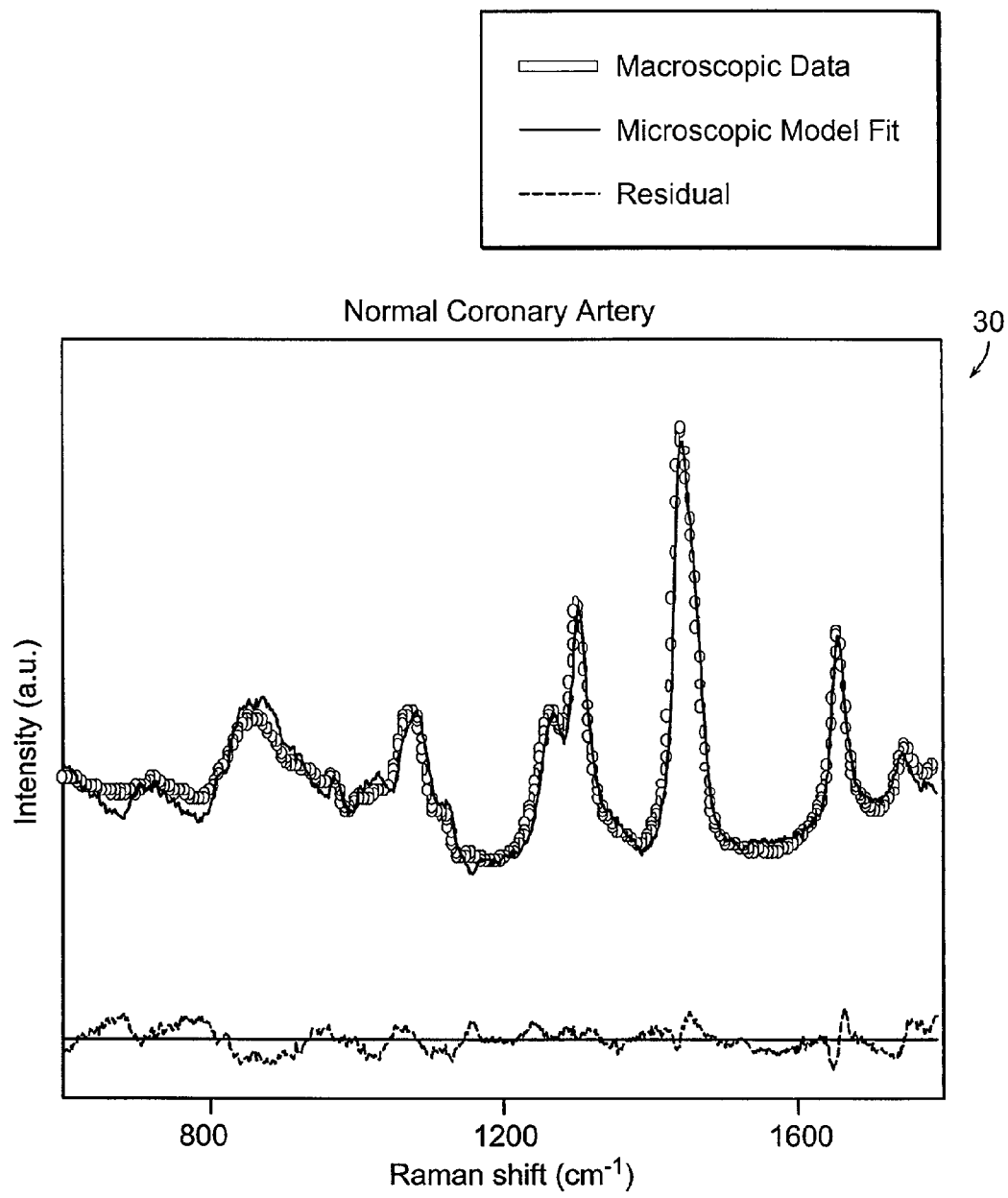
FIGS. 2A-2C are graphical representations of morphological reference data of coronary arteries for a normal coronary artery, non-calcified plaque and calcified plaque, respectively in accordance with a preferred embodiment of the present invention.
Figure 2B:
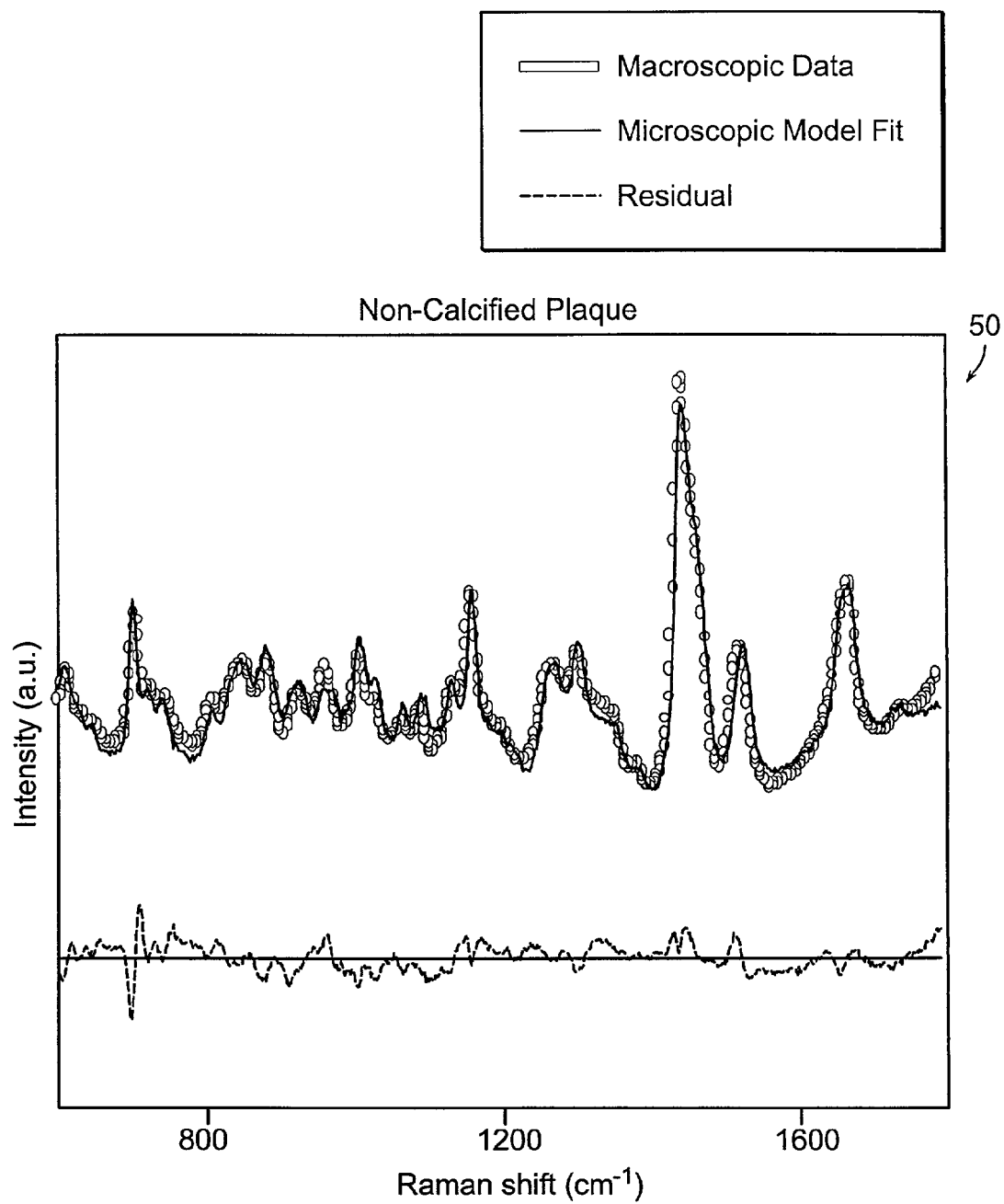
Figure 2C:
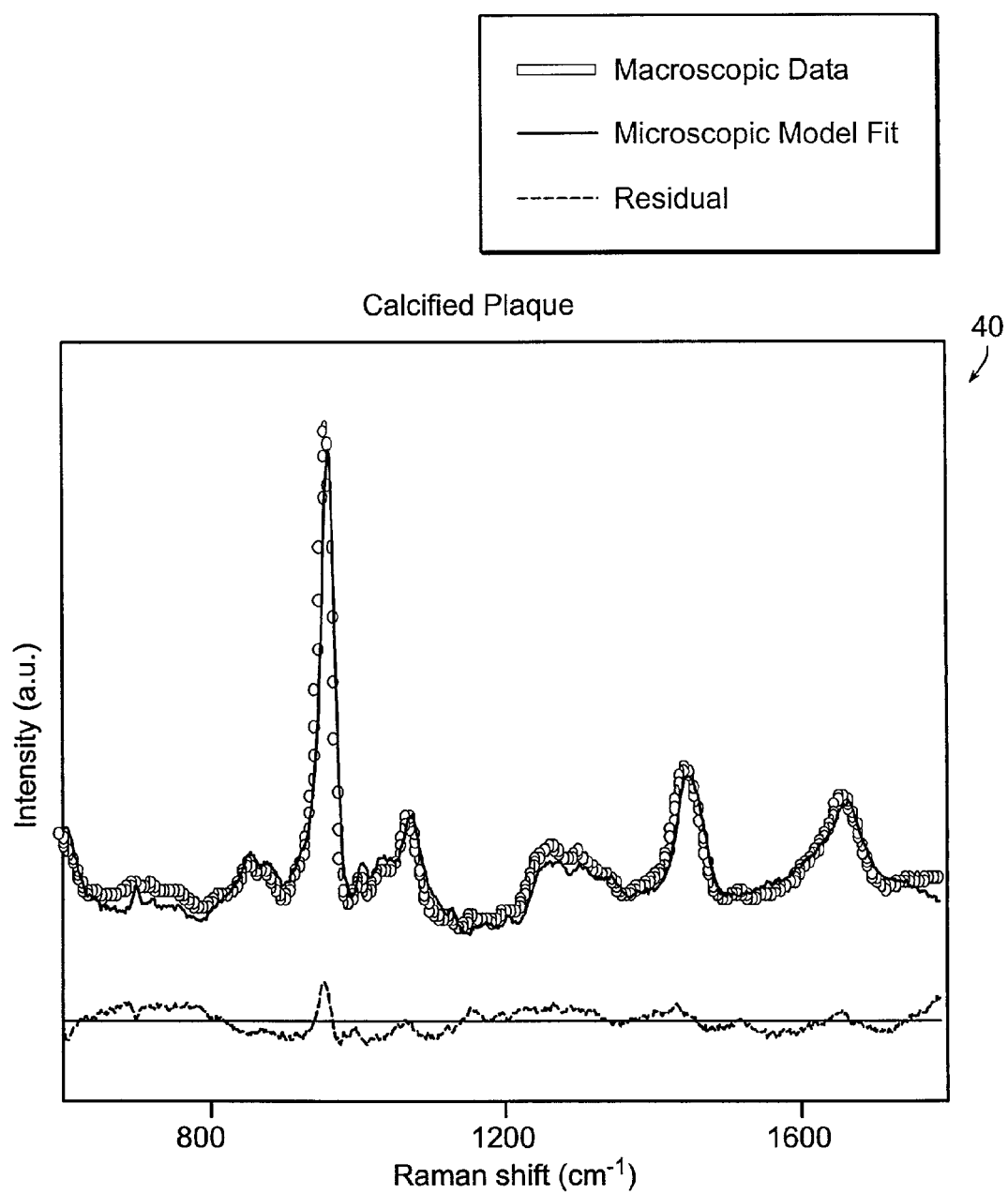

FIGS. 2A-2C are graphical representations 30, 40, 50 of the morphological models and references of the coronary artery in accordance with a preferred embodiment of the system. The studies use biochemical composition in determining plaque stability and plaque progression. The morphological factors are discussed in "Raman microspectroscopy of human coronary atherosclerosis: Biochemical assessment of cellular and extracellular morphologic structures in-situ" by Hendrik P. Buschman et al, as published in Cardiovascular Pathology 10 (2001) 69-82 and "Diagnosis of human coronary atherosclerosis by morphology-based Raman spectroscopy" by Hendrik P. Buschman et al, as published in Cardiovascular Pathology 10 (2001) 59-68, the entire teachings of which are incorporated herein by reference.

Figure 3:
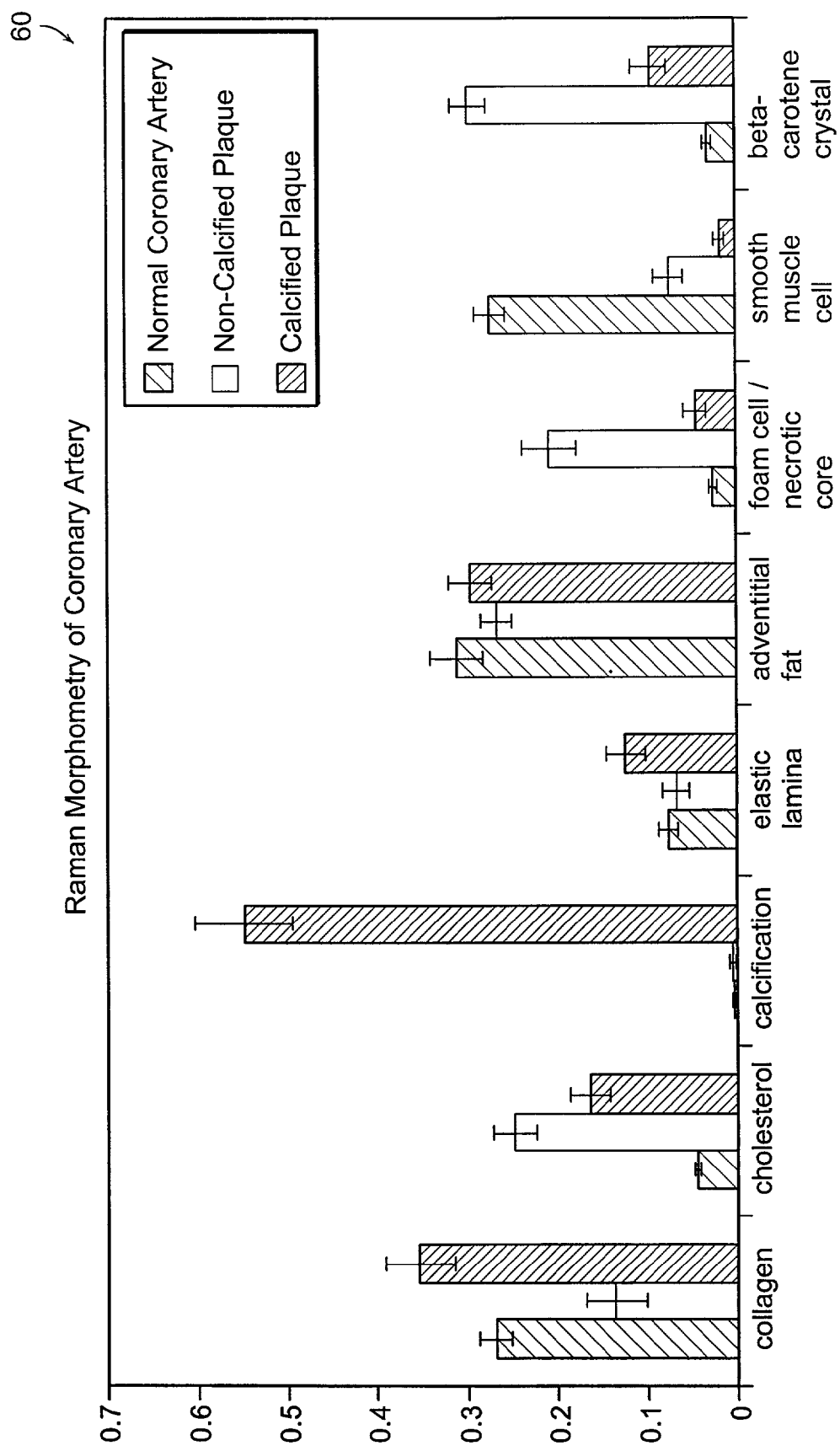
FIG. 3 is a graphical illustration of Raman morphometry of a coronary artery in accordance with a preferred embodiment of the present invention.

FIG. 3 is a graphical illustration 60 of Raman morphometry of a coronary artery in accordance with a preferred embodiment of the present invention. The relative fit coefficients are plotted against different conditions in the normal artery, artery having non-calcified plaque and calcified plaque.

In accordance with preferred embodiments for intravascular applications all of the parameters such as, for example, but not limited to optical filtering and high-throughput optics designed to collect from diffuse sources is accomplished without increasing the diameter of the tip, or compromising its flexibility. Many prior art commercial probes are designed to be used with 785 nm excitation. The methods of the present invention include the recognition that the fluorescence background generated in tissue with 785 nm excitation is at least four times greater than that generated with 830 nm excitation. Operating at 785 nm necessitates longer data acquisition times that is prohibitive for in-vivo applications. The longer the wavelength of operation, the better in terms of fluorescence background. In a preferred embodiment, the use of 830 nm is governed by the fundamental long wavelength limit (1100 nm) of the silicon based charge coupled device (CCD) detectors which is governed by the silicon band gap. Alternate preferred embodiments, can use 785 nm or 1064 nm excitation light with appropriate detector technology.

A preferred embodiment of the present invention includes an optical fiber Raman probe which removes the optical fiber background, limits the length of the rigid distal tip to less than a few mm and the diameter to about two mm, for example, to facilitate use in coronary artery catheterization, employs 830 nm excitation and, maximizes signal collection from diffuse sources in order to allow data collection times of a few seconds or less.

A preferred embodiment includes a rod and tube configuration in which the rod and tube of optical filter modules are coated separately which is easier than coating a single disc having two separate coatings: one in the center to filter the excitation light, and one at the edges to filter the collected light. These embodiments are preferable to coating individual fibers because the filter can adhere better due to the increased surface area. In addition, a two-tone disc is preferable to coating a single disc because it is difficult to deposit concentric coatings on a small diameter with a smooth circular interface without gaps or overlapping regions. Further, it is difficult to place three meter fiber lengths in deposition coating chambers. Each filter can include a stack of dielectric thin films. Such thin film filters can be fabricated by Research Electro-Optics Inc., Boulder, Colo.

FIGS. 4A-4B show a longitudinal and transverse view, respectively, of a preferred embodiment apparatus including a Raman probe. The apparatus 70 includes a two piece multiple, for example, dual wavelength micro-optical dielectric filter module for minimizing and preferably eliminating fiber Raman background in the delivery and collection fibers. This module consists of a rod 82 carrying the excitation dielectric filter coating on one plane face, fitted into the tube 78 carrying the collection dielectric coating on one plane face of the tube. Rods and tubes are used in the embodiment that are made of either sapphire or fused silica which are separately coated with their respective filters prior to assembly. The rod is wrapped or coated with a thin sheet of metal 80 to provide optical isolation between the components. The module is then placed at the distal end of the probe between the fiber bundles and a lens system for collimating the light beams having a lens 86 such as, for example, a ball lens. The lens collects light from high angles and a large area effectively overlapping excitation and collection regions. The ball lens can be fabricated and supplied by Edmund Industrial Optics, New Jersey. In a preferred embodiment, sapphire lenses that are coated with anti-reflection coatings and having an appropriate index for angular acceptance, for example, 1.77 is fabricated by MK Photonics, Albuquerque, N. Mex. Although it is expensive to obtain high quality interference filters at this scale, the cost of the filters is independent on the number of pieces coated, thus it is possible to coat many filters at once, thereby reducing the construction cost of each probe. Furthermore, through additional coating runs, the filter size can be adjusted to create smaller diameter probes for various applications. In a preferred embodiment, the filters are deposited on sapphire or quartz rods and tubes for proper registration with fibers.

FIGS. 4C and 4D show a longitudinal and transverse view, respectively, of an alternate preferred embodiment having a paraboloidal mirror disposed in the lens system. The collection angle can be in the range of 0 to approximately 55° with a collection diameter of approximately 1 mm. The paraboloidal mirror collects light from a wider angle and a larger area.

Figure 5:
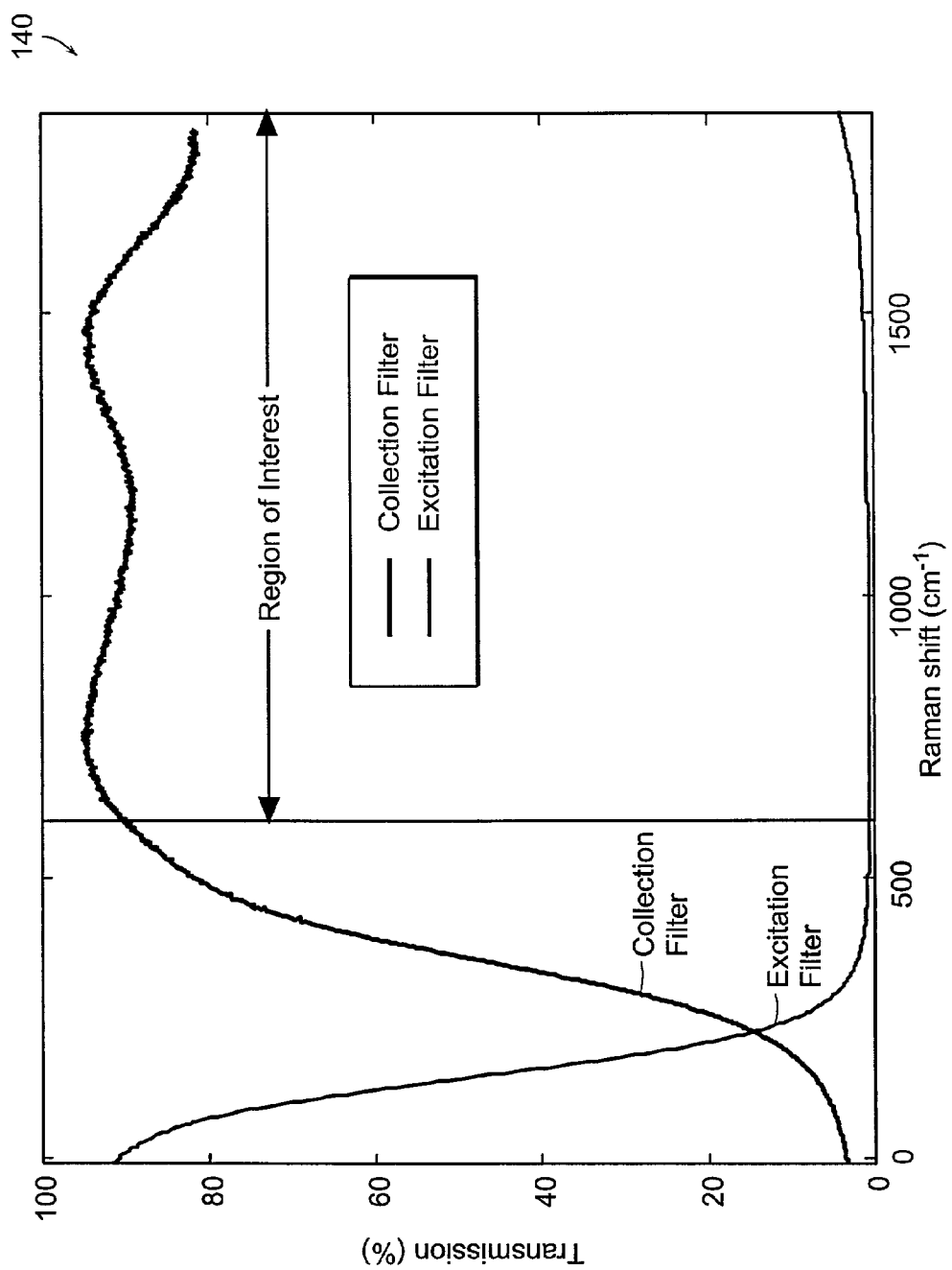
FIG. 5 graphically illustrates the transmission characteristics of the excitation and collection fibers incorporating filters with respect to the Raman shift in accordance with a preferred embodiment of the present invention.

Transmission characteristics of the excitation and collection fibers incorporating these filters are shown in FIG. 5 wherein 0 cm$^{-1}$=830 nm.

In accordance with preferred embodiments, the choice of fiber diameter and numerical aperture (NA), is dictated by the following considerations, for example, that the fiber Raman signal (produces unwanted background) is proportional to the square of the NA, and independent of the fiber diameter, that low NA is better, and that diameter has no effect.

For the excitation fiber, using a lower NA fiber is useful, however there are issues to contend with. At the input end it makes coupling the energy into the fiber more difficult. In a preferred embodiment, when exciting with a laser with a low beam divergence, reasonable care in mounting the fiber and the matching optics avoids this problem. At the output end the beam is more confined. This makes the filter construction simpler and more efficient, but illuminating a larger area in order to minimize the potential of tissue damage due to confining the power of the incident beam to a smaller area (spot) can also be important. However, even a smaller diameter spot of laser excitation light incident on the tissue spreads to cover a larger area typically ½-1 mm diameter because of the aforementioned elastic scattering turbidity, thus mitigating this consideration. In a preferred embodiment a larger diameter fiber, or a distributed array of smaller fibers is used. Preferred embodiments balance the fact that low NA fibers typically exhibit an increased spectral background caused by dopants used in the core and cladding of the fiber to reduce the NA, and hence, use a modest core size and NA for the excitation fiber.

For the collection fibers the situation is different. The Raman energy collected is proportional to the square of the NA. Therefore, from a signal-to-background analysis there is an advantage in using high NA collection fibers the size of which is limited by the spectrograph NA. Here, the best choice of fiber NA and fiber diameter is determined by the spectrometer NA, the desired spectral resolution, and considerations of matching optics, as well as the limitation set by filter acceptance angle. In a preferred geometry, one or a few number of delivery fibers are used as the energy of the laser source can be efficiently coupled into the delivery fiber/fibers. However, a greater number of collection fibers is important to increase the area of collection as shown in FIG. 4B. The area for collection is maximized since it is important to optimize collection of Raman light. Taking all these considerations into account, it is best to use as much of the available cross-sectional area of the optical fiber probe for collection fibers, keeping the number and diameter of the delivery fiber(s) to a minimum.

Preferred embodiments include the following trade-offs. For the spectrometer chosen, the desired resolution determines a slit width. Considering the throughput theorem again, the requirement on the collection fibers is that the product of fiber NA and diameter equal the product of spectrometer NA and slit width. If it is possible to choose a fiber which satisfies the stronger condition that the fiber diameter equals the slit width and the fiber NA equals the spectrometer NA, the necessity of using matching optics is eliminated and the probe can be directly coupled into the spectrometer. If only the product requirement can be satisfied then matching optics are needed. At the output end the collection fibers are arranged in a straight line, which is imaged onto the entrance slit by the matching optics. Occasionally spectrometers use curved slits; the output end of the collection fibers can be modified to match any slit shape. An upper limit on the number of collection fibers is that the height of the fiber array image be less than the slit height or CCD chip, whichever is less. However a smaller limitation may be set by the space available in the collection tip.

In a preferred embodiment, the fiber section of the probe includes a single central excitation fiber with an NA of 0.22 and a core diameter of 200 μm. The buffer of the fiber is matched to the diameter of the excitation filter rod, to facilitate proper fiber/filter registration, and has an aluminum jacket to provide optical isolation from the collection fibers. The 200 μm core diameter collection fibers are arranged in two different geometries in two alternate embodiments. The first embodiment consists of two concentric rings of 10 and 17 fibers for the inner and outer ring, respectively. The second embodiment has a single ring of 15 collection fibers. Although the second design has a slightly reduced collection efficiency, it is more flexible and still able to collect a high SNR spectra in short exposure times. The collection fibers all have an NA of 0.26 so that they are f/#-matched to the spectrograph for optimal throughput as illustrated in FIGS. 4A-4D. The diameter of the probe, in a preferred embodiment is less than 2 mm for access to coronary arteries.

Figure 6:
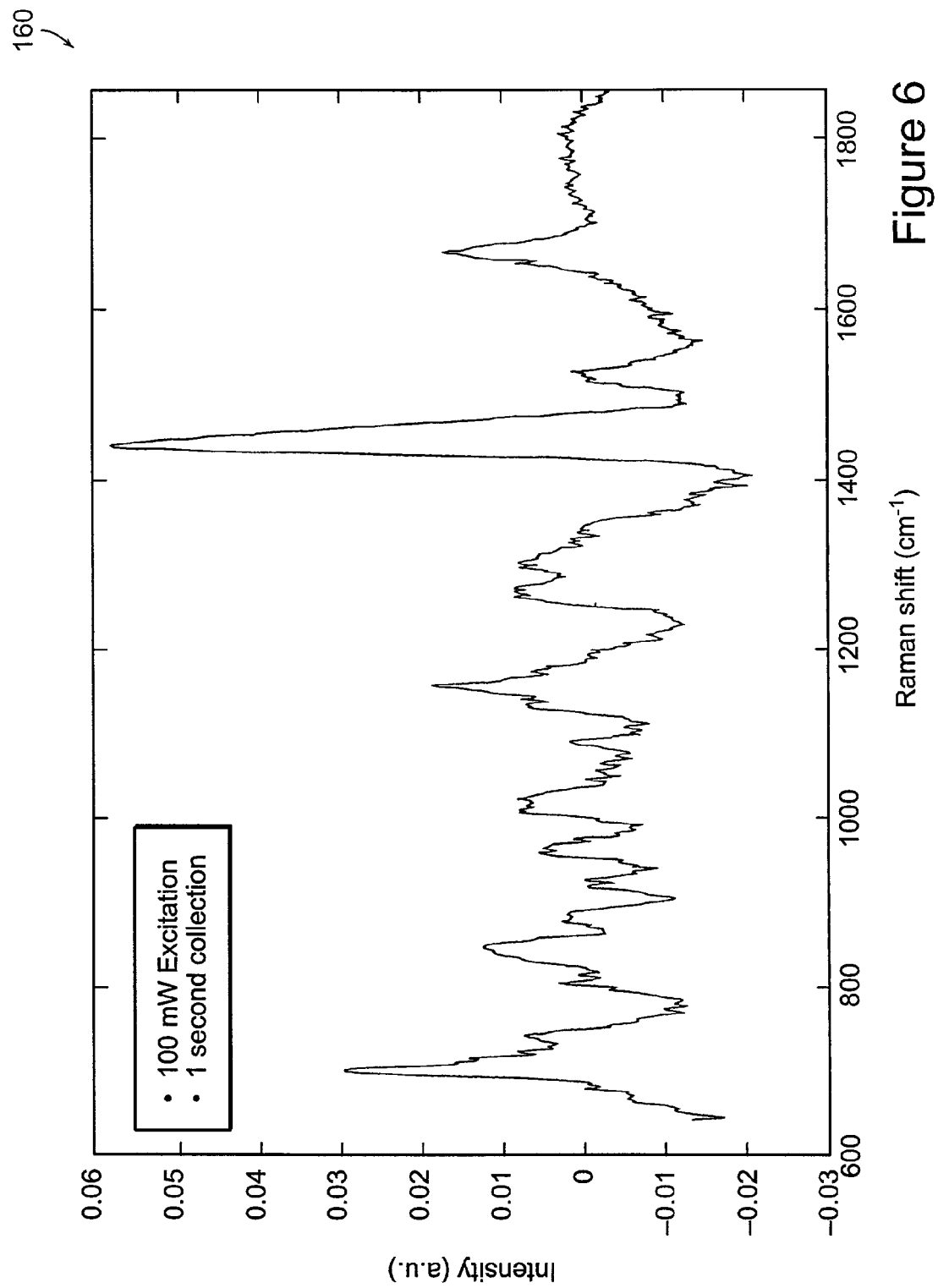
FIG. 6 graphically illustrates the Raman spectrum of a non-calcified artherosclerotic plaque collected in 1 second with 100 mW excitation power in accordance with a preferred embodiment of the present invention.
Figure 7:
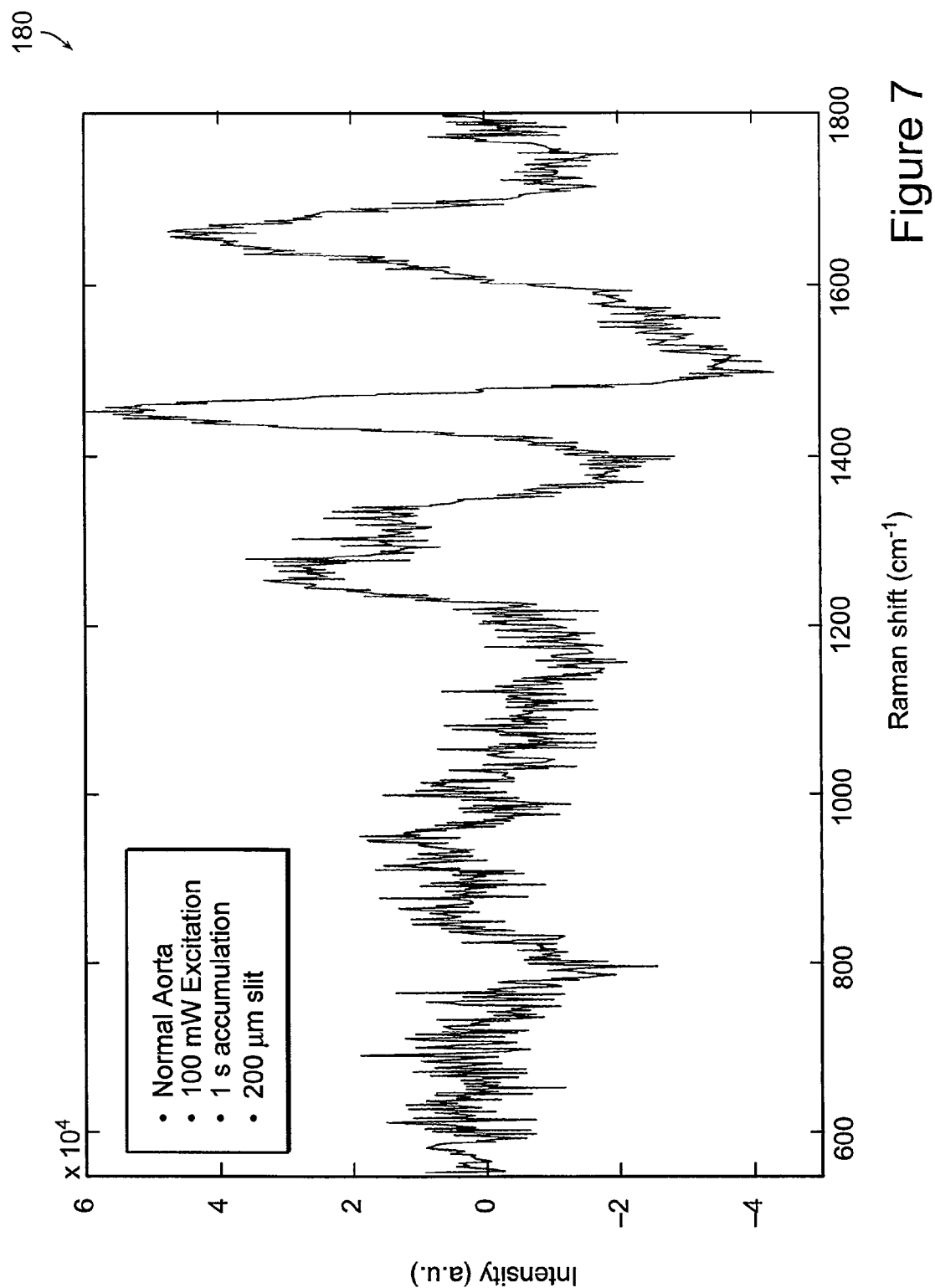
FIG. 7 graphically illustrates the Raman spectrum of a normal artery in accordance with an in-vitro system preferred embodiment of the present invention.

A preferred embodiment provides flexibility with respect to the particular choice of optics for high-throughput collection so that a variety of optical elements can be used to collect the desired AΩ-product. In a preferred embodiment, a ball lens provides highly efficient collection for front viewing optical fiber probes that closely match calculated collection over a radius of 0.35 mm for blood tissue (0.4 mm for artery tissue) while still collecting over large angles as shown in FIGS. 1A-1B and 4A-4B. Collection efficiencies greater than 30% are achieved if a small space is maintained between the sample and lens, greater than 10% when in contact with tissue, the likely and more reproducible in-vivo geometry. An example of the high quality spectra obtained with a preferred embodiment with the probe in contact with tissue is presented in FIG. 6 which shows the Raman spectrum of a non-calcified atherosclerotic plaque collected in 1 second with 100 mW excitation power. In contrast, FIG. 7 shows the spectrum of a normal artery taken with another preferred embodiment system in 10 seconds with the same excitation power.

Figure 8:
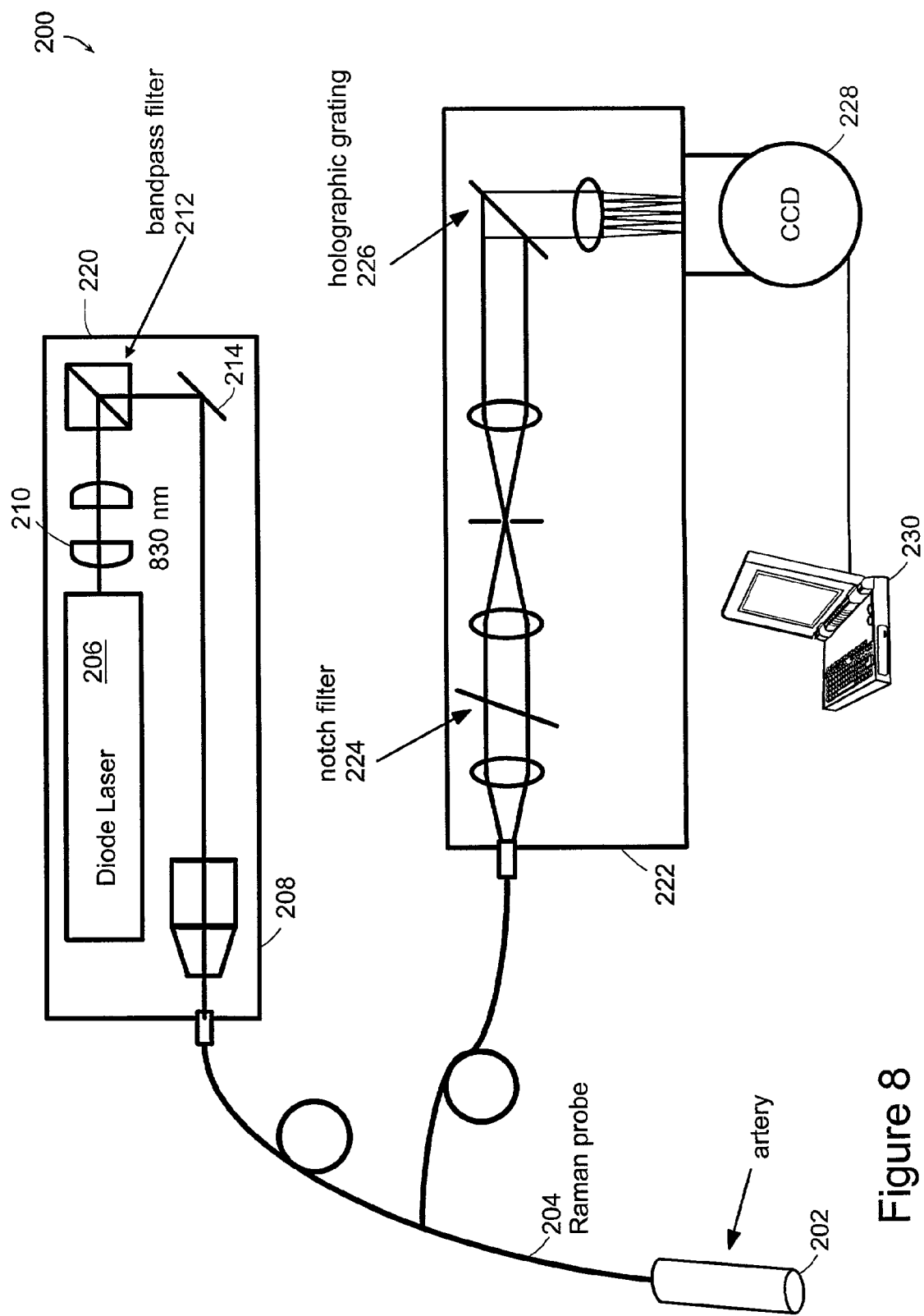
FIG. 8 is a schematic diagram illustrating a system for measuring tissue in accordance with a preferred embodiment of the present invention.
Figure 15:
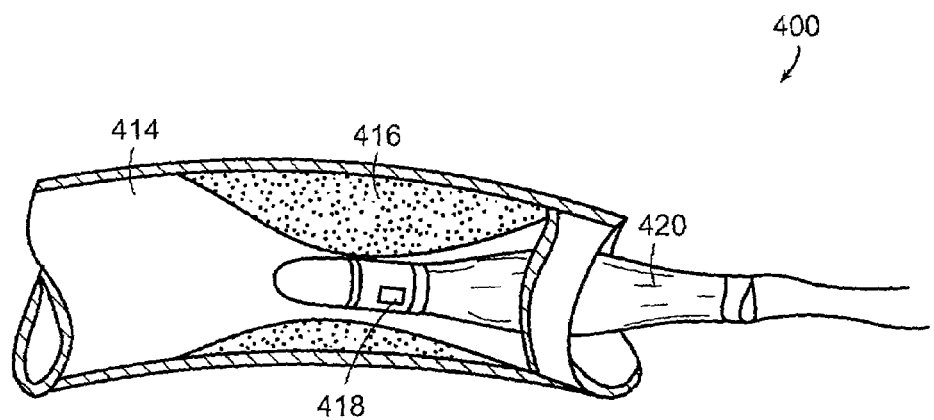
FIG. 15 is partially sectioned view illustrating a portion of a coronary artery showing a probe in accordance with a preferred embodiment of the present invention.

FIG. 8 is a schematic diagram illustrating a system for measuring tissue in accordance with a preferred embodiment of the present invention. A light source 206 emitting at a wavelength longer than 750 nm, such as an argon pumped Ti:sapphire laser system or a diode laser is used. The diode laser may be an InGaAs laser emitting at 785 nm or 830 nm, such as, for example, fabricated by Process Instruments, Salt Lake City, Utah. The laser output is band pass-filtered and is coupled into the delivery optical fibers which are included in the probe 204. The probe 204 is inserted into an artery 202 to diagnose and possibly treat the buildup of, for example, plaque in the artery. FIG. 15 is a partially sectioned view of a portion of coronary artery showing a probe in accordance with a preferred embodiment of the system of the present invention. The system may include a guidewire, and a guide catheter for threading through the large arteries. In a preferred embodiment, in an artery that is partially blocked by fatty material 416, the guide wire is first extended into the artery followed by the catheter which includes the balloon 420. A probe assembly is housed in the tip of the catheter and has a collection window 418. Once the balloon has entered the artery 414, the probe assembly provides a surgeon with a cross-sectional view of the artery. The balloon temporarily blocks blood flow providing a clear field of view, stabilizes the probe and minimizes effects of cardiac motion. Fluoroscopic markers may be used in preferred embodiments. The light is incident on the tissue and Raman-scattered light from the tissue is collected by the collection optical fibers. The collected light is notch-filtered and projected onto an entrance slot of a spectrophotometer. The notch filter removes Rayleigh—scattered laser light. Inside the spectrograph, a grating disperses light onto a CCD detector 228. The CCD interface and data storage and processing is provided in a computer such as a personal computer. A program such as Winspec Software provided by Princeton Instruments can be used to connect the CCD interface to the personal computer which performs the data processing and storage function. In alternate embodiments, the Labview program by National Instruments, Austin, Tex., is used to connect the CCD interface to the personal computer. Raman signals are read from the CCD, collected by the computer and stored on a computer readable media for later analysis or may be used for real time analysis in a clinical setting.

Figure 9:
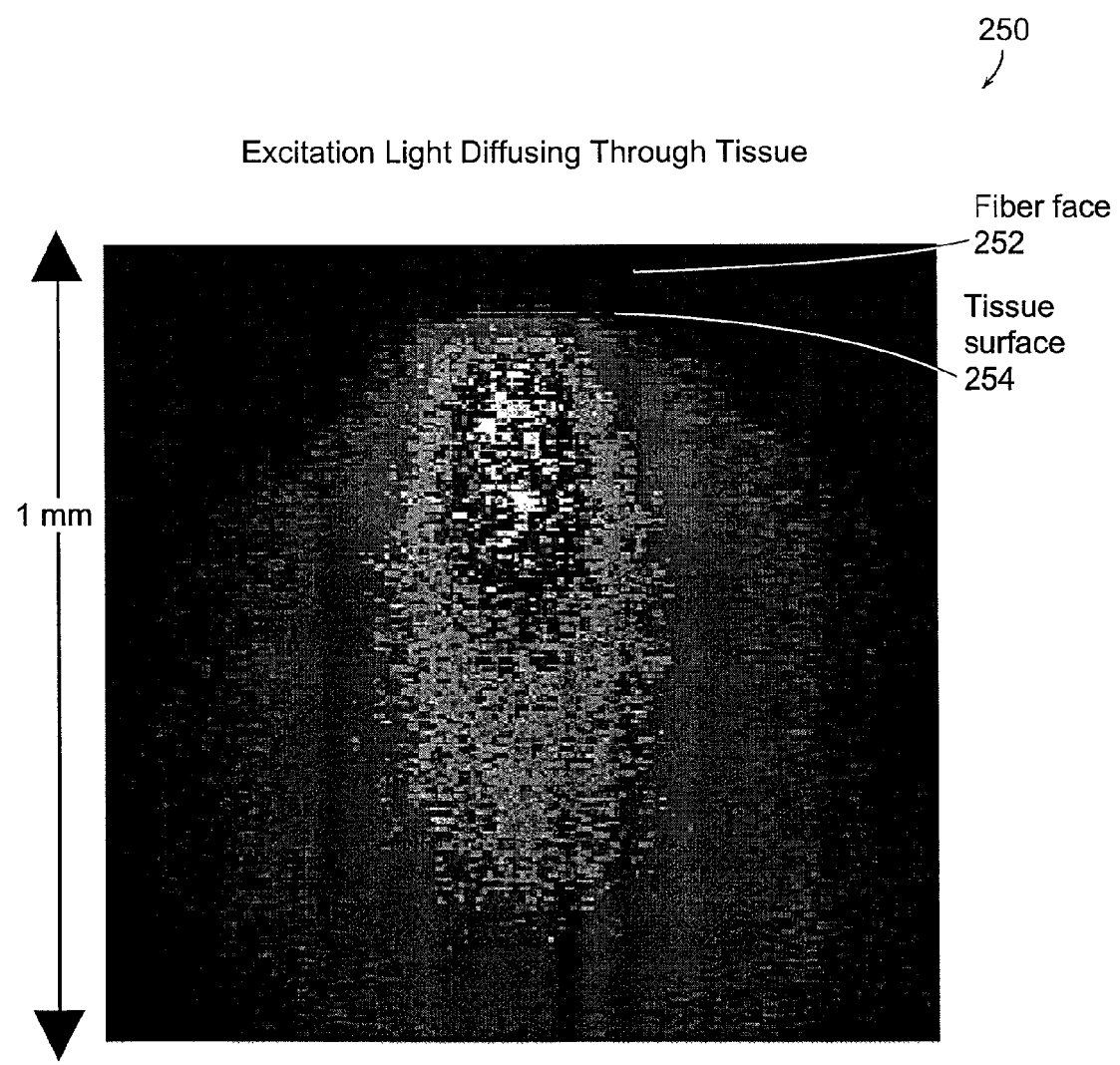
FIG. 9 illustrates the excitation light diffusing through tissue in accordance with a preferred embodiment of the present invention.

FIG. 9 illustrates the excitation light diffusing through tissue in accordance with a preferred embodiment of the present invention. FIGS. 10A-10C are graphical representations of the integrated radial distributions, integrated angular distributions and optimized collection efficiency, respectively, for blood tissue in accordance with a preferred embodiment of the present invention. FIG. 10C illustrates the collection efficiency by varying A and $\Omega$ illustrated in FIGS. 10A and 10B, respectively, but keeping the product A$\Omega$ constant and equal to that of the spectrograph. By the throughput theorem, the étendue is conserved where étendue is the product of area and solid angle. The radial and angular distributions are integrated and their product determines the optimization curve 300. The collection optics are designed to perform at the maximum of the efficiency curve 300. Similar graphical illustrations for artery tissue are provided in FIGS. 38C-38E.

Figure 11:
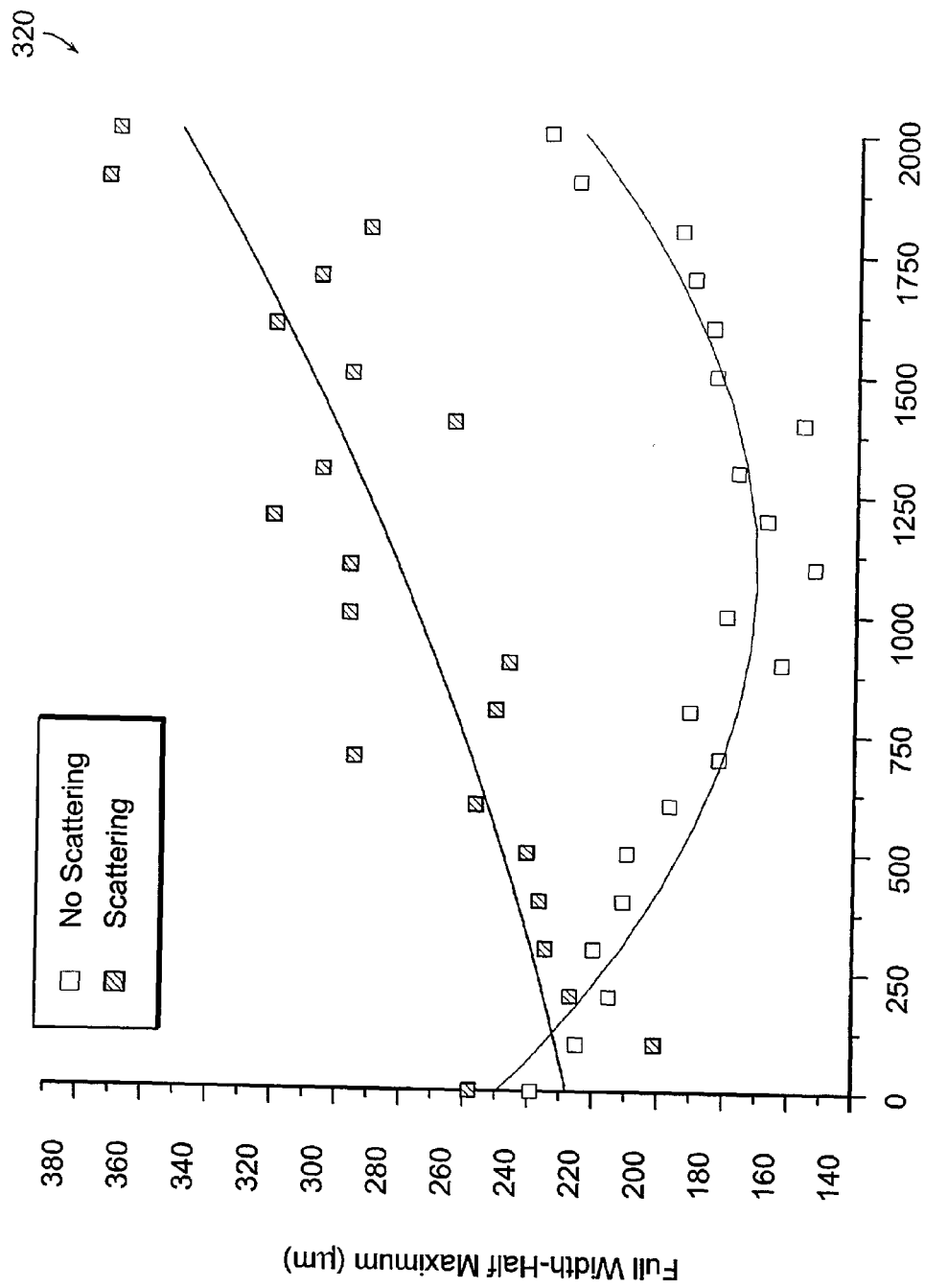
FIG. 11 is a graphical representation of an excitation spot size in accordance with a preferred embodiment of the present invention.
Figure 12:
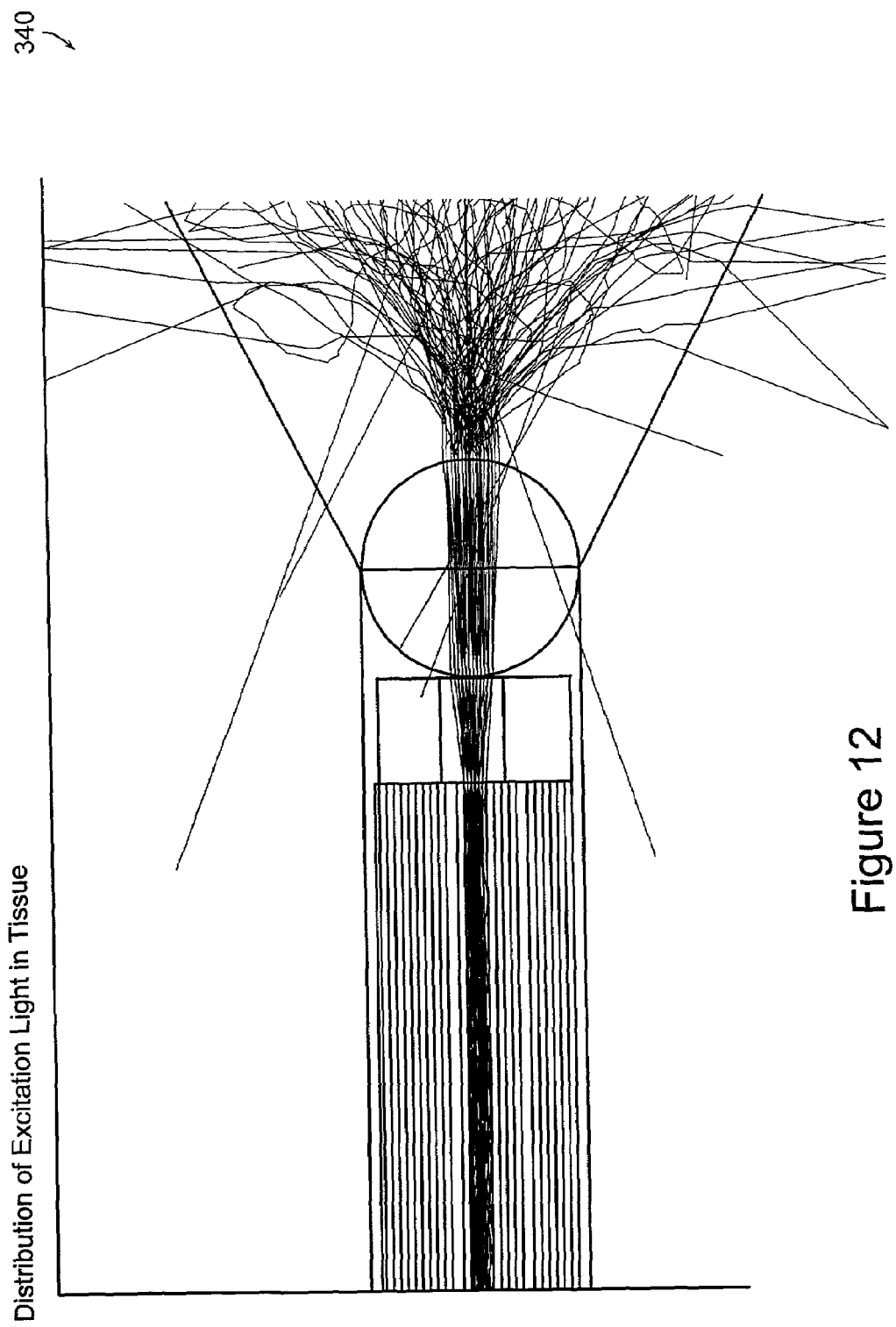
FIG. 12 is an illustration of a ray diagram of the distribution of excitation light in tissue in accordance with a preferred embodiment of the present invention.
Figure 13:
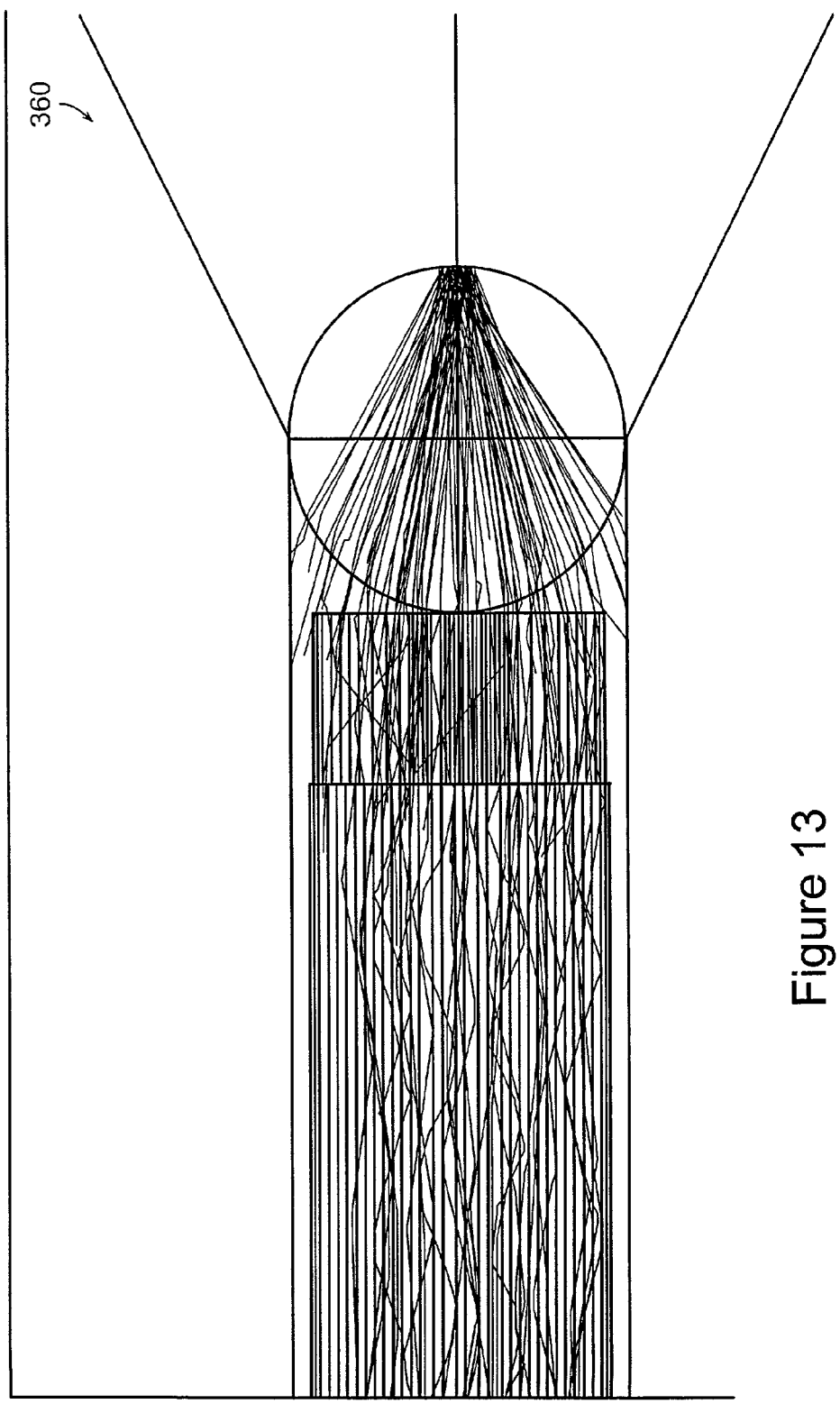
FIG. 13 is an illustration of a ray diagram of the collection efficiency of a probe in accordance with a preferred embodiment of the present invention.

FIG. 11 is a graphical representation 320 of an excitation spot diameter in accordance with a preferred embodiment of the present invention. FIG. 12 is an illustration of a ray diagram 340 of the distribution of excitation light in tissue in accordance with a preferred embodiment of the present invention. FIG. 13 is an illustration of a ray diagram 360 of the collection efficiency of a probe in accordance with a preferred embodiment of the present invention.

Figure 14:
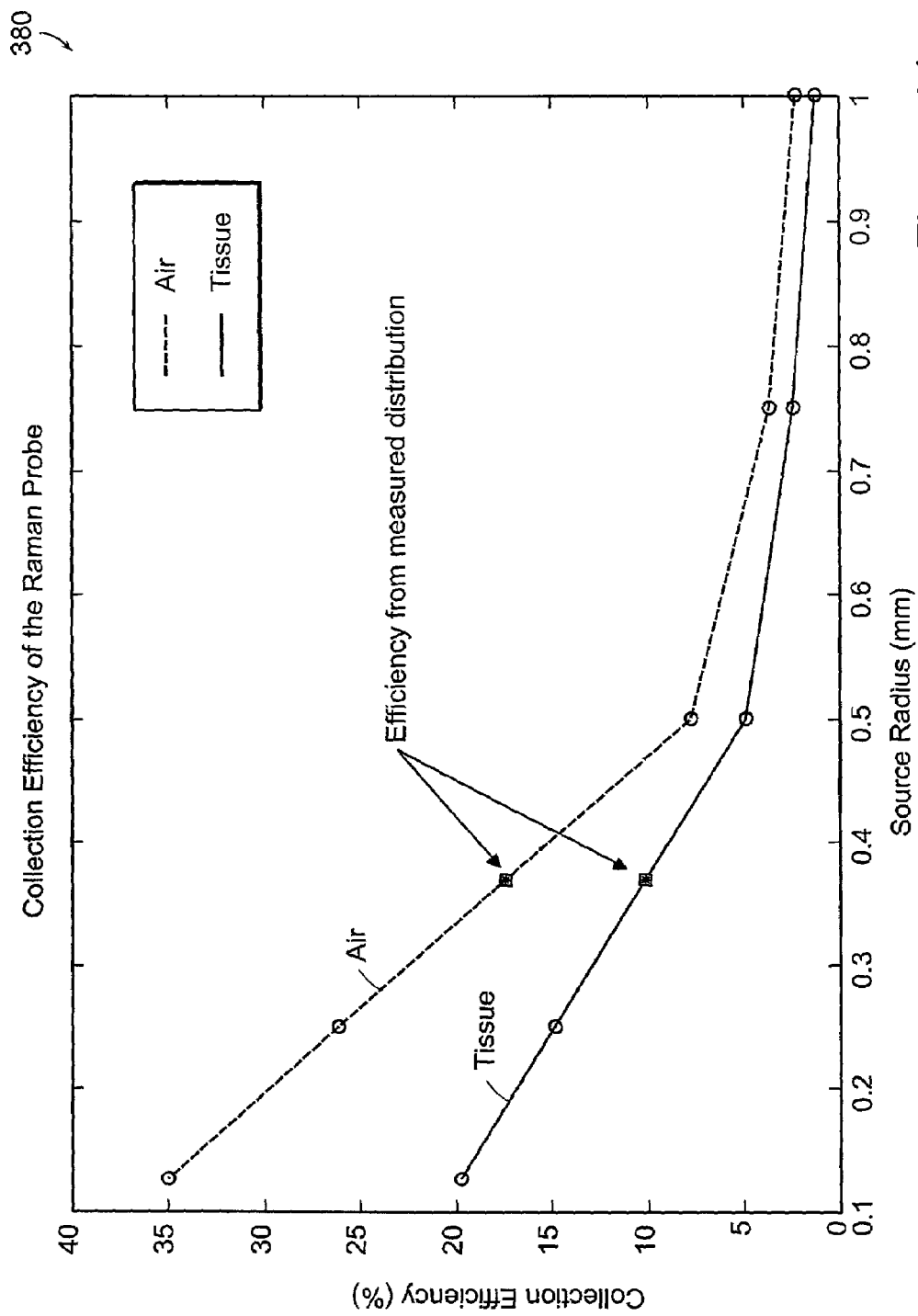
FIG. 14 graphically illustrates the collection efficiency of the probe in accordance with a preferred embodiment of the present invention.

FIG. 14 graphically illustrates the collection efficiency of the probe in accordance with a preferred embodiment of the present invention. The efficiency from a measured distribution for tissue and air is illustrated. All components of the probe are constructed of medical grade materials that can withstand standard cold gas, ethylene oxide sterilization. Alternate sterilization methods as provided by Steris Corporation of Ohio can be used such as, for example, a low temperature sterile processing system. The filter module in the probe tip is assembled and attached to the fiber bundle using high purity sodium silicate as an index matching cement. The advantages of sodium silicate as an index matching cement in Raman spectroscopy are unique and its utility goes beyond the present application. The advantages include producing no interfering Raman spectrum, having an index of refraction close to that of fused silica, thereby greatly reducing the reflection losses from mating surfaces, having a low optical absorption in the near IR, so it introduces no appreciable absorption losses, having cementing properties that facilitate the assembly of the small optical components involved, and it is an article accepted in commerce with uses in many industrial applications.

Sodium silicate is a ternary compound, created by mixing various combinations of water, silicon dioxide and sodium hydroxide, in the alternative sodium oxide. The optical and mechanical properties of the end product can be adjusted by varying these ratios. The other alkali silicates have similar properties, for example, lithium silicate, potassium silicate and can also be used in certain applications.

It is important not to have any adherents between the ball lens and the filters so that there is no index matching that can compromise the lensing effect provided by the curvature of the lens. The lens is secured with a crimped retaining sleeve and sealed with medical grade epoxy to prevent fluid from leaking into the probe tip in accordance with a preferred embodiment of the present invention.

The modular nature of the preferred embodiment probe is very versatile and can accommodate many optical embodiments. Additional embodiments for side-viewing probes as well as other front viewing embodiments for alternate applications are included in the systems of the present invention. For example the use of an angled and mirrored ball lens, a prism, or a micro-optical paraboloidal mirror allows efficient side-viewing probes. A tapered tip allows incorporation into needle probes for optical breast biopsies and a slightly smaller diameter in an alternate preferred embodiment allows breast analysis through ductoscopy. Other potential uses are for skin analysis, transcutaneous blood analyte monitoring, and gastrointestinal cancer evaluation.

Figure 16:
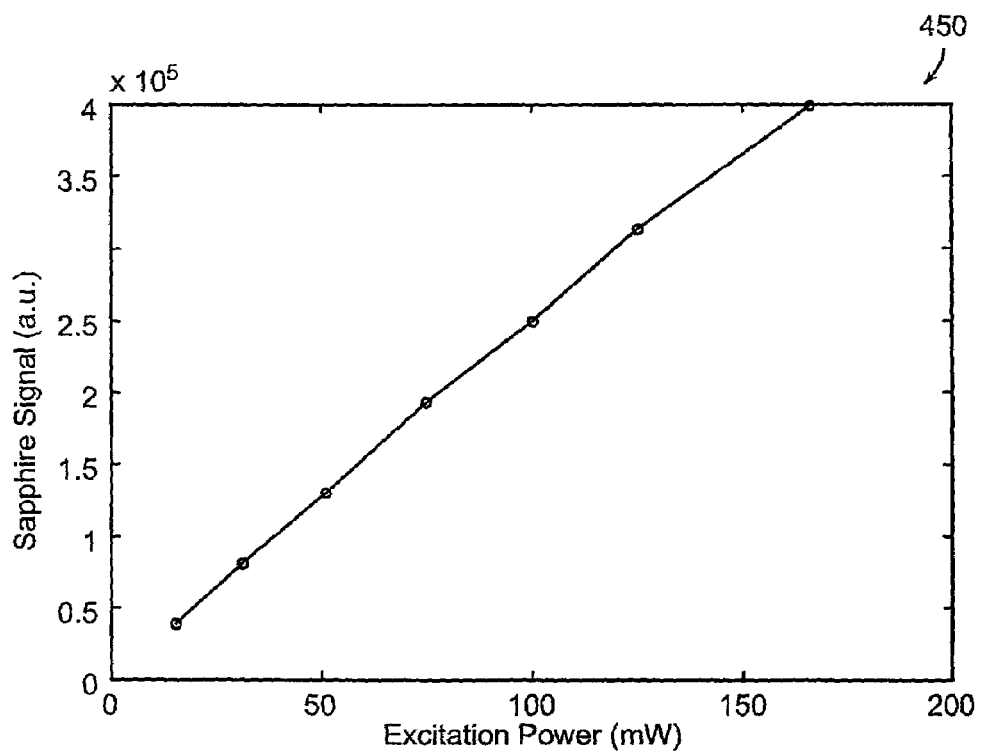
FIG. 16 illustrates a signal from a ball lens as a function of laser power in accordance with a preferred embodiment of the present invention.

FIG. 16 illustrates a signal 450 from a ball lens and function of laser power in accordance with a preferred embodiment of the present invention. The front-viewing Raman probe uses a sapphire ball lens to focus the excitation light and to collect the Raman signal from the tissue. The Raman spectrum from the sapphire lens can be used as an internal standard to calibrate collected signals relative to the excitation laser power, thereby obtaining intensity information. This intensity information is not typically exploited in biological Raman spectroscopy, but can provide enhanced diagnostic power. The graphical plot is generated using data taken with a preferred embodiment Raman probe and a clinical Raman system and represents the magnitude of the signal from the sapphire lens as a function of excitation power while the probe is held in the air. It is indicative of a natural internal standard for measuring power delivered to tissue using a preferred embodiment of the present invention.

Figure 17:
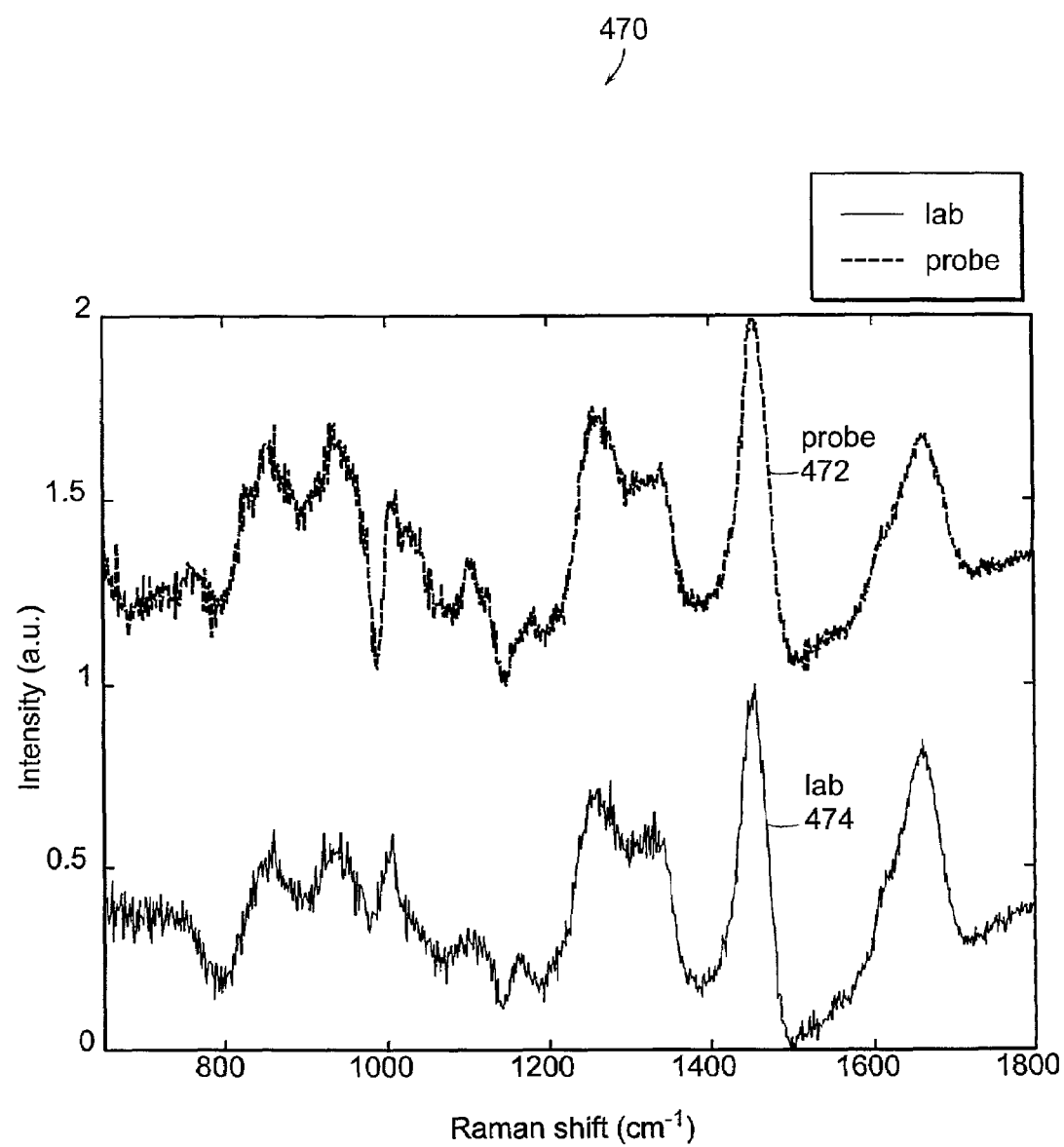
FIG. 17 graphically illustrates a comparison of data as collected using a probe and an experimental system of a normal aorta in accordance with a preferred embodiment of the present invention.

FIG. 17 graphically illustrates a comparison of data from a normal artery collected using a preferred embodiment probe 472 and an experimental system 474. To demonstrate and verify the function of the Raman probe, similar types of tissue are examined. It is demonstrated that similar spectra are obtained, and the signal-to-noise ratio (SNR) of the spectra is also examined, which is an indication of system performance as greater SNR translates to a system having less noise and indicates better performance.

Figure 18:
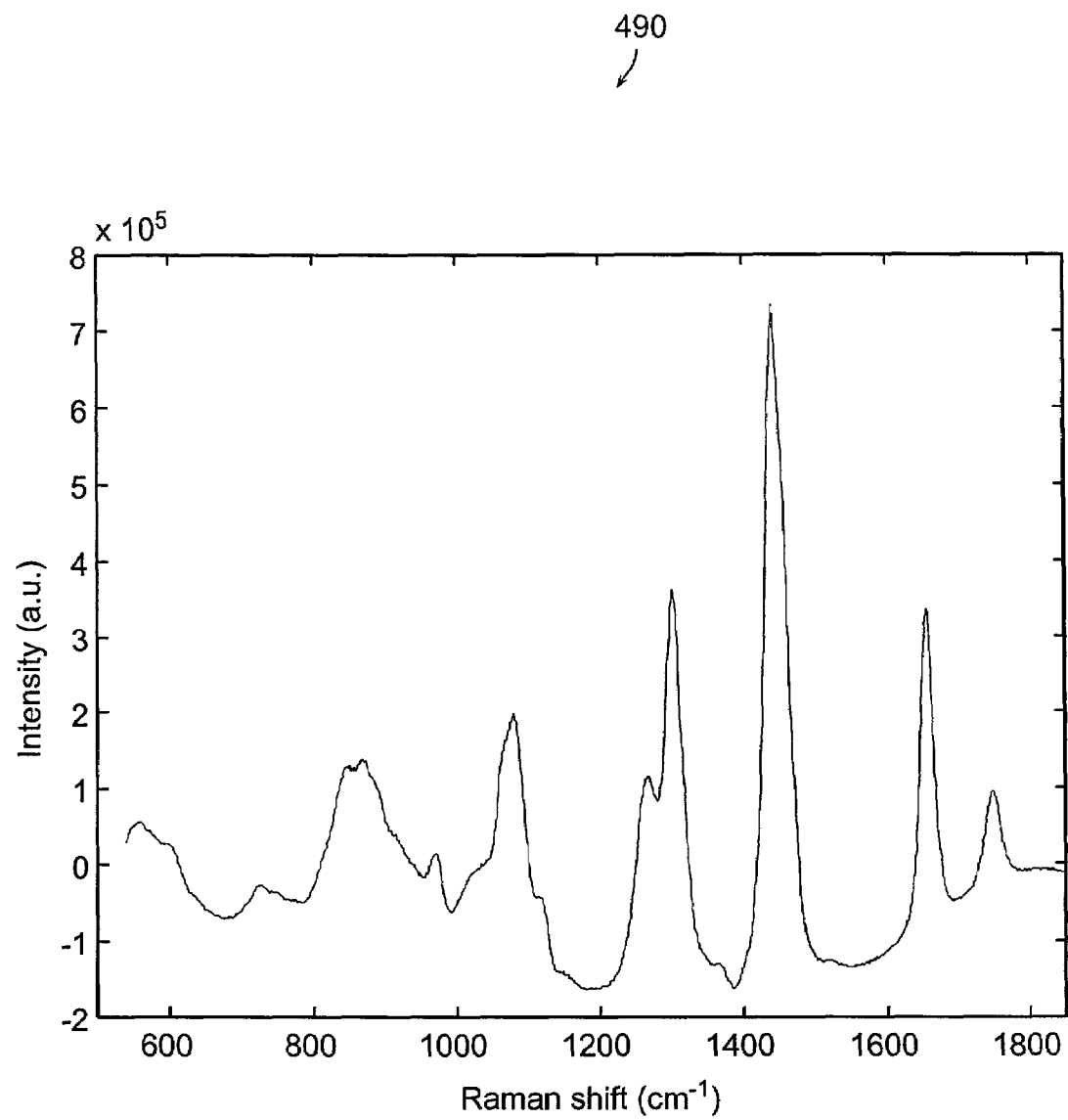
FIG. 18 graphically illustrates a Raman spectrum of normal breast issue examined with a probe in accordance with a preferred embodiment of the present invention.

FIG. 18 graphically illustrates a Raman spectrum 490 of normal breast tissue examined with a probe in accordance with the present invention. Tissues other than an artery have been examined to demonstrate that the probes have multiple uses for disease diagnosis. The probes can be used in ductoscopy procedures for early diagnosis of breast cancer.

Figure 19:
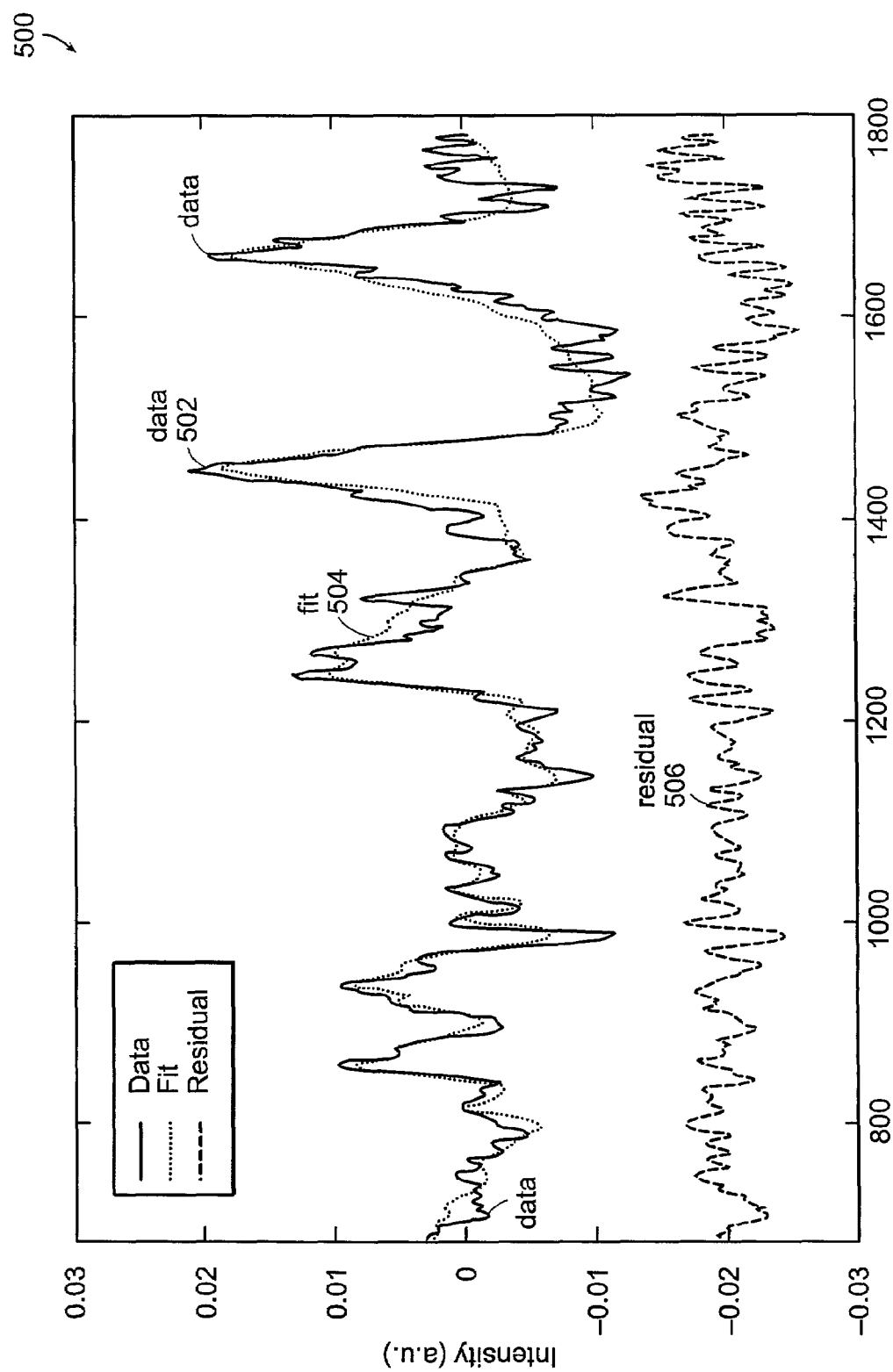
FIG. 19 graphically illustrates a comparison of Raman spectra of a malignant breast tumor as collected using a probe in accordance with a preferred embodiment of the present invention and as predicted by reference data of the present invention.

FIG. 19 graphically illustrates a comparison of Raman spectra of a breast tumor which is diagnosed as being malignant in accordance with a preferred embodiment of the present invention and as predicted by reference data of the present invention. The data 502 as collected using a preferred embodiment probe is compared to data 504 generated by reference data. The reference data coefficients are tabulated in Table 1.

TABLE 1

| Component | Coefficient (%) |
|---|---|
| Calcium oxalate | 11 |
| Calcium hydroxyapatite | 14 |
| Cholesterol | 2 |
| Water | 0 |
| β-carotene | 0 |
| Fat | 15 |
| Collagen | 45 |
| Nucleus | 0 |
| Cytoplasm | 12 |

Figure 20:
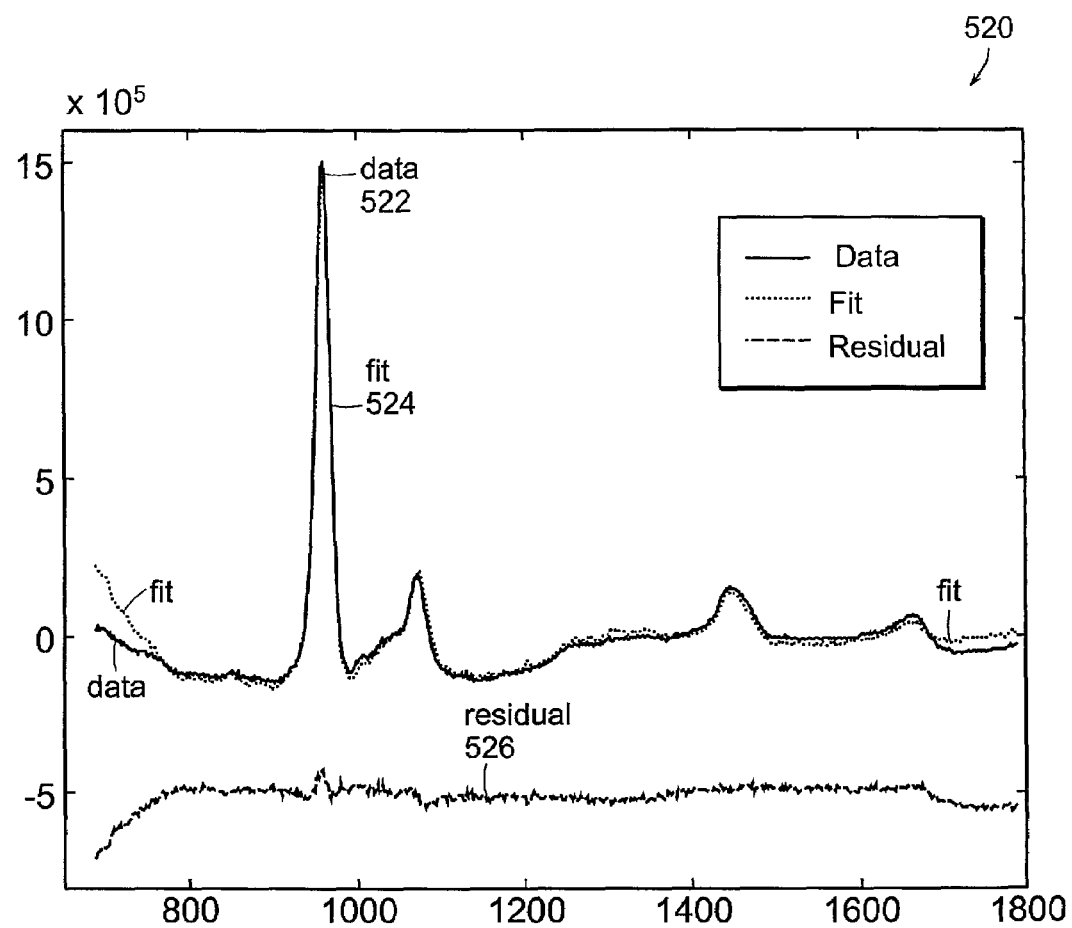
FIG. 20 graphically illustrates a comparison of morphological reference data to calcified aorta data collected with a probe in accordance with a preferred embodiment of the present invention.

FIG. 20 graphically illustrates a comparison of morphological reference data to calcified aorta data collected using a probe in accordance with a preferred embodiment of the present invention. FIG. 20 illustrates the Raman spectrum 522 of a calcified aorta obtained with the Raman probe and a clinical Raman system in 1 second with 100 mW excitation power. A fit with morphological reference data is shown as spectrum 524. The residual spectrum 526 is plotted below on the same scale. The lack of features in the residual indicate a high level of agreement between the observed data and referenced data, proving that the reference data in accordance with preferred embodiments of the present invention developed with the experimental in-vitro system can be applied to data taken with the preferred embodiment Raman probes. Also of note is that there are no features corresponding to any probe background in the residual spectrum 526 indicating that any remaining, unfiltered background noise can be accurately removed. Further, the Raman spectra obtained from diseased artery does not diffuse as much in comparison to spectra obtained from normal artery, thus providing a spectra with a better level of signal-to-noise ratio (SNR). It should be noted that the SNR is affected by both Raman cross-sections of the tissue and the distribution of light.

In a preferred embodiment, the non-axial Raman probe in accordance with the present invention for use in diagnosing atherosclerosis is incorporated in a catheter of the type used for angiography, for example. It includes a balloon for displacing blood and other fluids and to position the catheter in the artery. A preferred embodiment includes a channel for balloon inflation. Further, the catheter system includes the capability for flushing away the blood temporarily with a fluid, for example, saline. One or several optical fibers can be configured so as to direct excitation light in a non-axial direction, either to the side or at an angle ranging from 45°-90°. In such a preferred embodiment a balloon disposed on the side is used to contact the fibers adjacent the artery wall, and displace blood or other intervening fluids.

Alternately, the delivery fibers can be arranged to direct light in a circular pattern at an angle to the axis of the probe. The different collection fibers collect light simultaneously from different portions of the circumferential region illuminated. In this embodiment, the probe is enclosed in an inflatable balloon which is inflated before light delivery and/or collection to displace blood and other fluids. In preferred embodiments, the balloon is of a type used in arterial applications, such as, for example, angioplasty, and are made of thin material so as to allow excitation light to pass through to the artery wall, and return Raman light generated in the artery wall to pass through the balloon to the collection fibers.

Figure 21A:
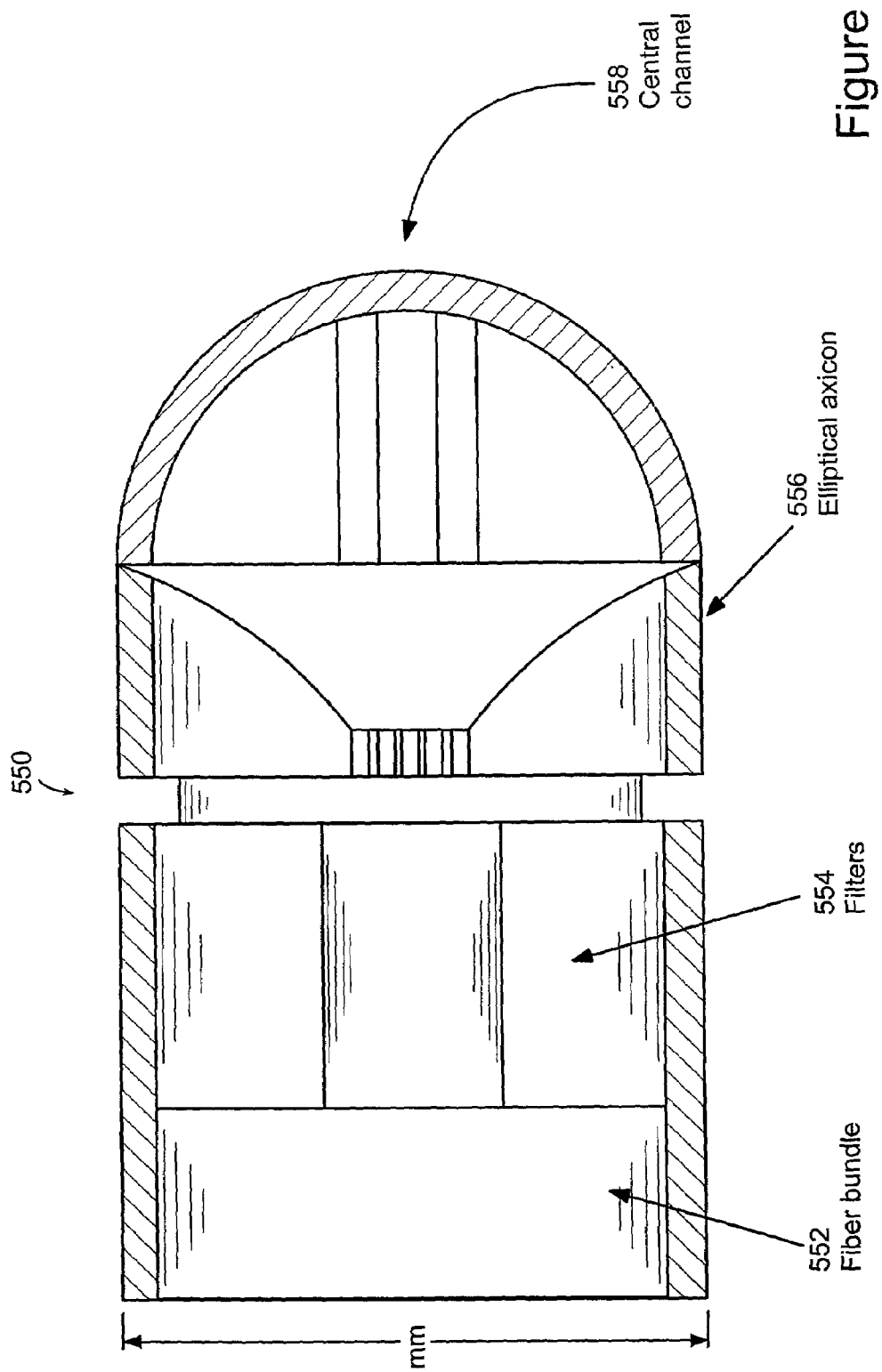
FIGS. 21A-C illustrate longitudinal views of alternate preferred embodiments of side-viewing probes for measuring tissue in accordance with a system of the present invention.
Figure 21B:
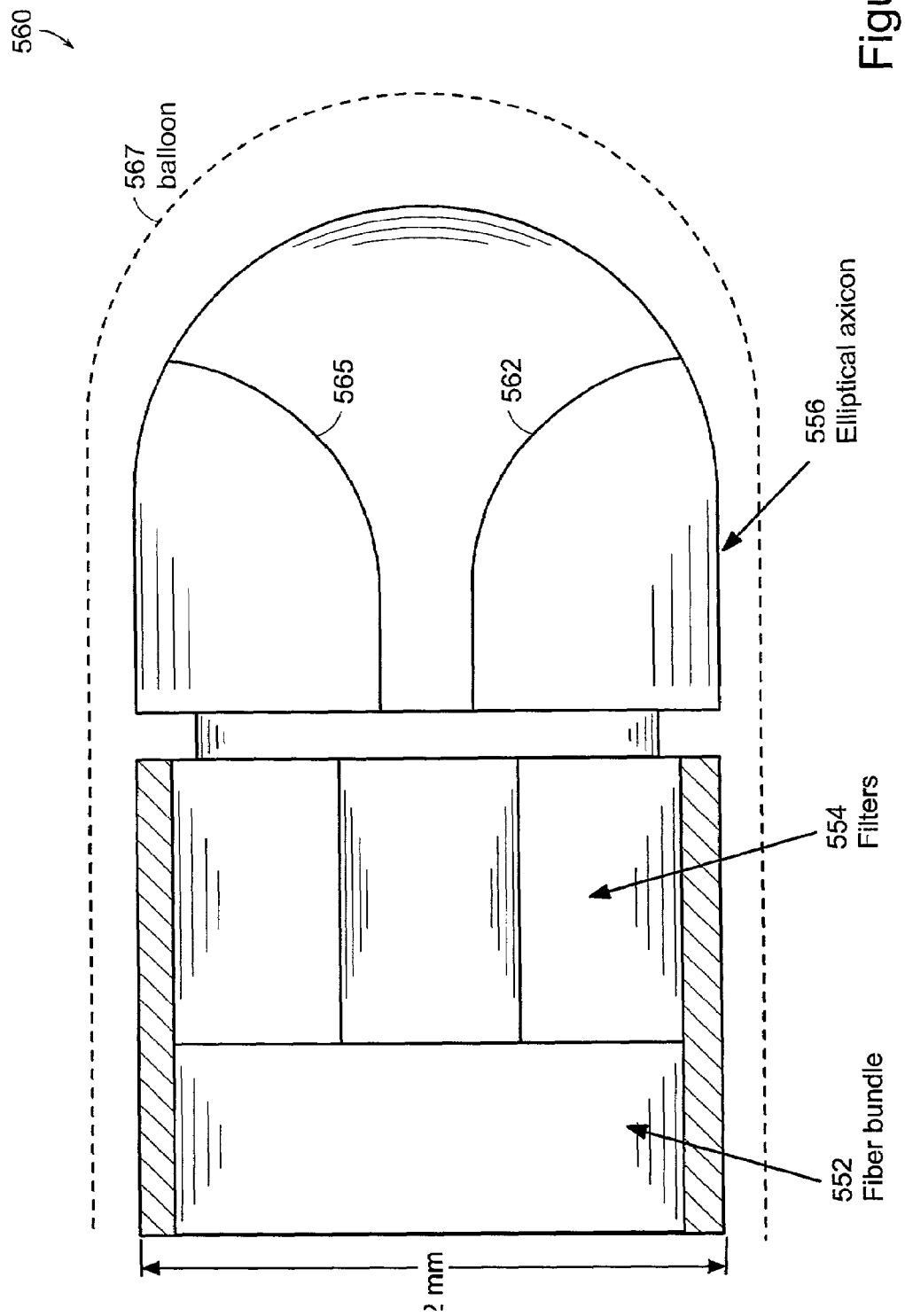
Figure 21C:
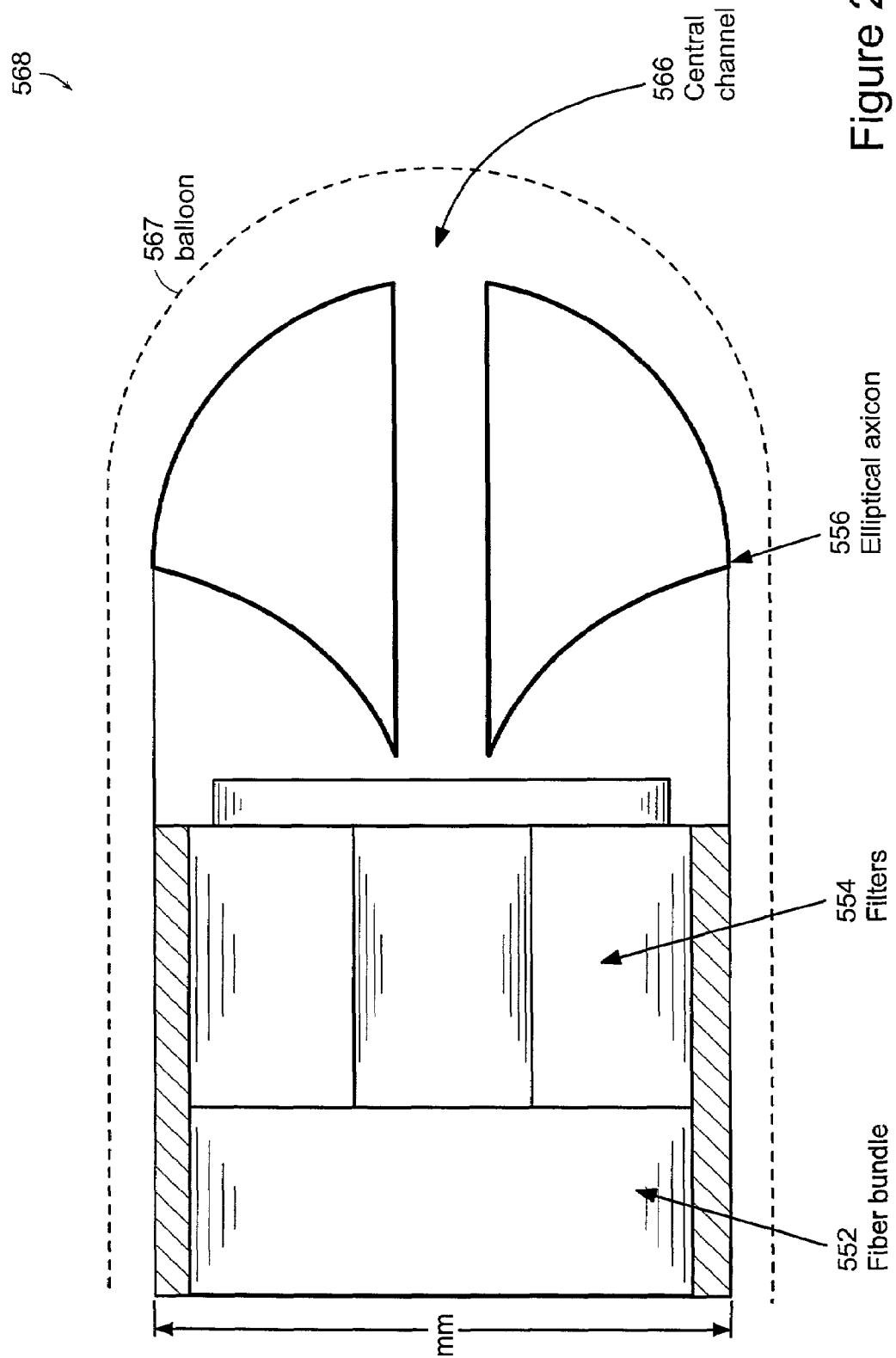

FIG. 21A illustrates a longitudinal view 550 of an alternate preferred embodiment of the side-viewing probe for measuring tissue in accordance with a system of the present invention. The embodiment includes a modified axicon 556 in which the surfaces of the angled sides are made elliptical. FIGS. 21B and 21C are preferred alternate embodiments including at least two different radii of curvature on the angled surface to provide circumferential imaging. Circumferential imaging can be obtained in an embodiment by providing beams ranging from approximately 45°-90° angle and rotating the probe to get a circumferential image. Alternatively, delivery fibers can provide light to the tissue and image, such as, for example, six images are collected in collection fibers to get a circumferential image. In one preferred embodiment, the volume between the filters 554 and the angled portion of the axicon 556 comprises solid glass, preferably sapphire wherein the redirection of light occurs via total internal reflection.

In the alternate preferred embodiment as illustrated in FIG. 21B the angled surfaces 562 of the axicon 556 are mirrored which allow for reflections. The laser light is directed radially or non-axially onto the tissue 564. Further, the surface 565 is elliptical and fabricated using sapphire. The volume between the filters 554 and the axicon 556 may either be filled or empty. This embodiment as illustrated in FIG. 21C provides an open central channel 558, 566 that can be used for flushing fluid, for example, saline into the artery or to inflate a balloon to temporarily block blood flow while data for a spectrum is being acquired. If a central channel 558, 566 is used then the probe includes placing several excitation fibers around the circumference of the central channel. The foci of the axicon can be adjusted. The rod-in-tube geometry of filters described in previous embodiments are modified to a tube-in-tube geometry, i.e., a central tube for the excitation filters with a hole in the middle for the central channel and an outer tube for the collection filters.

Figure 21D:
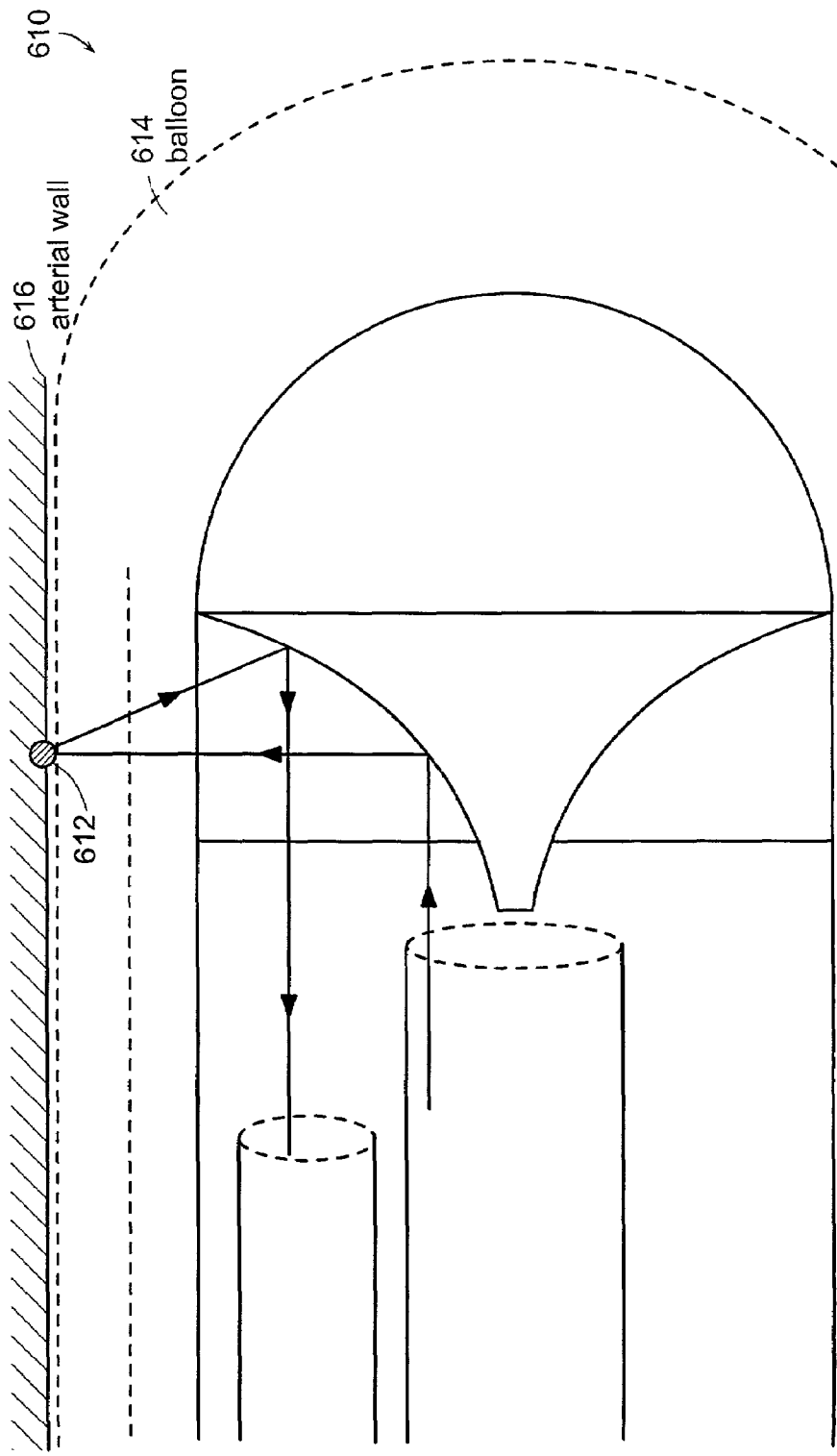
FIG. 21D illustrates a view of a preferred embodiment of a side-viewing probe delivering light imaged onto a portion of tissue and Raman light collected from the tissue in accordance with a preferred embodiment of the present invention.

FIG. 21D illustrates a view of a preferred embodiment of a side-viewing probe, or non-axial viewing probe, and catheter 610 delivering light onto a portion of tissue 612 and Raman light collected from the tissue and reimaged on a point at a second surface in accordance with a preferred embodiment of the present invention. The side-viewing probe includes an inflatable balloon 614 or flexible wire installed adjacent the side-looking element across from its viewing aperture. Upon balloon inflation or wire inflexion, the aperture is pressed into contact with the artery wall 616 displacing blood and/or establishing a well-defined collection geometry.

As discussed briefly hereinbefore, recent studies have shown that chemical composition and morphology, rather than anatomy (degree of stenosis), determine atherosclerotic plaque instability and predict disease progression and the risk of life-threatening complications such as thrombosis and acute plaque hemorrhage. For example, the presence of cholesterol esters may soften the plaque, whereas crystalline-free cholesterol may have the opposite effect. Raman spectroscopy can identify cholesterol esters from free cholesterol as illustrated in FIGS. 35F and 35G. Prior art clinical diagnostic techniques provide accurate assessment of plaque anatomy, but have limited capability to assess plaque morphology in-vivo. Further, prior art diagnostic imaging techniques such as intravascular ultrasound (IVUS), MRI, and angiography provide predominantly anatomic information about the extent of luminal stenosis, but yield only limited information about lesion composition. Coronary angiography, still the "gold standard" for diagnosing coronary artery disease, shows the degree of luminal stenosis, but provides no chemical or morphologic information about the plaque. In fact, unstable atherosclerotic plaques are often "silent" on angiography. IVUS, the most accurate and quantitative technique currently in clinical use, uses the reflection of acoustical waves delivered by an intravascular catheter to probe tissue density and provide imaging information. It has advanced the understanding of atherosclerosis significantly by demonstrating extensive atherosclerosis in coronary arteries that appear normal on angiography. However, although IVUS can identify the presence of an atheroma core, it cannot specifically identify foam cells (FC) or cholesterol crystals (CC) and does not provide any chemical information. MRI has the advantage of being a noninvasive technique, and uses radio waves generated by applying a magnetic field gradient to again probe tissue density and provide imaging information. Like IVUS, it can be used to analyze anatomy and, to a lesser extent, morphology. However, conventional proton MRI techniques used clinically largely ignore and often suppress the chemical shift information. Thus, currently plaque morphology and chemical composition can only be assessed by microscopic examination of excised tissues after endarterectomy or atherectomy.

The preferred embodiment of the present invention includes a method for a morphology-based diagnosis of atherosclerosis in the coronary arteries using Raman spectroscopy that can potentially be performed in-vivo using optical fiber technology. In a preferred embodiment, Raman tissue spectra are collected from normal and atherosclerotic coronary artery samples in different stages of disease progression (n=165) from explanted transplant recipient hearts (n=16). Raman spectra from the elastic laminae (EL), collagen fibers (CF), smooth muscle cells (SMC), adventitial adipocytes (AA) or fat cells, foam cells (FC), necrotic core (NC), cholesterol crystals (CC), β-carotene containing crystals (β-C), and calcium mineralizations (CM) are used as basis spectra in a linear least squares-minimization (LSM) model to calculate the contribution of these morphologic structures to the coronary artery tissue spectra. The preferred embodiment includes a diagnostic sequence of instructions that uses the fit-contributions of the various morphologic structures to classify 97 coronary artery samples in an initial calibration data set as either nonatherosclerotic, calcified plaque, or non-calcified atheromatous plaque. The sequence of instructions correctly classifies 64 (94%) of 68 coronary artery samples prospectively. Raman spectroscopy provides information about the morphologic composition of intact human coronary artery without the need for excision and microscopic examination. Thus, a preferred embodiment uses Raman spectroscopy to analyze the morphologic composition of atherosclerotic coronary artery lesions and assess plaque instability and disease progression in-vivo.

The present invention includes acquiring quantitative morphologic information regarding lesion composition from coronary arteries by Raman spectroscopy using a modification of mathematical reference data. This morphologic information can be used for diagnostic purposes. The chemical and morphologic information obtained by Raman spectroscopy can be the basis of a diagnostic assessment of human coronary artery disease.

In principal, both quantitative chemical and morphologic information regarding atherosclerotic lesion composition can be obtained from the same Raman spectrum. A preferred embodiment of the present invention analyzes coronary artery tissue by modeling of Raman tissue spectra using the spectra of morphologic structures rather than biochemical components as a basis set. Basis spectra for the reference data are obtained from morphologic structures commonly observed in the normal artery wall and in atherosclerotic plaque, including collagen fibers (CF), the internal and external elastic laminae (EL), smooth muscle cells (SMC), adventitial adipocytes (AA) or fat cells, foam cells (FC), necrotic core (NC), cholesterol crystals (CC), β-carotene containing crystals (β-C), and calcium mineralizations (CM). These basis spectra can then be used to linearly fit the spectra of an initial calibration set of coronary artery specimens. Using the fit-contributions of the various morphologic structures, an algorithm is included in a preferred embodiment that classifies the arteries as atherosclerotic or nonatherosclerotic as in a biochemical model. The diagnostic performance of the preferred embodiment can be tested by applying morphology-based reference data, to a second, prospective, validation set of coronary arteries.

In a preferred embodiment, tissue preparation includes obtaining from explanted recipient hearts, within 1 hour after heart transplantation, human coronary artery samples (n=200) from 16 patients, exhibiting different stages of atherosclerosis. Seven patients had heart failure due to dilated cardiomyopathy and nine due to severe ischemic heart disease. Immediately after dissection from the explanted heart, the artery segments were rinsed with neutral-buffered saline solution, snap-frozen in liquid nitrogen, and stored at −85° C. until use. The artery samples were collected in two sets, the first containing 113 (calibration set) and the second, 87 samples (prospective validation set).

These artery samples can be and were used for macroscopic and microscopic Raman spectroscopy studies. For the macroscopic study, the samples (97 and 68, from the first and second sets, respectively) were warmed passively to room temperature, cut open longitudinally, placed in an aluminum holder with the lumen side upwards, and examined under ×10 magnification for selection of the region to be evaluated. After spectroscopic examination, each spot interrogated was marked with a small spot of colloidal ink, and fixed in 10% neutral-buffered formalin.

For the collection of the Raman spectra using a microspectrometer unstained, transverse tissue sections (6-8 µm) were cut from the coronary artery samples. Four sections of each sample were mounted on glass microscope slides and stained for light microscopic examination, whereas serial unstained transverse sections were mounted on $BaF_2$ or $MgF_2$ flats (International Scientific Products, Tarrytown, N.Y. and Spectra-Tech, Stamford, Conn.), kept moist with phosphate buffered saline (pH 7.4), and transferred to the microscopic stage for spectroscopic experiments. No coverslip was used. Under white light illumination, the major morphologic structures were selected and recorded on videotape under ×10 and ×63 magnification.

The formalin-fixed macroscopic tissue samples were processed, paraffin-embedded, and cut through the marked locations in 5-μm thick sections, stained with hematoxylin and eosin, and examined by two experienced cardiovascular pathologists. The tissue sections were classified according to the updated Systemized Nomenclature of Human and Veterinary Medicine (SNoMed). The samples in both the calibration and validation data sets were diagnosed as either (1) normal (n=12 and 1), (2) intimal fibroplasia (n=61 and 25), (3) atherosclerotic plaque (n=3 and 0), (4) atheromatous plaque (n=6 and 16), (5) calcified atherosclerotic plaque (n=1 and 3), (6) calcified atheromatous plaque (n=7 and 13), (7) calcified fibrosclerotic plaque (n=5 and 10), or (8) calcified intimal fibroplasia (n=2 and 0, respectively). Because some of these categories had small sample numbers, the eight categories were condensed into three diagnostic classes for the development of a diagnostic algorithm: Class I, nonatherosclerotic tissue (Categories 1 and 2; n=73 and 26); Class II, noncalcified atherosclerotic plaque (Categories 3 and 4; n=9 and 16); and Class III, calcified atherosclerotic plaque (Categories 5-8; n=15 and 26).

Figure 22:
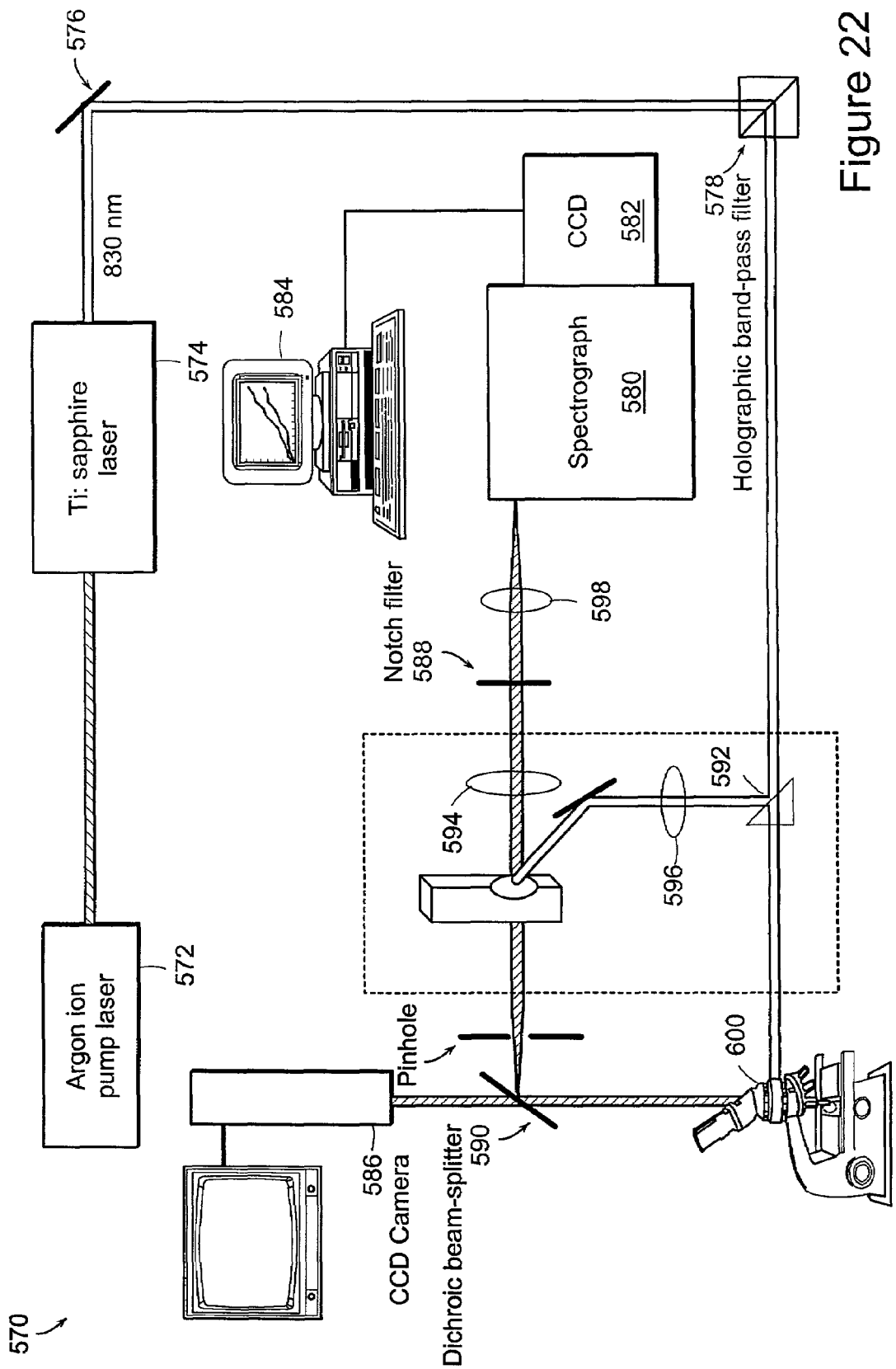
FIG. 22 is a schematic illustration of a combined Raman macrospectroscopy and confocal microspectroscopy system in accordance with a preferred embodiment of the present invention.

The macroscopic and microscopic Raman spectra were obtained using the Raman spectroscopy system shown in FIG. 22. Near-infrared (NIR) laser light (830 nm) is generated by an $Ar^+$-pumped Ti: sapphire laser system 572, 574 (Coherent Innova 90/Spectra Physics 3900S, Coherent, Santa Clara, Calif.). The laser output is band pass-filtered (Kaiser Optical Systems HLBF, Ann Arbor, Mich.) and, by insertion of a prism 578, either projected onto the tissue sample in the macroscopic setup, or projected into a confocal microscope 600 and focused onto the tissue section with a ×63 infinitely corrected water immersion objective (Zeiss Achroplan, NA 0.9). In the macroscopic setup, Raman-scattered light from the tissue (sampling volume 1-2 $mm^3$) is collected with a lens, Notch-filtered 588, and focused onto the entrance slit of a Chromex 250IS/SM spectrophotometer (Chromex, Albuquerque, N. Mex.). In the microscope setup (sampling volume approximately 2×2×2 $\mu m^3$), the Raman light scattered from the tissue is collected with the same objective that is used to focus light onto the sample, passed through a pinhole (giving the system its confocal characteristic), Notch-filtered, and projected onto the entrance slit of the spectrophotometer. Inside the spectograph 580, a grating disperses light onto a deep-depletion CCD detector 582 (Princeton Instruments, Princeton, N.J.) cooled to −110° C. The CCD interface (ST130, Princeton Instruments), along with data storage and processing, is rendered on a personal computer 584.

For the macroscopic measurements, the laser power is 350 mW, and the signal collection time is in the range 10-100 s. For the microscopic measurements, the laser power is 80-120 mW, and the signal collection time is 60-360 s, and the Raman spectra is collected in the range between 400 and 2000 $cm^{-1}$ (resolution 8 $cm^{-1}$).

Each spectrum is frequency-calibrated and corrected for chromatic variations in spectrometer system detection. A fourth-order polynomial is fit to each spectrum and subtracted from the spectrum to correct for remaining tissue fluorescence. The macroscopic tissue spectra can be modeled in the 680-1800 $cm^{-1}$ Raman shift range as a linear combination of the morphologic structure basis spectra by LSM. This Raman shift range is chosen, because this range contains the most spectral information.

The morphologic structure Raman spectra can be normalized with respect to their maximum peak intensity. All spectra in the two data sets can be modeled accurately with the final set of eight morphologic basis spectra. The Raman spectral reference data calculated the fractional fit-contribution of seven of the morphologic structures. The eighth structure, β-carotene, is an intense Raman scatterer that often contributes to coronary artery Raman spectra, but is present only in low concentrations. For this reason, its spectrum is included in the spectral reference, but no fractional fit-contribution is calculated.

In calcified atherosclerotic plaques, CM often occupy large volumes of the tissue examined by Raman spectroscopy. To obtain information about the remaining noncalcified regions, and to compare the morphologic structure fractional fit-contributions among the different disease classes, the spectra of calcified plaques are renormalized, neglecting the contribution of calcium mineralization, and the morphologic structure fractional fit-contributions of the noncalcified regions (denoted by $X_{NCR}$) is calculated.

The relative fit-contribution of each morphologic structure to the spectra in the calibration data set is used to develop the algorithm or sequence of instructions to classify the tissue into one of the three diagnostic classes. The method of logistic regression can be used to generate a discriminant score, $R_1$, based on a linear combination of relative fit-contributions ($C_i$) of each morphologic structure 1 as $R_i=\alpha_i+\beta_{1i}C_1+\beta_{2i}C_2+\ldots$ with $\alpha_i$ being a constant and $\beta_{ji}$ an adjustable coefficient for each morphologic structure. This method is chosen over discriminant analysis, because logistic regression does not make any assumptions about the normalcy of the fit-coefficients.

Using maximum likelihood estimation with an analytical tool, for example, the software package STATA (Release 5.0, Stata, College Station, Tex.), the probability that an artery sample j is nonatherosclerotic ($P_{jI}$), or contains a noncalcified atherosclerotic plaque ($P_{jII}$), or contains a calcified atherosclerotic plaque ($P_{jIII}$) is determined as $$P_{jI} = \frac{1}{1+e^{Rj1}+e^{Rj2}} \tag{1}$$

$$P_{jII} = \frac{e^{Rjt}}{1+e^{Rj1}+e^{Rj2}}, \text{ and } P_{jIII} = 1 - P_{jII} - P_{jI} \tag{2}$$

which sum to one. Furthermore, using a likelihood-ratio test on the initial calibration data set, it can be determined which morphologic structure relative fit-contributions are significant for diagnosis, and what diagnostic thresholds for these relative fit-contributions correctly classify the most samples. The algorithm so developed can then be used to prospectively classify the artery samples in the second validation data set.

Figure 23:
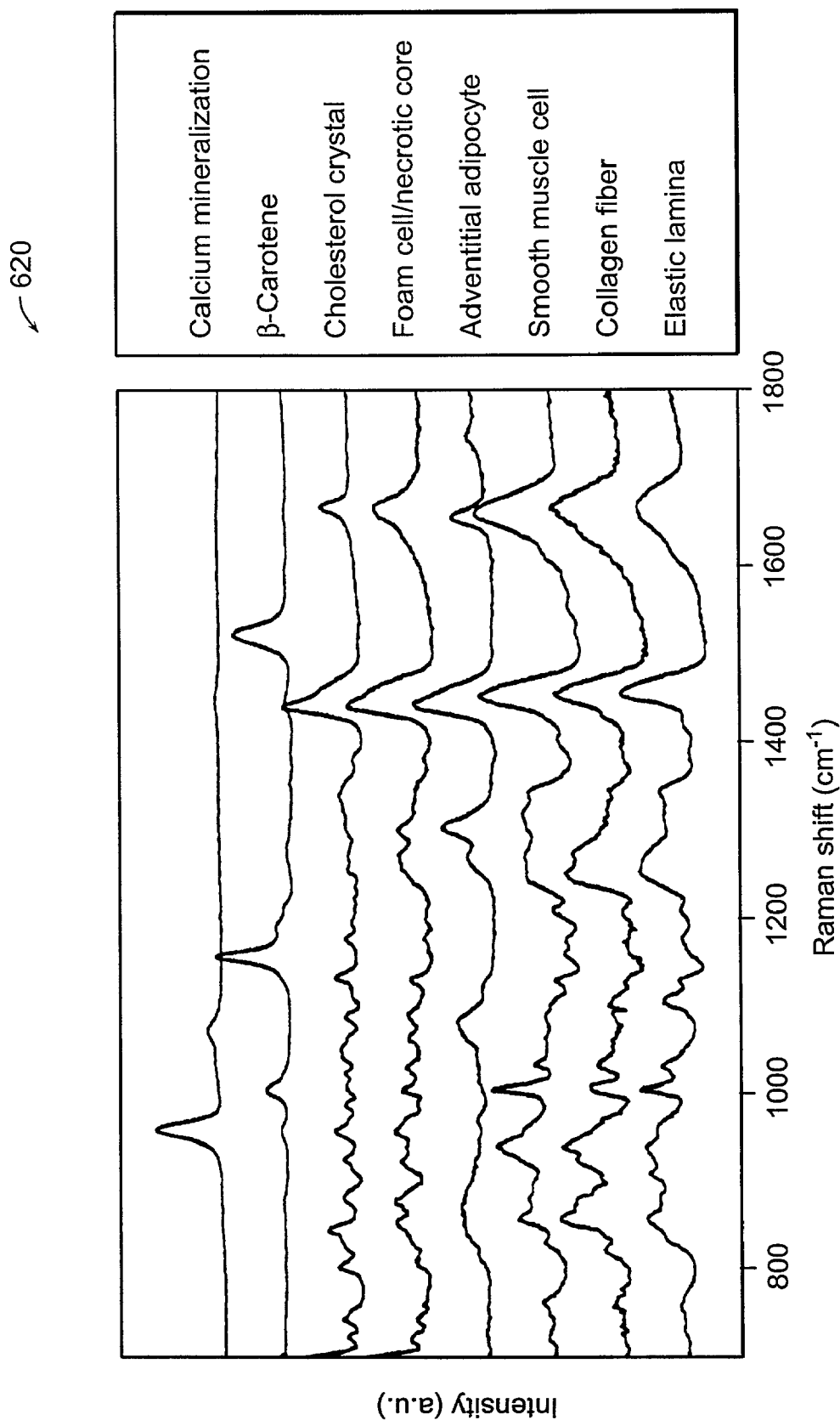
FIG. 23 graphically illustrates the Raman spectra of eight selected coronary artery morphological structures in accordance with a preferred embodiment of the present invention.

To determine the level of error in the reference data, it is necessary to analyze the signal/noise ratio (SNR) of the spectra being used. Because the microscopic Raman artery spectra of the morphological reference data can be collected for arbitrarily long times, they are virtually noise-free as illustrated in FIG. 23 which graphically illustrates the Raman spectra of eight selected coronary artery morphological structures in accordance with a preferred embodiment of the present invention. Therefore, the limiting source of error in the reference is due to noise in the macroscopic spectra of the intact arteries. The in-vitro system is shot noise-limited, and therefore, the noise for any given sample is equal to the square root of the signal. Following standard multivariate analysis techniques, the concentration error is proportional to the noise in the spectrum.

$$E = N \times B \qquad (3)$$

where $B = P^T(PP^T)^{-1}$, is the calibration vector for the morphologic basis spectrum of interest, and N is the noise in the sample.

FIGS. 2A-2C described hereinbefore show macroscopic Raman spectra collected from coronary artery samples representing each of the three diagnostic classes (normal coronary artery (FIG. 2A), noncalcified atherosclerotic plaque (FIG. 2B), and calcified atherosclerotic plaque (FIG. 2C)), together with LSM reference data. The solid lines are the macroscopic spectra and the dotted lines are indicative of the reference data. Residual (data minus the fit) are shown on the same scale. For all spectra, the calculated fit agrees well with the measured spectrum, which suggests that the morphologic basis spectra are a reasonably complete representation of the Raman spectra of the macroscopic tissue samples.

Figure 24A:
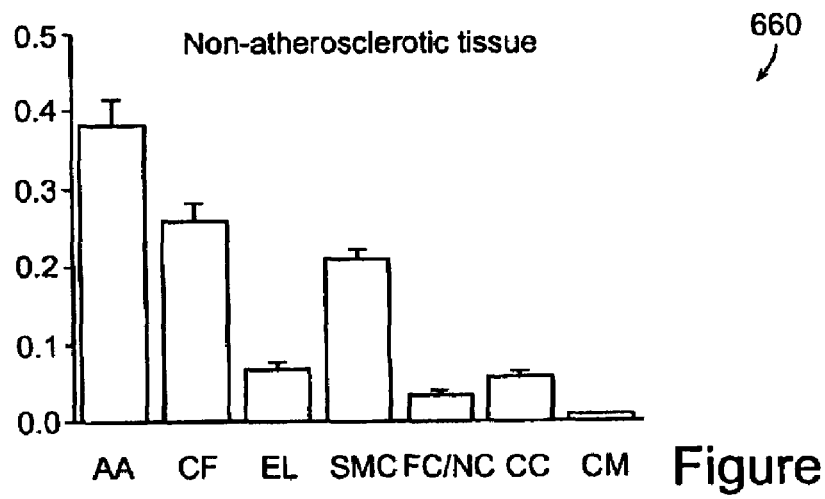
Figure 24B:
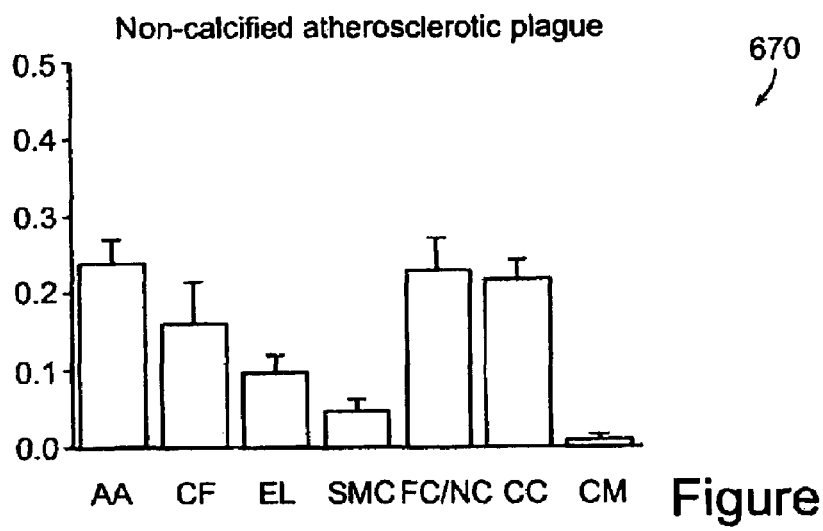
Figure 24C:
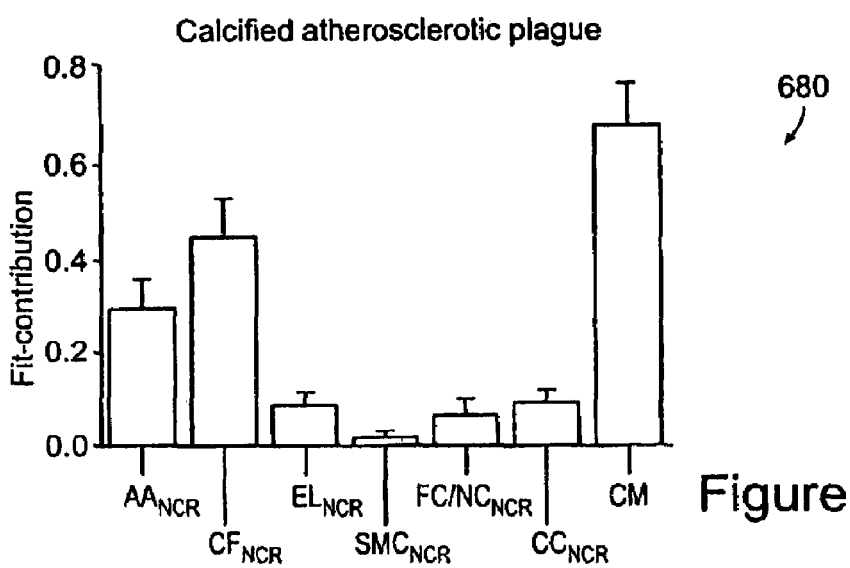

The Raman spectra of all 97 coronary artery samples in the calibration data set, which were classified by a pathologist into one of the three diagnostic classes, can be analyzed in the same way. The mean± standard error of the mean for the relative fit-contribution of all eight selected morphologic structures in nonatherosclerotic tissue (I), noncalcified atherosclerotic plaque (II), and calcified atherosclerotic plaque (III) are shown in FIGS. 24A-24C, respectively. These figures clearly show that Raman spectroscopic modeling is able to detect morphologic changes in coronary artery tissue. The morphologic Raman reference data showed, as expected, that nonatherosclerotic tissue consisted mainly of AA, CF, EL, and SMC (FIG. 24A). In nonatherosclerotic artery, the intima is thin and therefore, the contribution of the adventitial layer (which contains a relatively large amount of adipose tissue) to the spectroscopically examined tissue volume is large, because the NIR laser light penetrates through the entire vessel wall. In noncalcified and calcified atherosclerotic plaque, the morphologic Raman reference data revealed a dramatic change of the morphologic composition with progression of disease. In noncalcified atherosclerotic plaques, where the initima is thickened, the AA contribution decreased, whereas the contribution of FC/NC and CC increased (FIG. 24B) due to accumulation of lipids in the plaque. Raman spectra of calcified atherosclerotic plaques are dominated by the CM contribution (FIG. 24C). The contribution of $AA_{NCR}$ and $CF_{NCR}$ in calcified atherosclerotic plaque is larger than that of AA and CF in noncalcified atherosclerotic plaque. The reduced $CF_{NCR}$ in non-calcified plaques is an indication of decreased plaque stability.

Figure 25:
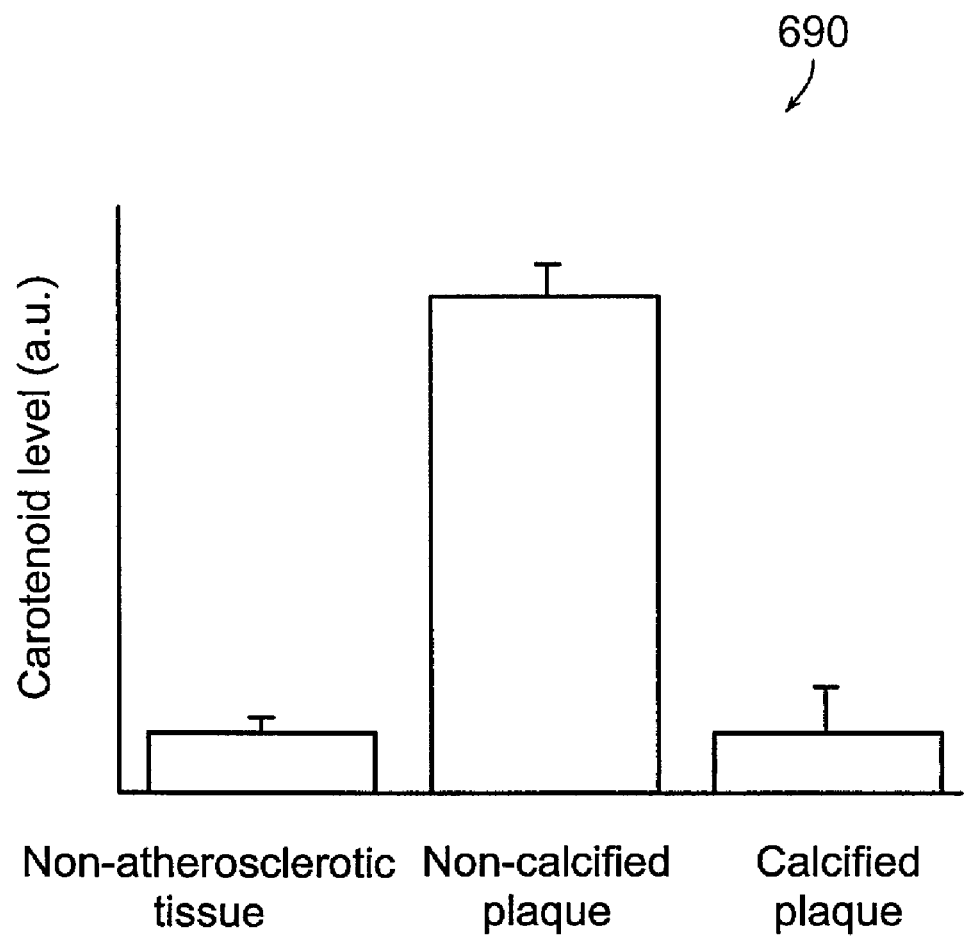
FIG. 25 illustrates the spectral contribution of $\beta$-carotene in a calibration data set in relation to three diagnostic categories, wherein the carotenoid level is expressed in arbitrary units in accordance with a preferred embodiment of the present invention.

Although the concentration of β-carotene in arterial tissue is low, the modeling outcome showed large differences in the contribution of carotenoids among the disease classes as illustrated in FIG. 25. The largest contribution is found in noncalcified atherosclerotic plaques, since β-carotene is a lipophilic substance that dissolves easily in the NC.

Using logistic regression, it is determined that an optimal separation of the data into three diagnostic classes can be obtained using the fit-contributions of CM and $FC/NC_{NCR}+CC_{NCR}$, with P<0.0001 using a likelihood-ratio test. In addition, the likelihood ratio test determined that no improvement in classification resulted from inclusion of any of the remaining morphologic structures (P<0.05). The discriminant scores are determined to be $R_{j1} = -420.4 + 1870.0 \times (FC/NC_{NCR}+CC_{NCR}) - 6094.3 \times CM$, and $R_{j2} = -8.3 + 23.3 \times (FC/NC_{NCR}+CC_{NCR}) + 47.6 \times CM$.

Figure 26A:
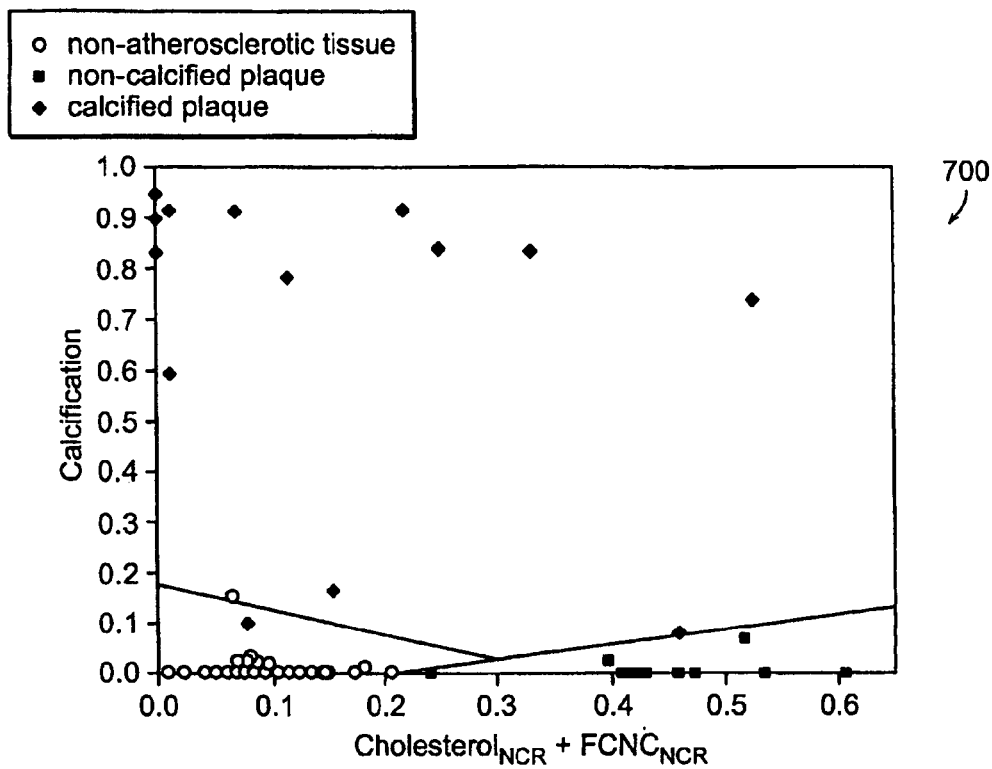
FIGS. 26A and 26B graphically illustrate the results of the algorithm developed with an initial calibration data set and the results of the prospective validation data set, respectively, in accordance with a preferred embodiment of the present invention.

The fit-contributions of CM and $FC/NC_{NCR}+CC_{NCR}$ of each artery sample can be plotted in a decision diagram as illustrated in FIG. 26A, using the corresponding $R_1$ and $R_2$ values. The border separating the regions of nonatherosclerotic tissue and noncalcified atherosclerotic plaque is given by PI=PII, which is a line described by the equation $CM = -0.07 + 0.31 \times (FC/NC_{NCR}+CC_{NCR})$. The border separating the regions of nonatherosclerotic tissue and calcified atherosclerotic plaque is given by PI=PIII, and has the equation $CM = 0.17 - 0.48 \times (FC/NC_{NCR}+CC_{NCR})$. The line separating the regions of noncalcified atherosclerotic plaque and calcified atherosclerotic plaque is given by PII=PIII, and has the equation $CM = -0.07 + 0.30 \times (FC/NC_{NCR}+CC_{NCR})$. For 95 of the 97 (98%) samples in the initial calibration data set, the decision determined by the Raman-based diagnostic algorithm correlated with that of the pathologist.

Figure 26B:
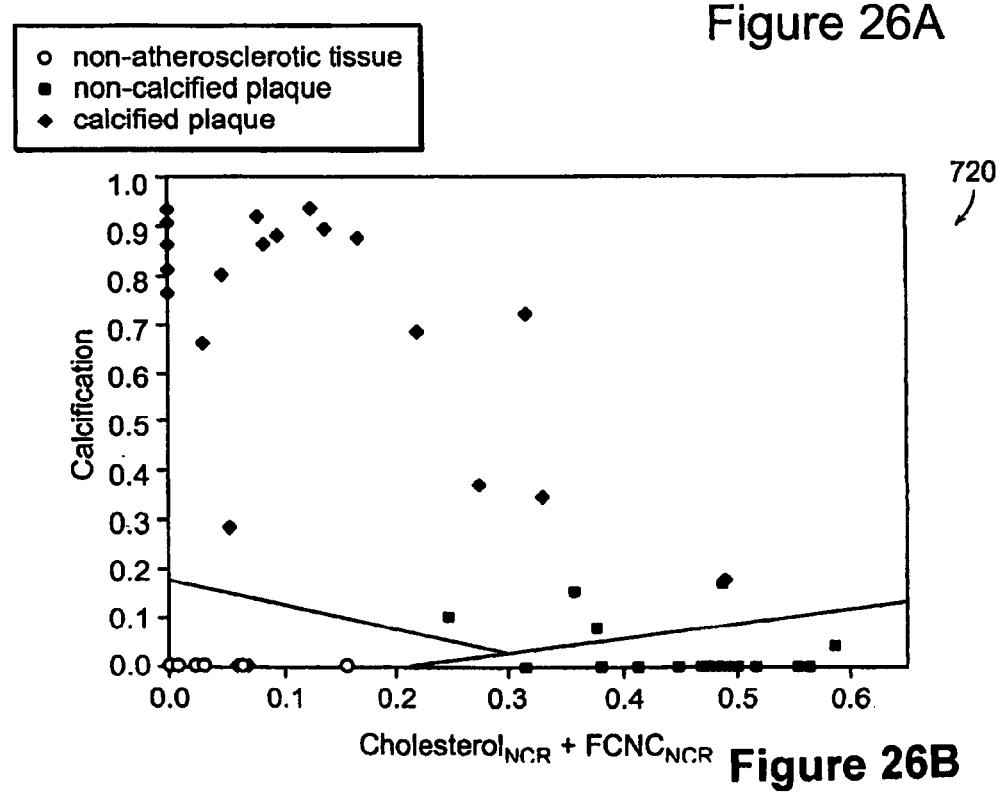

This algorithm was also used prospectively in a preferred embodiment to classify the artery samples of the second validation data set into one of the three diagnostic classes as illustrated in FIG. 26B. Prospectively, the algorithm result agreed with that of the pathologist for 64 of 68 (94%). Comparison of the pathologic and Raman spectroscopic diagnoses for both data sets is shown in Table 2.

TABLE 2

Comparison of Pathologic Diagnosis with the of the Morphology-based Raman Diagnostic Algorithm

| Raman diagnosis Pathology diagnosis | I | II | III | Total |
|---|---|---|---|---|
| Calibration data set | | | | |
| I | 72 | 0 | 1 | 73 |
| II | 0 | 9 | 0 | 9 |
| III | 1 | 0 | 14 | 15 |
| Total | 73 | 9 | 15 | 97 |
| Prospective data set | | | | |
| I | 26 | 0 | 0 | 26 |
| II | 0 | 12 | 4 | 16 |
| III | 0 | 0 | 26 | 26 |
| Total | 26 | 12 | 30 | 68 |

The classes are (1) nonatherosclerotic tissue, (II) noncalcified plaque, and (III) calcified plaque.

Because the in-vitro Raman system used for collecting macroscopic artery spectra is shot-noise limited, the NIR techniques used in acquiring the data have resulted in extremely high SNR spectra. The average peak-to-peak noise is less than 0.04 counts on normalized spectra. Calculation of error on the fit-coefficients of diagnostic morphologic components yield a three standard deviation (SD) error of 0.041 for CM, and a three-SD error of 0.036 for $FC/NC_{NCR}+CC_{NCR}$.

In another preferred embodiment, thirty-five coronary artery samples were taken from 16 explanted transplant recipient hearts, and thin sections were prepared. Using a high-resolution confocal Raman microspectrometer system with an 830-nm laser light, high signal-to-noise Raman spectra were obtained from the following morphologic structures: internal and external elastic lamina, collagen fibers, fat, foam cells, smooth muscle cells, necrotic core, β-carotene, cholesterol crystals, and calcium mineralizations. Their Raman spectra can be modeled by using a linear combination of basis Raman spectra from the major biochemicals present in arterial tissue, including collagen, elastin, actin, myosin, tropomyosin, cholesterol monohydrate, cholesterol linoleate, phosphatidyl choline, triolein, calcium hydroxyapatite, calcium carbonate, and β-carotene.

The results show that the various morphologic structures have characteristic Raman spectra, which vary little from structure to structure and from artery to artery. The biochemical model describes the spectrum of each morphologic structure well, indicating that the most essential biochemical components are included in the reference data. Furthermore, the biochemical composition of each structure, indicated by the fit contributions of the biochemical basis spectra of the morphologic structure spectrum, are very consistent. Thus, the Raman spectra of various morphologic structures in normal and atherosclerotic coronary artery may be used as basis spectra in a linear combination model to analyze the morphologic composition of atherosclerotic coronary artery lesions.

Raman spectroscopy has great potential for biochemical analysis of tissue on both the macroscopic and microscopic scale. One of the great advantages of this method is its ability to provide information about the concentration, structure, and interaction of biochemical molecules in their microenvironments within intact cells and tissues (i.e. in-situ), nondestructively, without homogenization, extraction, or the use of dyes, labels, or other contrast-enhancing agents. In addition, Raman spectroscopy can be performed in-vivo using optical fiber technology as described hereinbefore.

Using the predicate that morphologic factors may be as important as biochemical composition in determining plaque stability and progression, a preferred embodiment of the present invention includes the morphology-based diagnosis of atherosclerotic lesions in arterial tissue using Raman spectroscopy. To that end, in-situ Raman spectra of individual cellular and extracellular components of normal and atherosclerotic human coronary artery tissue were obtained in-vitro using confocal Raman microspectroscopy described hereinbefore. The biochemical composition of these microscopic morphologic structures were then determined by modeling their Raman spectra using a linear combination of basis Raman spectra of biochemicals in a similar way as used previously for intact tissue. Analogous to the macroscopic Raman spectroscopy biochemical analyses, these macroscopic Raman spectroscopy morphologic analyses can ultimately be used in a diagnostic algorithm to assess atherosclerotic plaque stability and disease progression in-vivo. Human coronary artery samples (n=35), exhibiting varying stages of atherosclerosis, were obtained from explanted recipient hearts (n=16) within 1 hour of heart transplantation. Immediately after dissection from the explanted hearts, the artery samples were rinsed with neutral buffered saline, snap frozen in liquid nitrogen, and stored at −85C.

Frozen coronary artery samples were mounted on a cryostat chuck with Histoprep (Fisher Diagnostics, Orangeburg, N.Y.). Thin transverse tissue sections (6-8 µm) for light microscopy and Raman microspectroscopy were cut using a cryostat/microtome (International Equipment, Needham Heights, Mass.). Four sections of each sample were mounted on glass microscope slides and stained with hematoxylin and eosin. Serial unstained sections were then mounted on $BaF_2$ or $MgF_2$ flats (International Scientific Products, Tarrytown, N.Y., and Spectra-Tech., Stamford, Conn.), kept moist with phosphate buffered saline (pH 7.4), and transferred to the microscope stage for spectroscopic experiments performed at room temperature. No coverslip was used for spectroscopic measurements. If spectra were collected from a large number of morphologic structures, each section was replaced by a freshly cut section after approximately 2 hours to avoid biochemical changes in the tissue as a result of enzymatic degradation. No significant changes were seen in the Raman spectra within this 2 hour period of study. The morphologic structures examined were in normal arteries: collagen fibers in the various layers of the arterial wall, internal and external elastic laminae, medial smooth muscle cells, and adventitial fat cells, and in intimal atherosclerotic lesions: collagen fibers in the fibrous cap, foam cells, necrotic core, cholesterol crystals, β-carotene-containing crystals, and calcium mineralizations.

Figure 27:
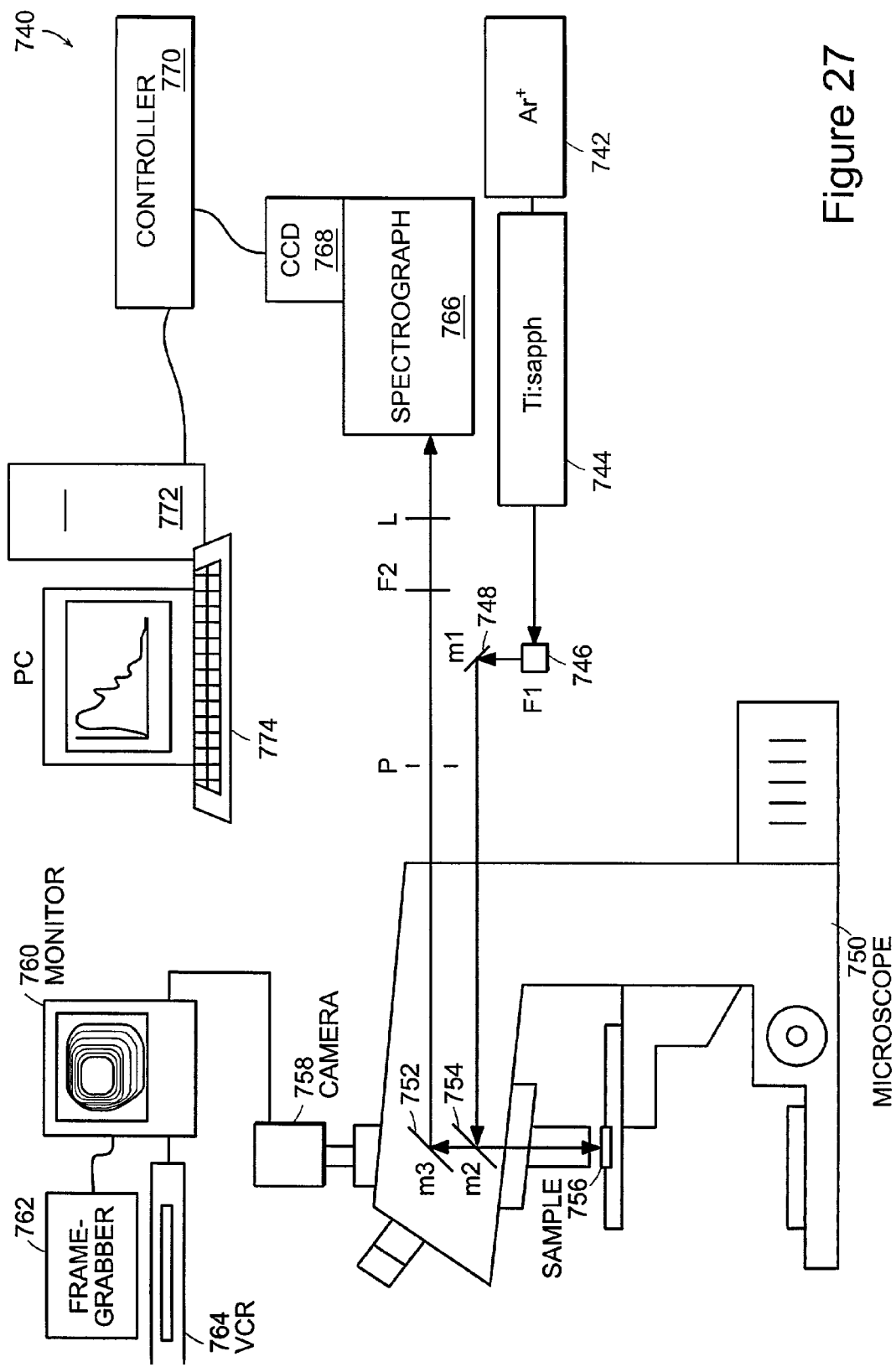
FIG. 27 is a schematic diagram of a system including a confocal Raman microspectrometer in accordance with a preferred embodiment of the present invention.

A schematic representation of the system in accordance with the preferred embodiment of the present invention is shown in FIG. 27. All Raman spectroscopic measurements are carried out using a confocal configuration in order to suppress signal Raman light from features that are in peripheral surfaces other than the region of interest of the selected morphologic structure. The observation and analysis used a microscope (Zeiss Axioskop 50, Zeiss, Thornwood N.Y.), fitted with a phase contrast system and a stage controller (Prior Scientific Instruments, Cambridge, Mass.). Initial examination of the sample was performed with phase contrast microscopy at 10× magnification (Zeiss Achroplan objective). Detailed examination and microspectroscopy were performed with 63× infinitely corrected water immersion objective (Zeiss Achroplan, NA 0.9). The phase contrast tissue examination and morphologic structure selection for microspectroscopy were recorded using a CCD color video camera 758 (Sony, Cambridge, Mass.) attached to the microscope 750 and stored on video tape (VCR) 764 from which frames were digitized (PCVision-plus, Imaging Technologies, Bedford, Mass.).

Near-infrared (830 nm) laser light was generated by an $Ar^+$ laser 742-pumped Ti: sapphire laser system 744 (Coherent Innova 90/Spectra Physics 3900S, Coherent, Santa Clara, Calif.). The laser output was band pass filtered 746 (F1) (Kaiser Optical Systems HLBF, Ann Arbor, Mich.) and focused onto the sample using an adjustable mirror (m1) 748, and a dichroic beamsplitter (m2) 754, with a laser power on the sample 756 of 50-100 mW. Light emitted from the tissue sample was collected by the same objective, passed through the beamsplitter and passed through a pinhole (P: 100 µm diameter) by a removable mirror (m3) 752. This mirror was used to direct either light emitted from the sample to the spectrometer/CCD system, or white light images to the video camera system. The light directed to the CCD/spectrometer is then Notch-filtered to reject Rayleigh scattered light (F2; Kaiser Optical Systems HSNF) and focused with an achromatic lens (L) into a Chromex 250IS/SM spectrograph-monochromator (Chromex, Albuquerque, N. Mex.). The spectrograph 766 includes a grating dispersed light onto a back illuminated deep-depletion CCD detector 768 (Princeton Instruments, Princeton, N.J.) cooled to −100° C. The CCD interface (ST130 Princeton Instruments) was connected to a personal computer 774 using Winspec software (Princeton Instruments, version 1.4.3), which performed data processing and storage. At least three Raman spectra (sampling time between 10 and 100 s) over a range of 100-2000 $cm^{-1}$ (8 $cm^{-1}$ resolution) were obtained from each site selected.

The method to estimate the light collection or sampling volume of the confocal Raman microspectrometer uses a small (1-2 µm³) collection volume to insure adequate resolution to collect Raman spectra from small or thin microscopic structures, such as individual collagen fibers. In short, polystyrene beads of 1.0 µm diameter (Polysciences, Warrington, Pa.) were moved through the focused laser beam, and the Raman signal was collected as a function of the bead position relative to the center of the laser focus. The step resolution of the microscope stage in the horizontal plane was 1 μm. Vertical displacement proceeded in 1.1 μm steps. The position is optimized to obtain the maximal Raman signal of the bead. Lateral resolution is determined by alternately measuring the Raman signal of the central position and one of eight positions in the X or Y direction from the center of the bead using 1- or 2-μm steps. The intensity of the strong 1004 cm$^{-1}$ polystyrene Raman band is measured as a function of the distance to the laser focus in both the planar directions and the axial direction. The result for each direction is then fitted with a Gaussian function, and the diameter of the focused beam is determined from the full width at half-maximum intensity (FWHM). For both lateral directions, the diameter is about 1 μm while the axial direction is 2 μm. The sampling volume is calculated to be about 2 μm$^3$.

Data analysis of Raman spectra from morphologic structures is performed with Microcal Origin software (version 4.10, Clecom, Birmingham, UK). This analysis consists of cosmic ray removal, wavenumber shift calibration using the spectral features of toluene (Mallinckrodt Specialty Chemicals, Paris, Ky.) and correction for chromatic variation in the filter/spectrometer/CCD detector system with a calibrated tungsten light source. The tissue spectra is then corrected for BaF$_2$ or MgF$_2$ background contribution by subtraction of the appropriate spectrum, and corrected for tissue fluorescence by subtraction of a fourth-order polynomial that is fitted to the spectrum by least-squares minimization (LSM).

Each morphologic structure spectrum is modeled in the Raman shift range of 700-1800 cm$^{-1}$, using a simple linear combination reference to generate fractional fit contributions (C$_1$) for each of the 12 biochemical components, as $$r_{total} = C_1 r_1 + C_2 r_2 + C_3 r_3 \quad (4)$$

where r is the Raman spectrum. The 700-1800 cm$^{-1}$ Raman shift range is chosen because this range contains most spectral information.

Reagent grade commercial chemicals (Sigma, St. Louis, Mo.), are used to obtain the Raman spectra, for use as basis spectra, of the 12 biochemical components, including proteins (collagen type III, elastin, actin, myosin, and tropomyosin), unesterified cholesterol (cholesterol monohydrate), cholesterol esters (cholesterol linoleate), phospholipids (phosphatidyl choline), triglycerides (triolein), carotenoids (β-carotene), and calcium salts (calcium hydroxyapatite and calcium carbonate). These 12 biochemical components are selected as the most common Raman active biochemical species found in normal arterial tissue and atherosclerotic plaque. Additionally, a similar set of biochemical constituents has provided good fit of the reference data to the observed spectrum in previous macroscopic tissue studies. The Raman spectra from these chemicals is recorded in a similar way as the Raman spectra from the morphologic structures.

The reference data components cannot be scaled on chemical weight, since the actual concentration of the biochemicals in the various morphologic structures in unknown. Therefore, the intensity of the spectral feature at 1440-1455 cm$^{-1}$ (representing the bonding of CH$_2$ bonds in protein and lipid) is set to unity. The Raman spectra of β-carotene, calcium carbonate, and calcium hydroxyapatite, which lack spectral features in this region, are set to unity with respect to spectral features at 1159, 1080, and 961 cm$^{-1}$, respectively. This reference thus provides information about the relative fit contribution of these chemical components to the Raman spectra of the various morphologic structures. The fit contribution of each biochemical component is expressed as a fraction of the maximum (i.e. 1).

Figure 28B:
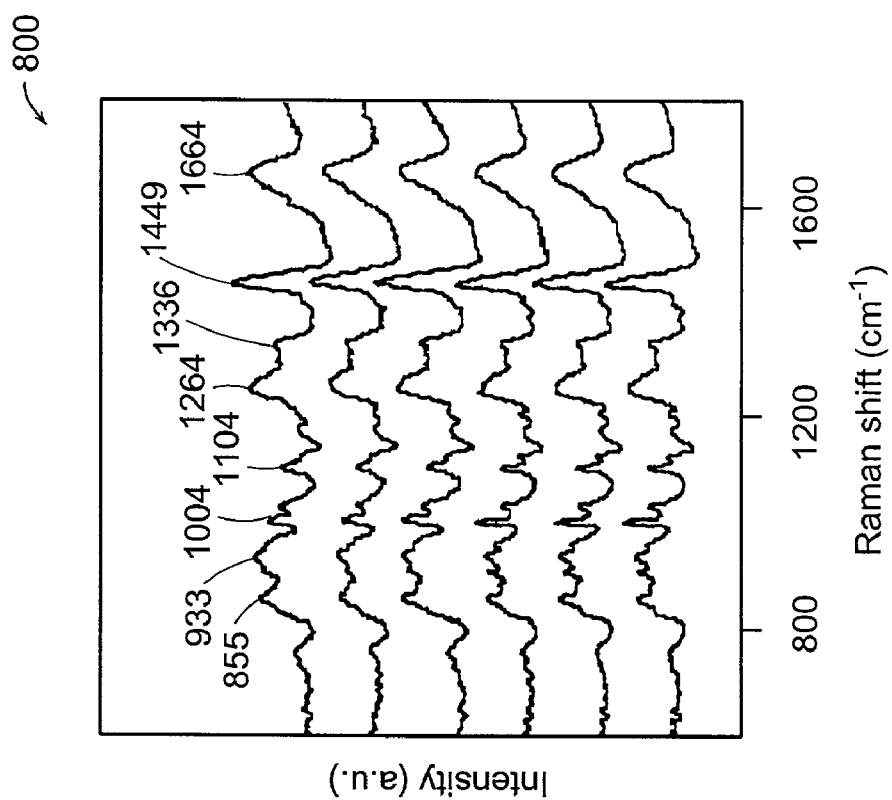
FIGS. 28A and 28B are a photomicrograph of internal elastic lamina in a 6-µm unstained coronary artery section viewed under phase contrast and the Raman spectrum of the internal elastic lamina, respectively, in accordance with a preferred embodiment of the present invention.
Figure 28A:
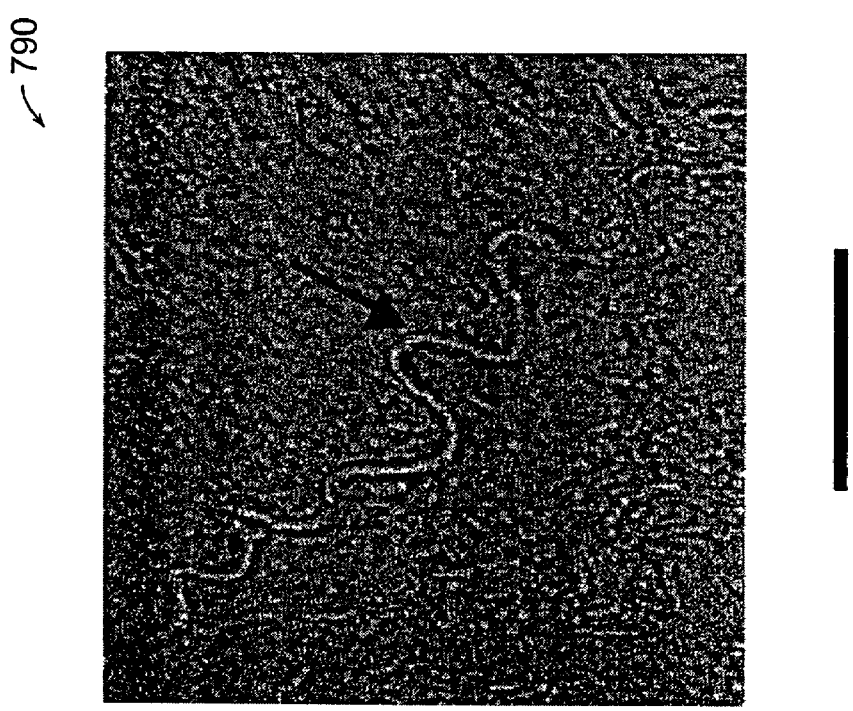

FIG. 28A is a photomicrograph of an unstained coronary artery section showing the internal elastic lamina viewed under phase contrast. This structure is examined at a total of 54 sites in 21 coronary artery samples. In nine of these samples, were collected spectra from the external elastic lamina. In FIG. 28B, the Raman spectra of six different internal elastic laminae are shown. The bands at 1664 and 1264 cm$^{-1}$ are attributable to the amide I and III vibrations, respectively, of structural proteins such as elastin and collagen. The intense band at 1449 cm$^{-1}$ can be assigned to the CH$_2$ and CH$_3$ bending mode of proteins, while the 1004 cm$^{-1}$ band is due to phenylalanine. The bands at 1336 and 1104 cm$^{-1}$ are attributable to desmosine/isodesmosine, and are specific for elastin. The bands at 933 and 855 cm$^{-1}$ can be assigned to the C—C stretching mode of proline and are present in collagen. These results indicate that internal elastic lamina contains both elastin and collagen. Furthermore, on visual inspection, these spectra show very little variation from structure to structure, indicating that the biochemical composition of internal elastic lamina is very consistent within and between coronary artery samples. Spectra obtained from the external elastic lamina are identical to those obtained from the internal elastic lamina.

Figure 29B:
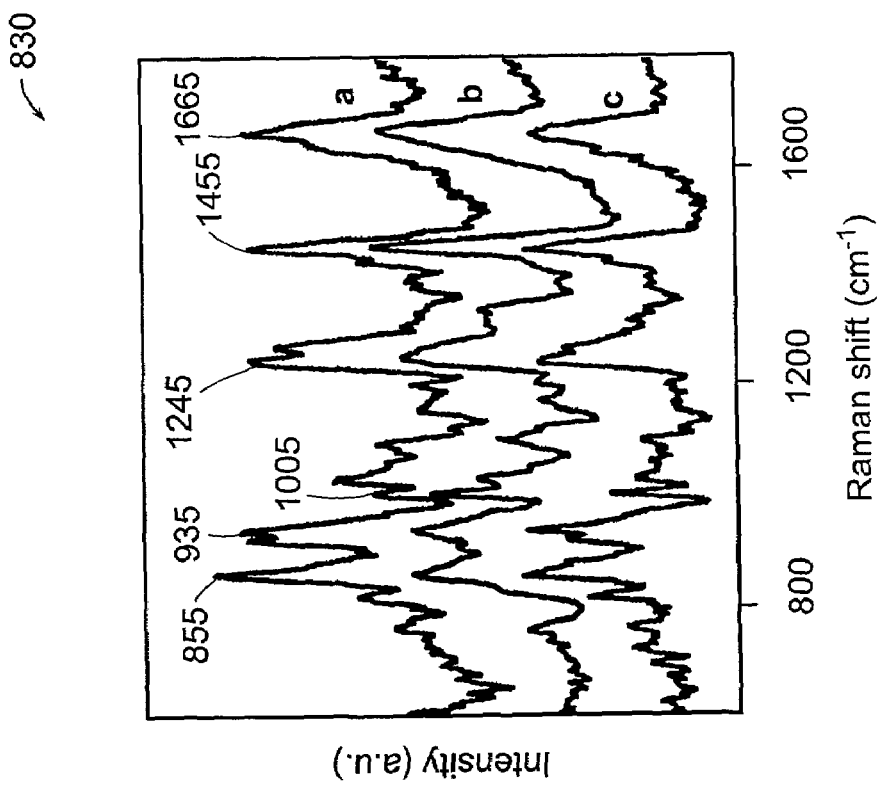
FIGS. 29A and 29B are a photomicrograph of the tunica adventitia with collagen fibers in a 6-µm unstained coronary artery section viewed under phase contrast and the Raman spectrum of the fibers, respectively, in accordance with a preferred embodiment of the present invention.
Figure 29A:
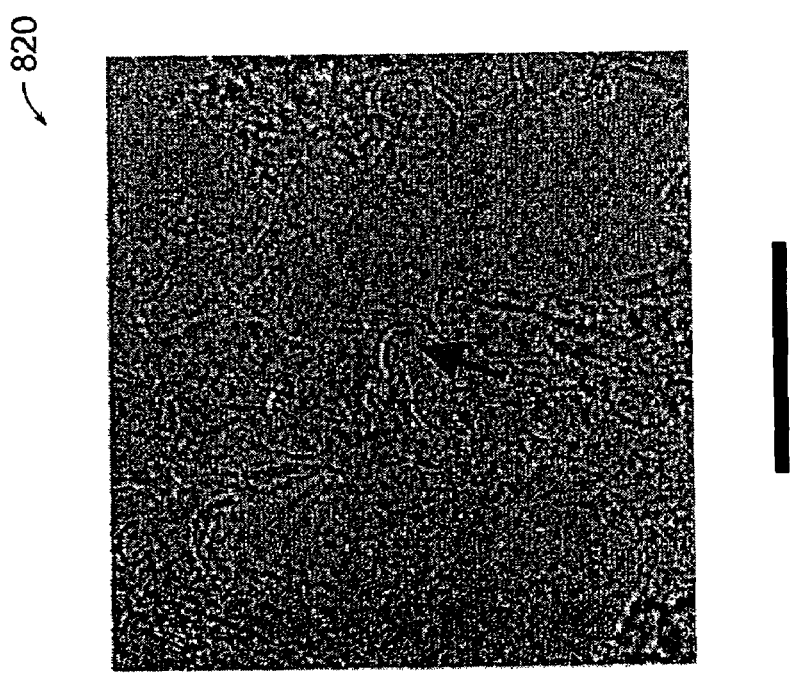

FIG. 29A is a phase contrast photomicrograph showing collagen fibers (length approximately 10 μm, diameter approximately 2 μm) in the connective tissue of the tunica adventitia. In total, 17 collagen fibers in 10 samples were studied. FIG. 29B shows the Raman spectra from collagen fibers from three different artery samples. Again, on visual inspection, these spectra collected from the adventitia (a, b) show little variation from fiber to fiber within or among coronary artery samples, and are identical to those taken from collagen fibers in the fibrous cap (c) of intimal atherosclerotic lesions. These spectra are also very similar to those from the elastic laminae, except for the absence of desmosine and isodesmosine bands (specific for elastin). The collagen fiber spectra also contain a pronounced hydroxyproline contribution (855 cm$^{-1}$) specific for collagen.

Figure 30:
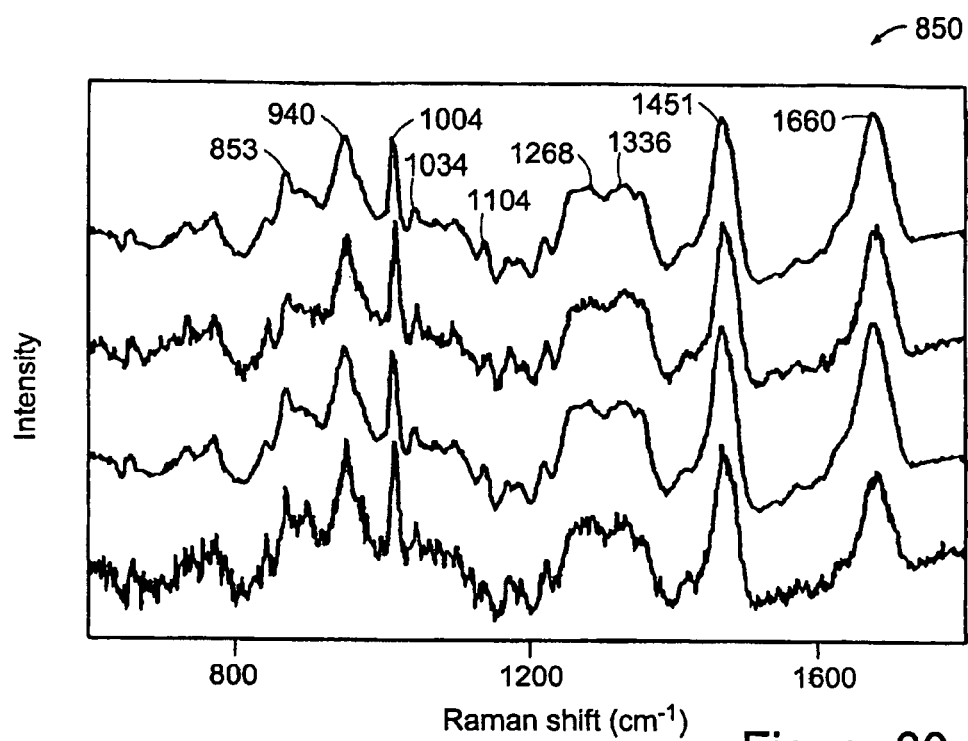
FIG. 30 graphically illustrates the Raman spectra of four different smooth muscle cells in the tunica media in accordance with a preferred embodiment of the present invention.

FIG. 30 shows four Raman spectra recorded from smooth muscle cells in the tunica media in normal and atherosclerotic coronary artery samples in accordance with a preferred embodiment of the present invention. In total, 32 spectra were recorded from 10 coronary artery samples. On visual inspection, no significant differences were observed between spectra taken from individual smooth muscle cells. The main spectral features in the smooth muscle cell spectra are similar to those observed in the elastic laminae and collagen fiber spectra, and are dominated by protein bands at 1660 and 1268 cm$^{-1}$ (amide I and III vibrations, respectively), 853, 940, 1034, 1336 and 1451 cm$^{-1}$ (C—C or C—H bending), and 1004 cm$^{-1}$ (phenylalanine). The main differences between the protein-dominated smooth muscle cell, elastic laminae, and collagen fiber spectra are in intensity variations in the phenylalanine (1004 cm$^{-1}$), desmosine/isodesmosine (1336 and 1104 cm$^{-1}$) and amide III (1268 cm$^{-1}$) bands.

Figure 31:
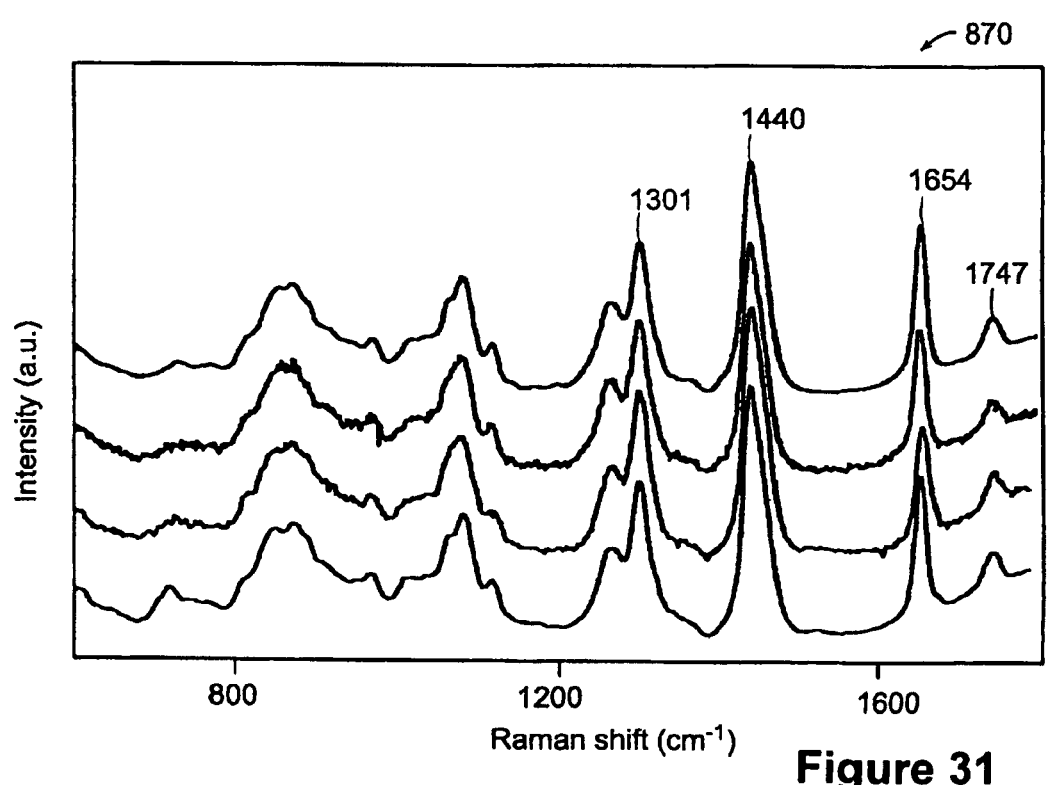
FIG. 31 graphically illustrates the Raman spectra of four fat cells (adipocytes) in the tunica adventitia in accordance with a preferred embodiment of the present invention.

FIG. 31 shows examples of Raman spectra collected from fat cells (adipocytes) in the tunica adventitia in accordance with a preferred embodiment of the present invention. In total, eight adipocytes were examined from six coronary artery samples. The spectra collected from the fat cells are very similar, and are dominated by an ester band (1747 cm$^{-1}$), an unsaturated carbon/carbon band (C=C; 1654 cm$^{-1}$), and CH$_2$/CH$_3$ bands (1440 and 1301 cm$^{-1}$), which, in combination, indicate triglycerides.

Figure 32B:
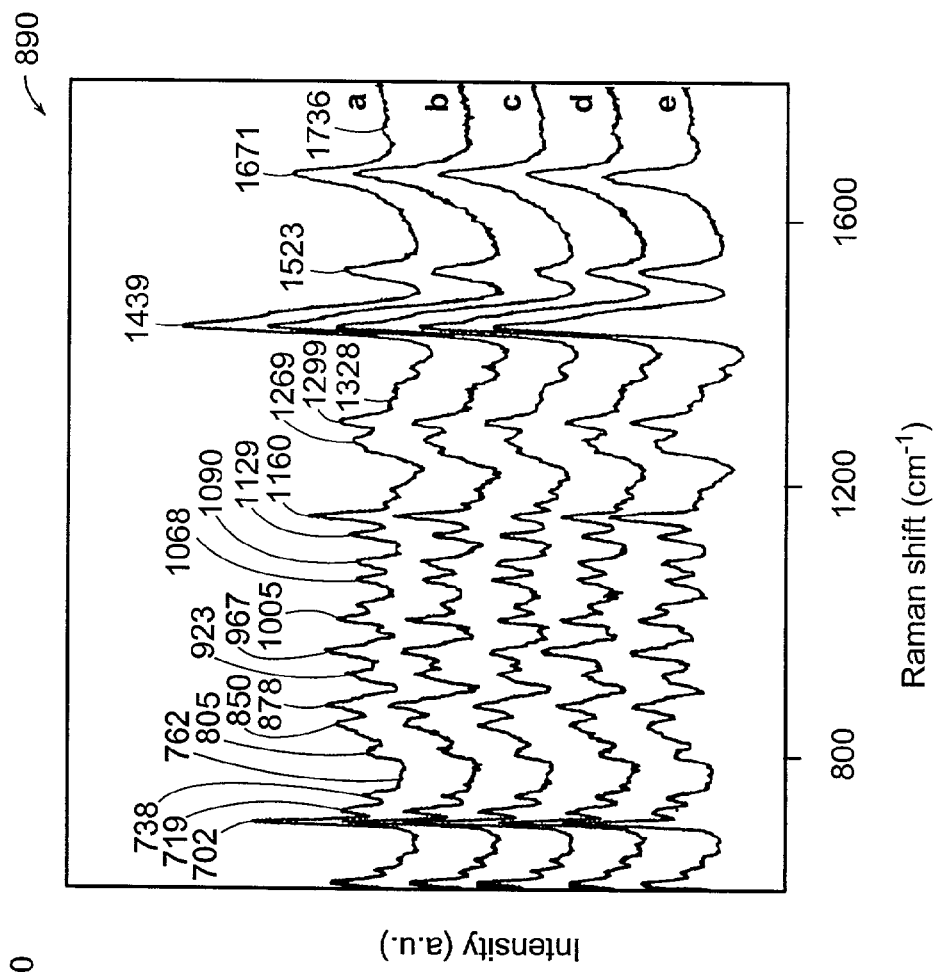
FIGS. 32A and 32B are a photomicrograph of foam cells in an intimal athersclerotic plaque in a 6-µm unstained coronary artery section viewed under phase contrast and a Raman spectra of the foam cells and necrotic core, respectively, in accordance with a preferred embodiment of the present invention.
Figure 32A:
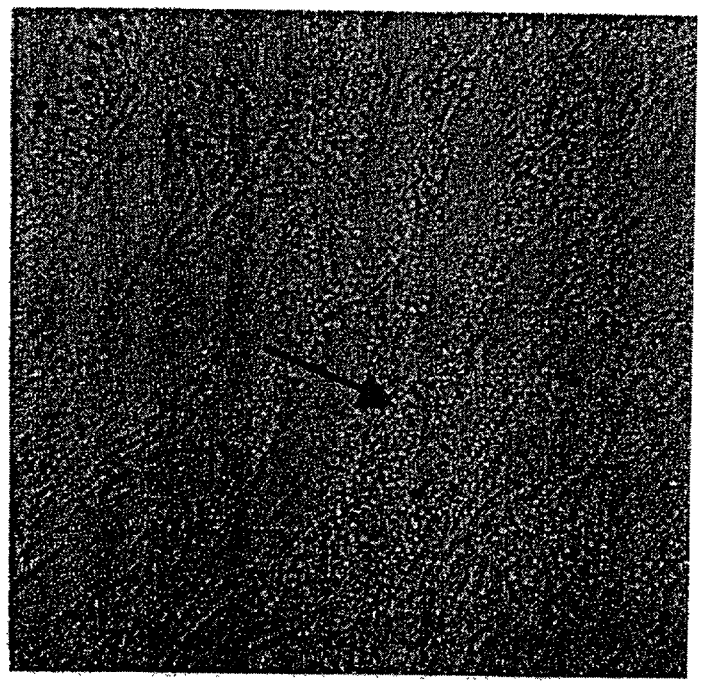

FIG. 32A is a phase contrast photomicrograph of foam cells in the intima of an atheromatous plaque. The individual lipid droplets in these cells can easily be identified. In total, 30 foam cells in eight coronary artery samples were studied. In FIG. 32B, the Raman spectra from three foam cells are shown (a-c). Although similar on visual inspection, these spectra show more variation among foam cells than the spectra of collagen fibers, the internal and external elastic laminae, and smooth muscle cells. More specifically, the foam cell spectra are distinctly different from the protein-dominated spectra of the elastic laminae, collagen fibers, and smooth muscle cells, particularly with regard to the numerous bands below 1100 $cm^{-1}$. The bands at 702, 878, 923, and 957 $cm^{-1}$ can be assigned to the steroid nucleus of both unesterified (free) cholesterol and cholesterol esters. The intense bands at 1671, 1439, 1299, and 1270 $cm^{-1}$ are due to C=C stretch and $CH_2/CH_3$ bending modes. The presence of bands at 1735 and 1026 $cm^{-1}$ (specific for cholesterol esters) and 1058 and 1328 $cm^{-1}$ (specific for free cholesterol) indicates that these foam cells contain both esterified and unesterified cholesterol. As discussed previously, the reduced $CF_{NCR}$ in non-calcified plaques is indicative of decreased plaque stability. The bands at 719 $cm^{-1}$ (symmetric choline stretch), 762 $cm^{-1}$ (symmetric O—P—O stretch), and 878 $cm^{-1}$ (asymmetric O—P—O stretch) indicate the presence of phospholipids, and those at 1523 and 1160 $cm^{-1}$ the presence of β-carotenoids. However, the foam cell spectra lack the triglyceride bands at 1747, 1654, 1440, and 1301 $cm^{-1}$ seen in adventitial fat cells.

In total, 31 necrotic core regions in 16 coronary artery samples were studied. FIG. 32B also shows two examples of Raman spectra collected from necrotic core (d and e). Similar to the foam cell spectra, there is some variation from structure to structure within the necrotic core. However, the average spectra from foam cells and necrotic core are quite similar, indicating that the chemical contents of both morphologic structures are quite similar.

Figure 33:
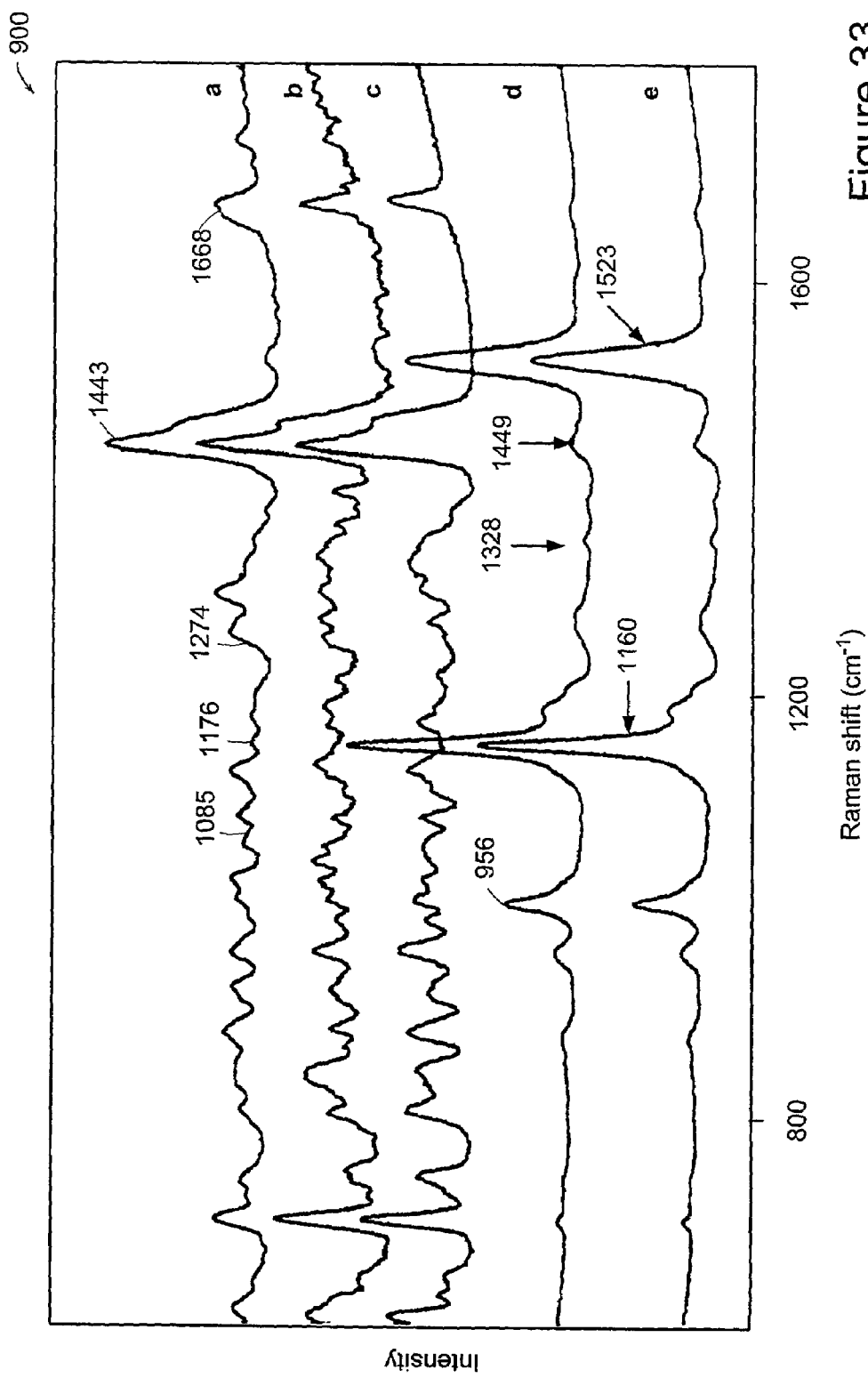
FIG. 33 graphically illustrates the Raman spectra of cholesterol crystals in intimal atherosclerotic plaques in accordance with a preferred embodiment of the present invention.

FIG. 33 shows examples of Raman spectra taken from cholesterol crystals of different size in the necrotic core of atheromatous plaques. In total, cholesterol crystals in seven coronary artery samples were studied. The main spectral features of the cholesterol crystal spectra are at 1668 $cm^{-1}$ (C=C stretch), 1443, 1328, and 1274 $cm^{-1}$ ($CH_2$, $CH_3$ bending), and 1176 and 1085 $cm^{-1}$ (C—C stretch). The spectral features below 1000 $cm^{-1}$ are attributed to steroids, indicating the presence of unesterified cholesterol. Slightly more variation was seen between the spectra from individual crystals, mainly due to band intensity variations, indicative of differences in the ratio of free to esterified cholesterol in the crystals themselves or in the tissue components surrounding the crystals.

In necrotic core regions, yellow crystals could be identified under phase contrast occasionally. FIGS. 33 (*d* and *e*) shows the Raman spectra of two such crystals from two different coronary artery samples. In total, seven of these crystals from three samples were studied. The main spectral features are bands at 1523 and 1160 $cm^{-1}$ which are due to C—C and C=C stretches and indicative of β-carotene. Given the presence of bands at 1449 and 956 $cm^{-1}$, these yellow crystals also appear to contain some structural proteins and cholesterol esters.

Figure 34B:
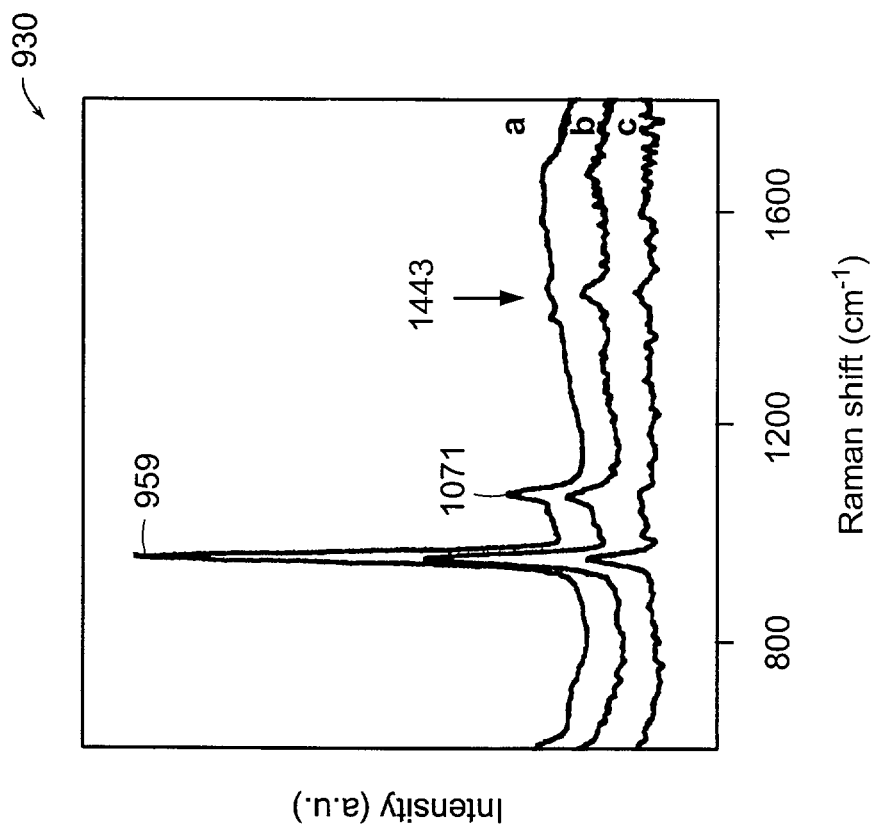
FIGS. 34A and 34B are a photomicrograph of the calcification in the necrotic core of an intimal atherosclerotic plaque in a 6-µm unstained coronary artery section viewed under phase contrast and the corresponding Raman spectra in accordance with a preferred embodiment of the present invention.
Figure 34A:
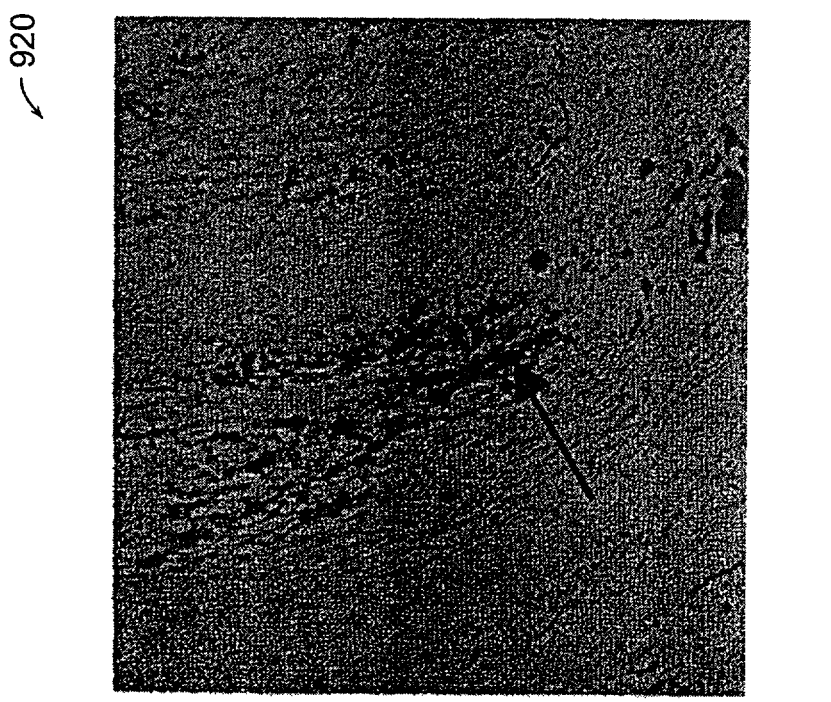

FIG. 34A is a photomicrograph of an atherosclerotic plaque containing a calcification. In total, 15 calcium mineralizations in six coronary artery samples were studied. Raman spectra representing different stages of calcification in two atherosclerotic plaques are shown in FIG. 34B. The main features of these spectra are 1071 and 959 $cm^{-1}$ bands attributed to $CO_3^{2-}$ (symmetric)/$PO_4^{3-}$ (asymmetric) and $PO_4^{3-}$ (symmetric) stretches, indicative of calcium carbonate and calcium hydroxyapatite, respectively. Large calcium mineralizations (FIGS. 34B, *a* and *b*) show spectral features different from those of minute punctate calcium mineralizations in the necrotic core (FIGS. 34B, *c*). The main difference is the presence of additional features in the spectra of the punctate calcium mineralizations attributable to lipids and/or phospholipids (1433 $cm^{-1}$), most likely due to the surrounding necrotic core.

Figure 35:
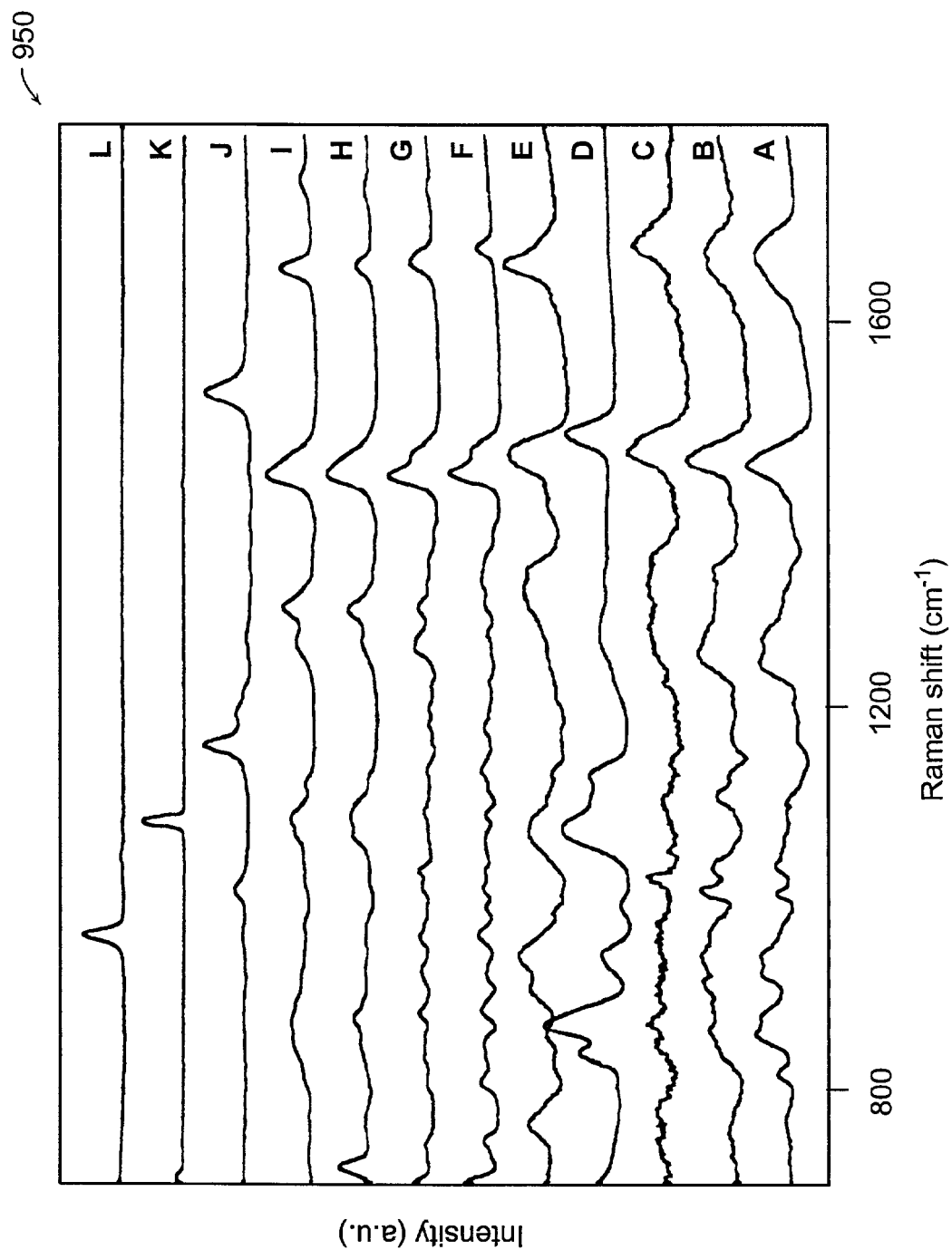
FIG. 35 graphically illustrates a Raman basis spectra of the 12 biochemicals used for linear fitting to the morphologic spectra in accordance with a preferred embodiment of the present invention.
Figure 36A:
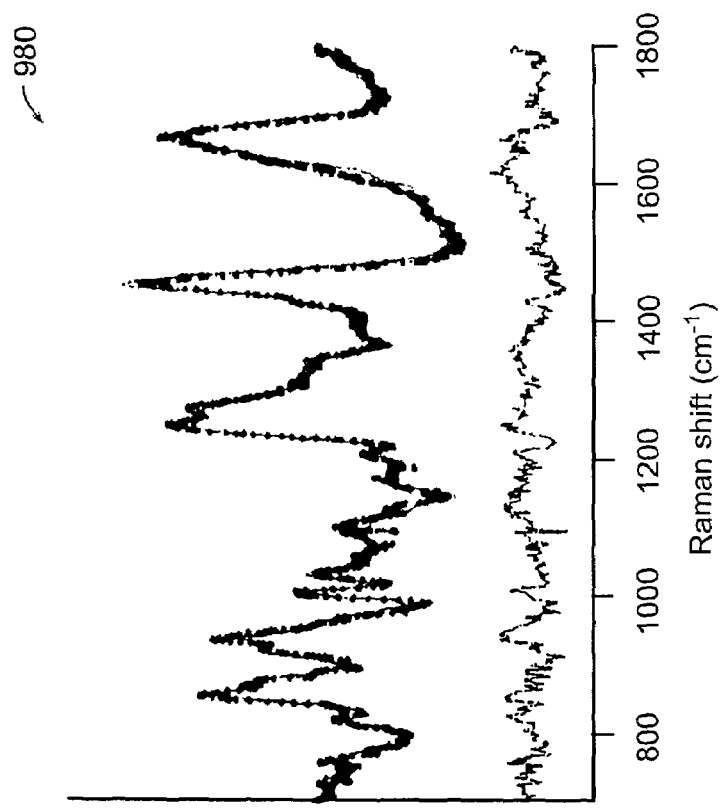
FIGS. 36A-36H provide a graphical comparison between observed data and reference data of spectra of the different morphological structures in the coronary artery in accordance with a preferred embodiment of the present invention.
Figure 36B:
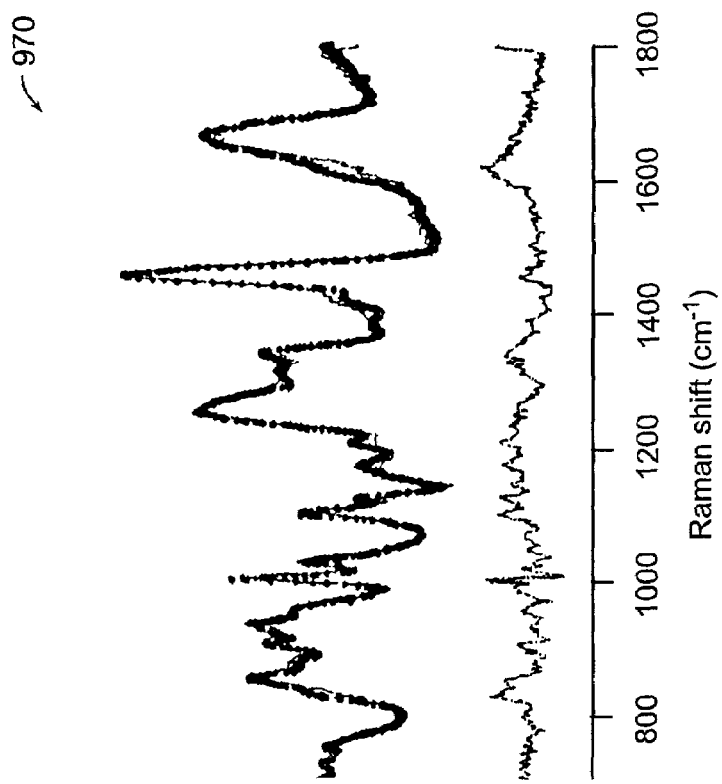
Figure 36D:
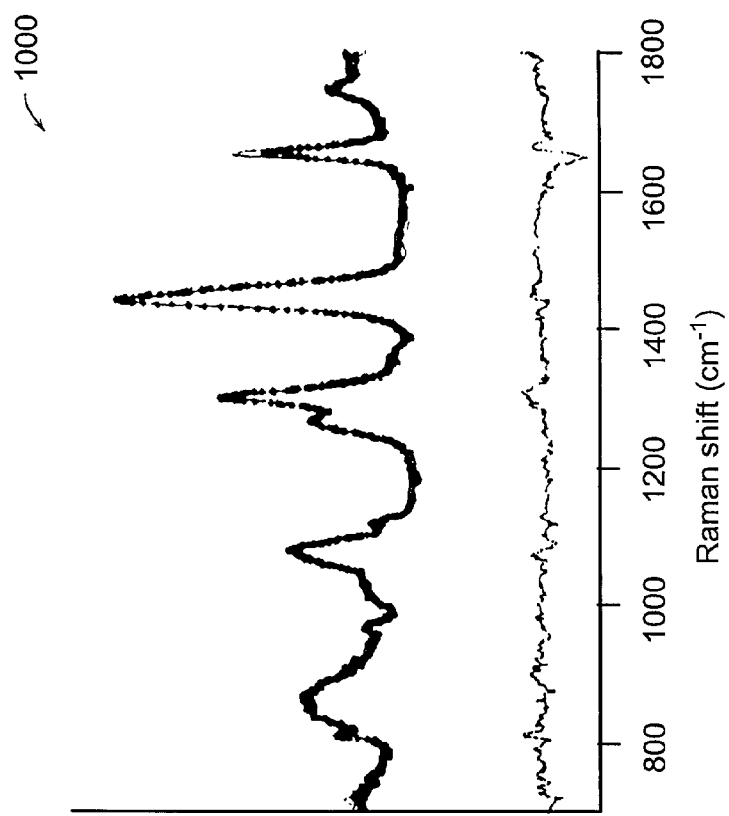
Figure 36C:
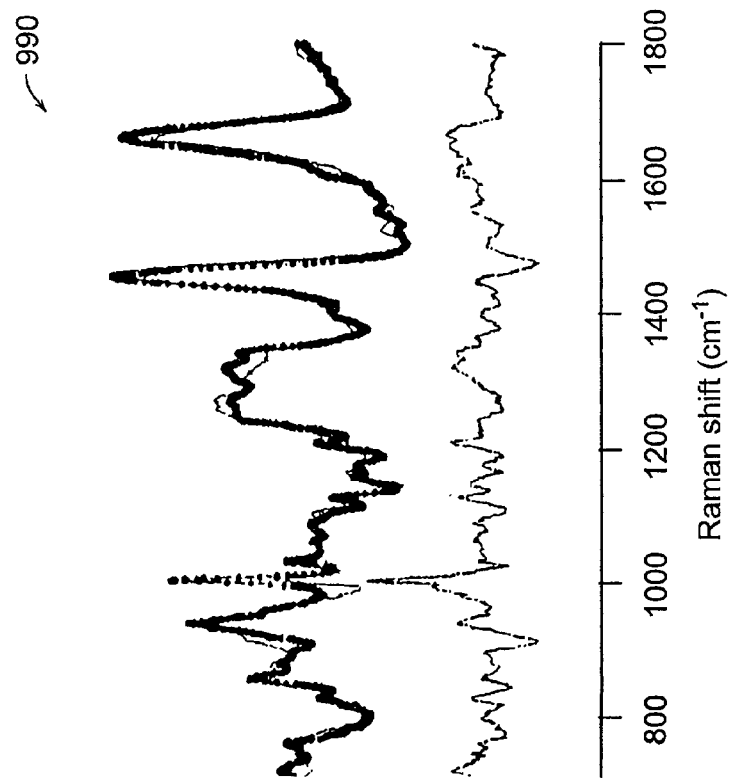
Figure 36F:
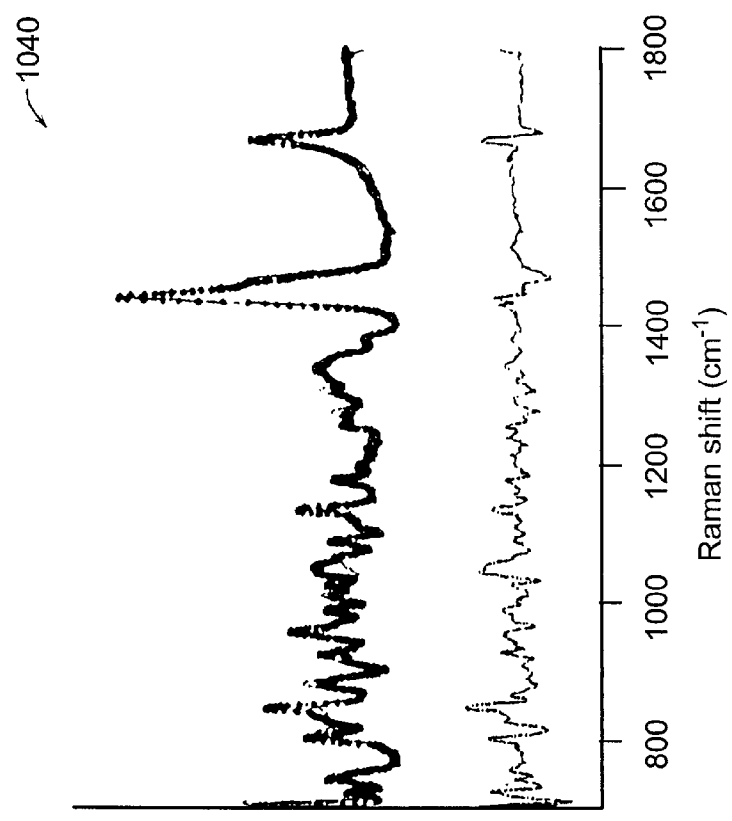
Figure 36E:
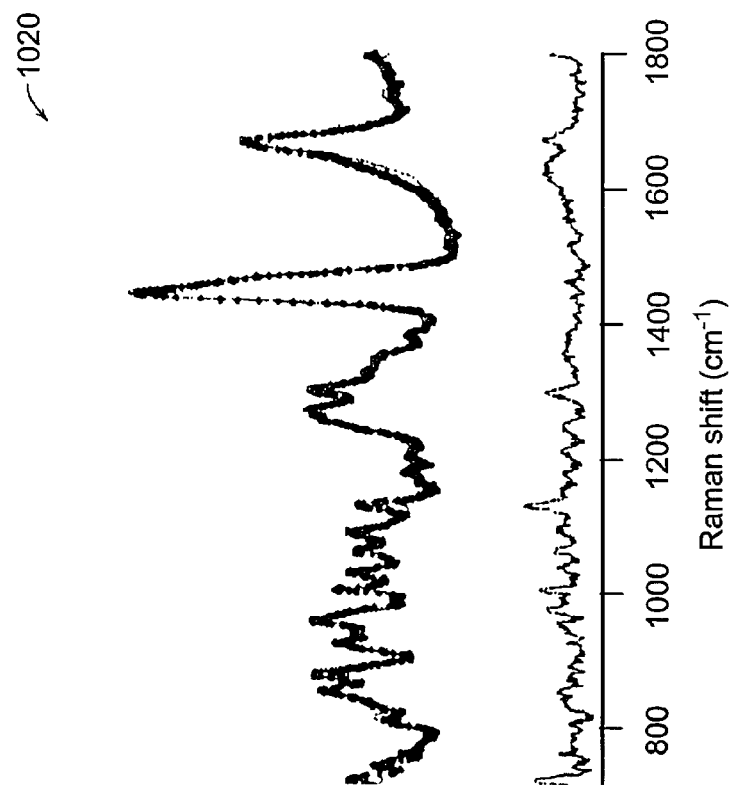
Figure 36H:
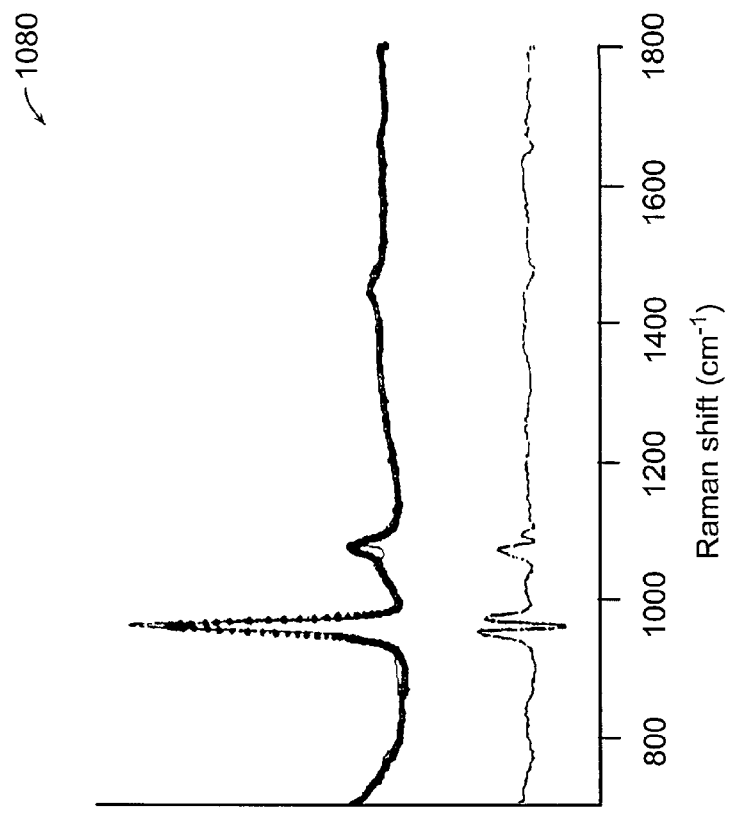
Figure 36G:
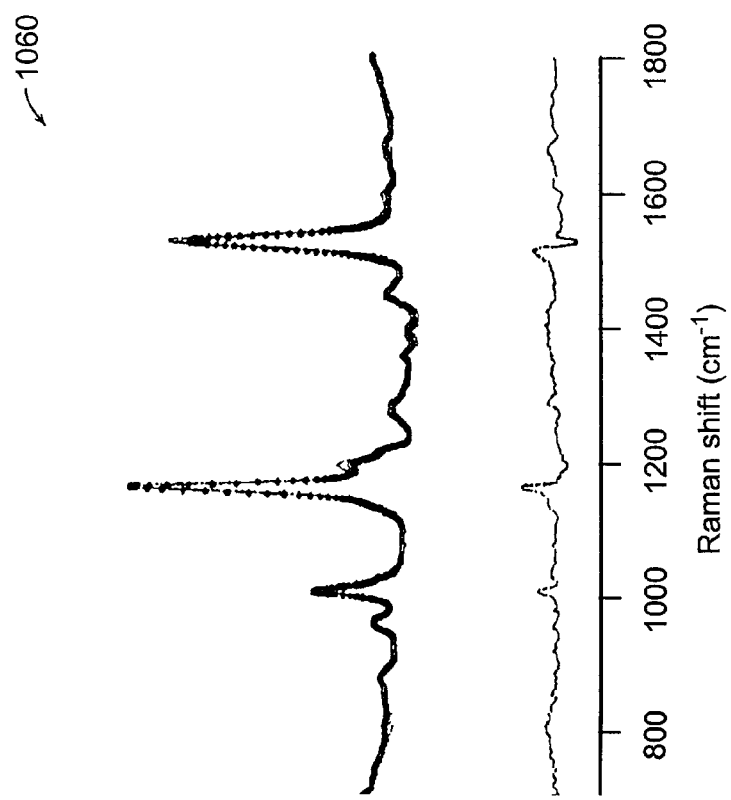
Figures 37A, 37B:
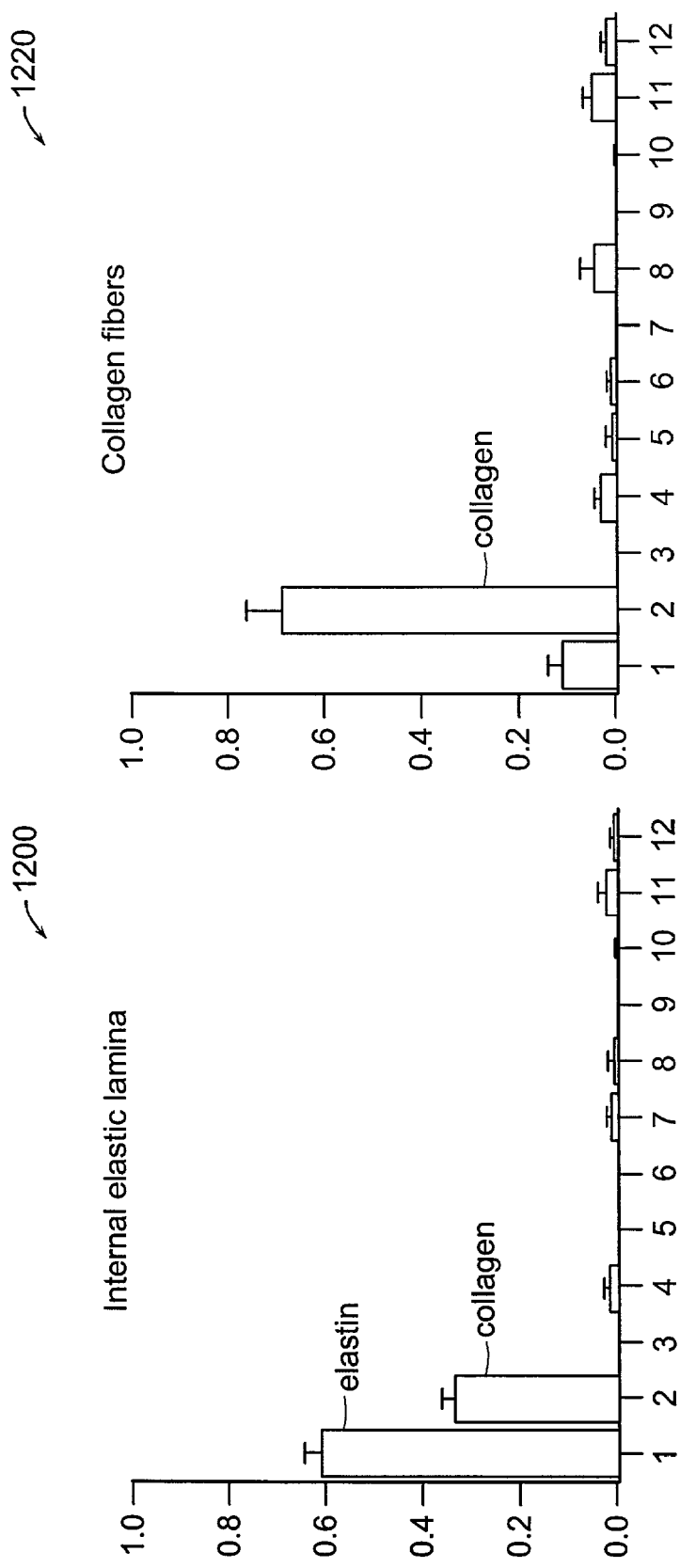
FIGS. 37A-37H graphically illustrate the biochemical composition of each morphologic structure in accordance with a preferred embodiment of the present invention.
Figures 37C, 37D:
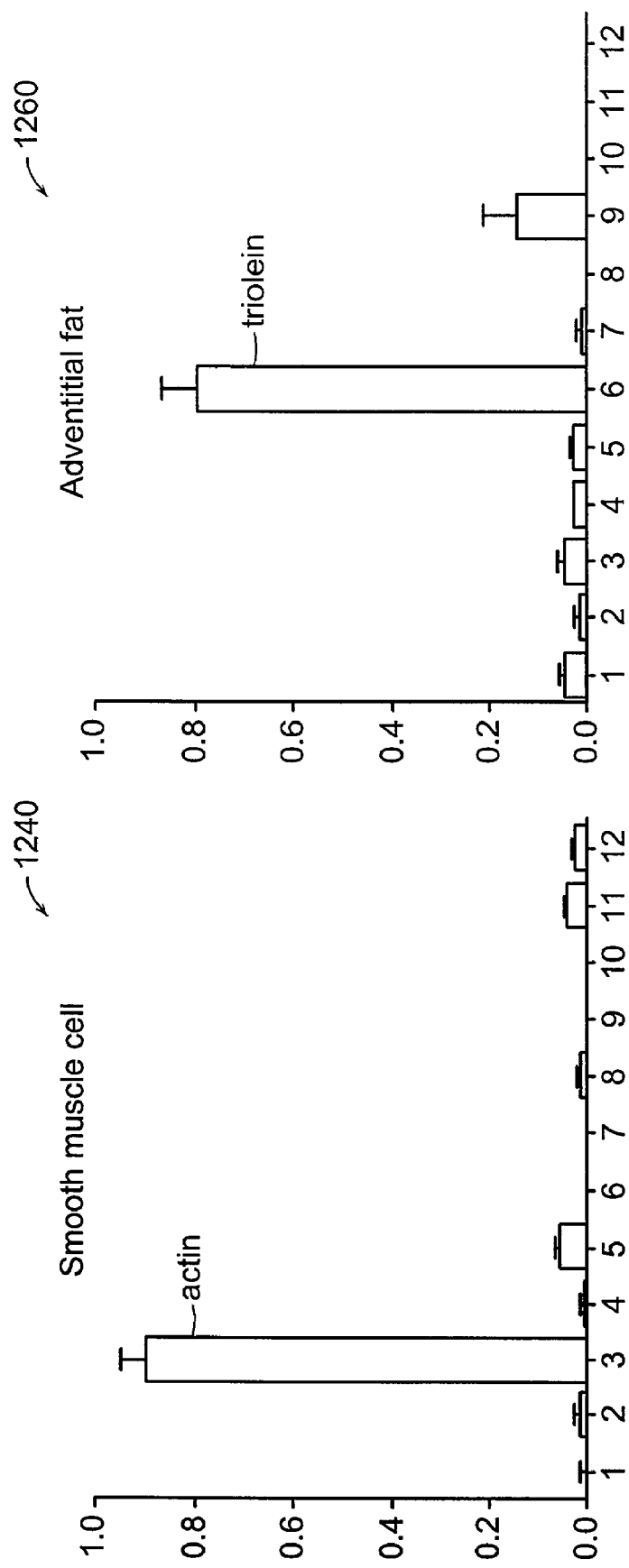
Figures 37E, 37F:
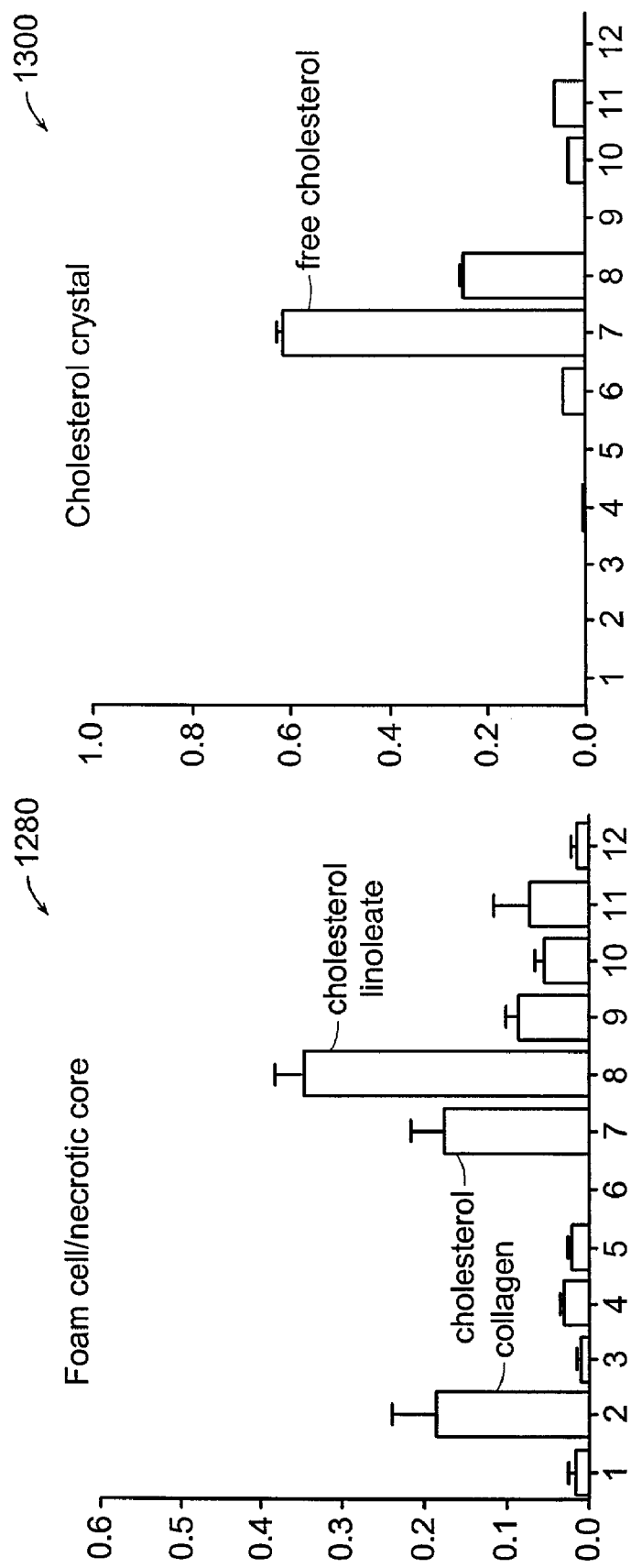
Figures 37G, 37H:
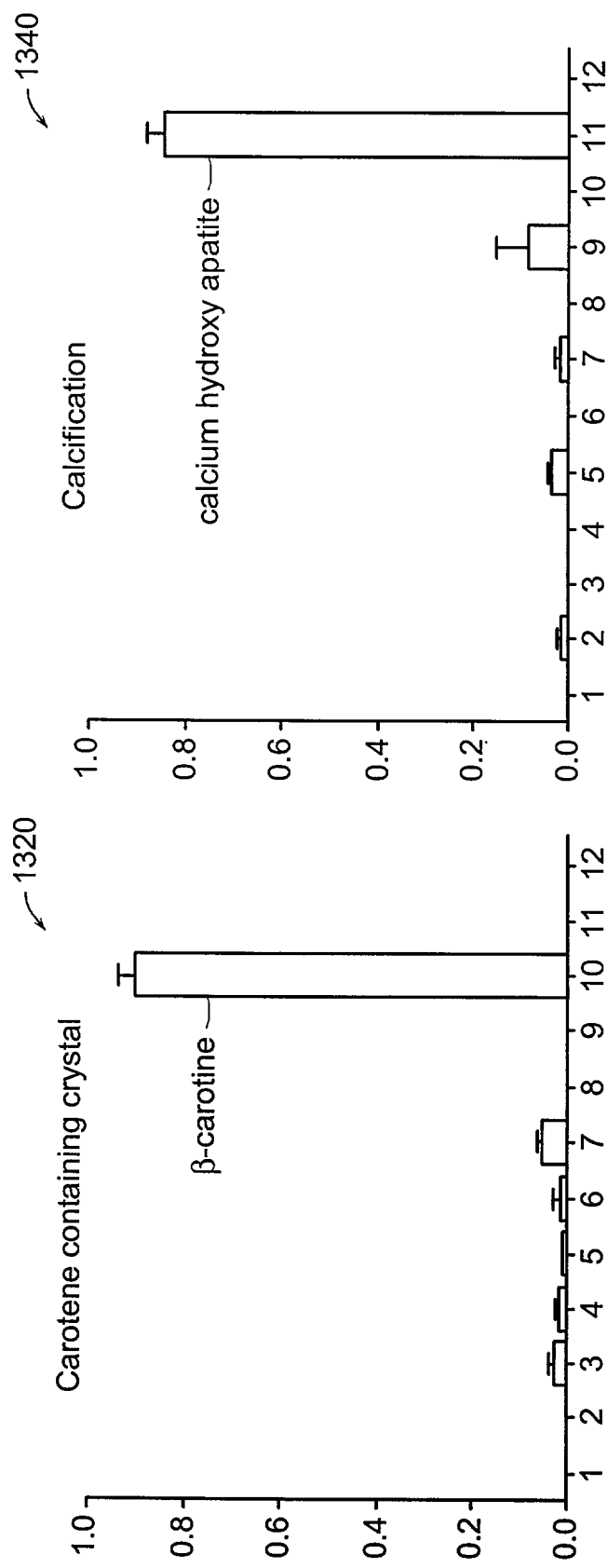

Using the basis spectra of pure chemicals as illustrated in FIG. 35, the spectra of the individual morphologic structures were fitted in the biochemical model. Each panel in FIGS. 36A-H shows a Raman spectrum of one of the morphologic structures, and the result of the least-squares minimization fit of the biochemical model. Residuals (data minus the fit) are shown on the same scale. Because the Raman spectra from foam cells and necrotic core were very similar, only the fit results of the foam cells are shown. Judging from the residuals of the fits to the observed spectra, which are on the order of magnitude of the noise and show no consistent pattern from spectrum to spectrum, the Raman spectrum of each morphologic structure (panels A-H) is well described using the 12 biochemical basis spectra.

For each morphologic structure examined, the contribution of each biochemical component was determined. FIGS. 37A-H confirm that each morphologic structure has a characteristic biochemical composition. Generally, each morphologic structure is composed largely of one or two major biochemical components, combined with one or more less abundant biochemical components.

The internal and external elastic laminae (FIG. 37A) are mainly composed of elastin with a smaller collagen component, whereas collagen fibers in both normal arteries and the fibrous cap of atherosclerotic lesions (FIG. 37B) are mainly composed of collagen with a small elastin component. Smooth muscle cells (FIG. 37C) were modeled almost entirely by actin and a small tropomyosin component. Myosin did not contribute at all.

Adventitial fat cells (FIG. 37D) contain almost exclusively triglycerides (triolein) with a small contribution of phospholipids (phosphatidyl choline). In contrast, foam cells and necrotic core (FIG. 37E) contains mainly cholesterol esters (linoleate) and free cholesterol (monohydrate) at a ratio of about 2:1, with smaller contributions of collagen, phospholipids, and β-carotene. Foam cells appear similar in the current data and cannot be distinguished from necrotic core on the basis of their biochemical composition. However in a following assessment they can be distinguished. For example, the spectral feature at approximately 1750 $cm^{-1}$ can be used to distinguish the foam cells from the necrotic core. Cholesterol crystals (FIG. 37F) contain free cholesterol and cholesterol ester at a ratio of about 3:1. The yellow crystals (FIG. 37G) consist almost entirely of β-carotene, with a small contribution of cholesterol. This may indicate that these crystals are in fact cholesterol crystals that contain high concentrations of β-carotene. Calcium mineralizations (FIG. 37H) are mainly composed of calcium hydroxypatite with small contributions of collagen, triglycerides, and calcium carbonate.

The presence of foam cells and other inflammatory cells may also play a role in plaque instability. Therefore, morphologic factors, such as the presence of crystalline-free cholesterol or foam cells, may be as important as biochemical composition in determining atherosclerotic plaque stability and progression.

As was shown in FIG. 36, the biochemical model of FIG. 35 describes the spectrum of each morphologic structure well, which means that the most essential biochemical components are included in the reference. The biochemical composition of each structure, indicated by the fit contributions of the biochemical basis spectra to the morphologic structure spectrum, is very consistent (FIGS. 36A-H). The largest biochemical variations were found in foam cells, necrotic core, cholesterol crystals, and calcium mineralizations. The biochemical variations in both calcium mineralizations, cholesterol crystals, and β-carotene-containing crystals may be due to differences in their stage of progression (as reflected by size). The cause of the biochemical variations within foam cells and necrotic core (differences in collagen, β-carotene, and cholesterol esters) is less clear. Variations in the lipid composition of atherosclerotic plaques at various stages of progression have been described previously in in-vitro studies of homogenized or extracted tissues and cultured monocyte-derived foam cells. However, these biochemical data are the results of analysis of atherosclerotic plaque components in-situ, without the confounding effects of tissue preparation or in-vitro cell culture models. More detailed in-situ Raman microspectroscopy studies of foam cells and necrotic cores in atherosclerotic plaques at various stages of disease progression may help to further elucidate the origin of this variation.

Although the biochemical model did provide valuable information on the biochemical composition of the microscopic cellular and extracellular morphologic structures, it has its limitations. One of the major limitations of this model and/or reference was illustrated by the fits of the smooth muscle cell spectra. Previous in-vitro studies have shown that smooth muscle cells, which comprise the majority of the tunica media of muscular arteries such as the coronary artery, contain approximately three times more actin than myosin, but approximately equal amounts of myosin and tropomyosin. However, the fit contributions in the biochemical model indicated that smooth muscle cells contained almost exclusively actin, with a small amount of tropomyosin and virtually no myosin. These unexpected results may be due to conformational differences in spectroscopic characteristics of myosin between tissue-extracted myosin and intracellular myosin in-situ. In addition, as seen with the glycosaminoglycans, the contribution of weak Raman scatterers may be underestimated.

Observed variations may also be due to contributions of biochemical compounds that are not included in the reference. For example, only one class of collagen was included. This should not be a great concern, as there is little difference observed in the Raman spectra of the different classes of collagens in-vitro. However, there may be significant changes in the Raman spectra of collagen in-vivo due to increased crosslinking as atherosclerotic lesions progress.

Despite these limitations, the results of previous quantitative Raman spectroscopic biochemical analyses of normal and atherosclerotic arterial tissue, using the same biochemical model, compared well with standard analytical techniques. Previous studies have also shown that these quantitative Raman spectroscopy biochemical analyses could be used as the basis of a diagnostic algorithm that accurately classified arterial tissues as either nonatherosclerotic or calcified or noncalcified atherosclerotic plaque. The results of the preferred embodiments of the present invention indicate that a modification of the biochemical model can be used to perform a relative comparison of cellular and extra cellular morphologic components of normal and atherosclerotic arterial tissue. Furthermore, another preferred embodiment shows that these relative morphologic comparisons can be used as the basis for an algorithm that allows diagnosis of atherosclerosis in coronary arteries. This is the first step in developing a quantitative Raman spectroscopy morphologic analysis with the purpose to accurately classify normal arteries and atherosclerotic plaques ex vivo, and in the future to predict plaque stability and disease progression in-vivo.

Using the biochemical model reference of the preferred embodiment, confocal Raman microspectroscopy is illustrated to be used to perform an in-situ biochemical analysis of individual microscopic morphologic structures (such as foam cells and necrotic core) in intact arterial tissues that cannot be isolated or purified using conventional analytical techniques. Furthermore, the various morphologic structures have characteristic Raman spectra, which, as expected, vary little from structure to structure or from artery to artery, and can be used as basis spectra in a morphologic reference to perform a relative comparison of the morphology of normal and atherosclerotic coronary arteries ex-vivo. This nondestructive technique may ultimately be used to assess plaque stability and disease progression in humans in-vivo, as well as to study atherogenesis in animal models and lipid metabolism in cell cultures in-vitro.

The embodiments of the present invention interpret Raman spectra in terms of morphology. For example, the Raman spectra can be associated with a morphological structure, for example, a foam cell which can be associated with specific chemical compounds. Further, the number of spectra can be reduced, for example, from a large number of chemical spectra to only eight unique spectra associated with morphological structures thereby decreasing the error in the fit. The diagnostics that are available to identify and monitor vulnerable plaque using the optical fiber catheter system of the present invention include the use of chemical composition, information about the morphological structures, thickening of the intimal layer and the thinning of the overlying collagen layer. Preferred embodiments include the determination of the depth of collagen by measuring the percentage of collagen. Further, the presence of calcification is monitored and any edges are identified and located relative to the collagen as indicators of a potential rupture and blood clot. As discussed previously, the reduced fractional fit contributions of collagen fibers in non-calcified plaques is an indicator of unstable plaque.

The claims should not be read as limited to the described order or elements unless stated to that effect. Therefore, all embodiments that come within the scope and spirit of the following claims and equivalents thereto are claimed as the invention.

What is claimed:

1. A probe for measuring tissue, comprising:
   a fiber optic probe having a proximal end, a distal end, a tubular body having a diameter of 2 mm or less;
   a delivery optical fiber in the probe coupled at the proximal end to a light source and having a first filter at a distal end of the delivery optical fiber that filters light from the light source transmitted through the delivery optical fiber;
   a plurality of collection optical fibers in the probe that collects Raman scattered radiation from tissue, the collection optical fibers being coupled at the proximal end to a detector and having a second filter at a distal end of the collection optical fibers that filters light collected at the distal end through the collection optical fibers; and
   an optical module having a rod within a cylindrical tube and a sleeve that optically isolates the cylindrical rod from the tube, the first filter being formed on a proximal surface of the rod and the second filter being formed on a proximal surface of the cylindrical tube such that collected light is transmitted through the cylindrical tube and the second filter before entering the distal ends of the plurality of collection fibers;

an optical lens system at the distal end of the optical module that is optically coupled to the distal end of the delivery fiber and the collection optical fibers through the optical module, the optical system including a refractive optical element at the distal end of the tubular body.

2. The probe of claim 1 wherein the optical lens system comprises a ball lens optically coupled to the delivery fiber and the collection fiber through the optical module.

3. The probe of claim 1 further comprising a second sleeve is positioned between a distal end of the delivery optical fiber and the collection optical fibers.

4. The probe of claim 1 further comprising a first plurality of collection fibers arranged concentrically about the delivery fiber at a first radius, and a second plurality of collection fibers arranged concentrically about the delivery fiber at a second radius that is larger than the first radius.

5. The probe of claim 1 further comprising a controller that gates a collection time, the collection time being less than 2 seconds.

6. The probe of claim 1 wherein the optical lens system has a length less than 10 mm.

7. The probe of claim 1 wherein the optical lens system has a length of less than 4 mm.

8. The probe of claim 1 wherein the light source has a wavelength longer than 750 nm.

9. The probe of claim 1 wherein the optical lens systems delivers and collects radiation in a radial direction.

10. The probe of claim 1 wherein the probe measures spectral features of cardiac tissue.

11. A spectroscopic diagnostic system for measuring tissue comprising:

a fiber optic probe having a proximal end, a tubular body and a distal end;

a central delivery optical fiber in the probe coupled at the proximal end to a light source to deliver radiation to the distal end, the delivery optical fiber having a first filter at a distal end of the central delivery fiber;

a plurality of collection optical fibers positioned around the delivery fiber in the probe that collect Raman scattered radiation from tissue, the collection optical fibers being coupled at the proximal end to a detector system, the collection optical fibers having a second filter at a distal end of the collection optical fibers;

an optical module having a rod such that the first filter is formed on a proximal surface of the rod, the optical module further including a cylindrical tube being concentric about the rod with a sleeve that optically isolates the rod from the cylindrical tube, the second filter being formed on a proximal surface of the cylindrical tube such that collected light is transmitted through the cylindrical tube and the second filter before entering the collection optical fibers; and an optical lens system at the distal end of the probe, the optical lens system being optically coupled to a distal end of the optical module.

12. The spectroscopic diagnostic system of claim 11 wherein the first filter and the second filter are coplanar.

13. The spectroscopic diagnostic system of claim 11 wherein the lens system comprises an elliptical axicon optically coupled to the delivery optical fiber and the collection optical fiber.

14. The spectroscopic diagnostic system of claim 11 further comprising a second sleeve that is positioned between a distal end of the delivery fiber and the collection fibers.

15. The spectroscopic diagnostic system of claim 11 further comprising a first plurality of collection fibers arranged concentrically about the delivery fiber at a first radius, and a second plurality of collection fibers arranged concentrically about the delivery fiber at a second radius that is larger than the first radius.

16. The spectroscopic diagnostic system of claim 11 wherein the spectroscopic diagnostic system generates a circumferential image.

17. The spectroscopic diagnostic system of claim 11 further comprising a controller that gates a collection time, the collection time being less than 2 seconds.

18. The spectroscopic diagnostic system of claim 11 wherein the optical lens system has a length less than 10 mm.

19. The spectroscopic diagnostic system of claim 11 wherein the optical lens system has a length of less than 4 mm.

20. The spectroscopic diagnostic system of claim 11 wherein the light source has a wavelength longer than 750 nm.

21. The spectroscopic diagnostic system of claim 11 wherein the optical lens systems delivers and collects radiation in a radial direction.

* * * * *

UNITED STATES PATENT AND TRADEMARK OFFICE
CERTIFICATE OF CORRECTION

| | |
|---|---|
| PATENT NO. | : 7,647,092 B2 |
| APPLICATION NO. | : 10/178062 |
| DATED | : January 12, 2010 |
| INVENTOR(S) | : Motz et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1066 days.

Page 1 of 1

Signed and Sealed this

Sixteenth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,647,092 B2 | Page 1 of 1 |
| APPLICATION NO. | : 10/178062 | |
| DATED | : January 12, 2010 | |
| INVENTOR(S) | : Jason T. Motz et al. | |

It is certified that error appears in the above-identified patent and that said Letters Patent is hereby corrected as shown below:

Column 1, following "GOVERNMENT SUPPORT" please delete lines 14-17 and insert the new paragraph as follows:

--This invention was made with government support under Grant Nos. P41 RR002594 and 5-R01-HL64675-03, awarded by the National Institutes of Health. The government has certain rights in this invention.--

Signed and Sealed this

Seventeenth Day of May, 2011

David J. Kappos
*Director of the United States Patent and Trademark Office*